United States Patent
Shrader et al.

(10) Patent No.: US 11,155,580 B2
(45) Date of Patent: *Oct. 26, 2021

(54) MODIFIED PROTEINS AND METHODS OF USE THEREOF

(71) Applicant: YALE UNIVERSITY, New Haven, CT (US)

(72) Inventors: Alanna Schepartz Shrader, Wilton, CT (US); Jacob S. Applebaum, New Haven, CT (US); Jonathan R. LaRochelle, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/250,213

(22) Filed: Jan. 17, 2019

(65) Prior Publication Data

US 2019/0211062 A1 Jul. 11, 2019

Related U.S. Application Data

(63) Continuation of application No. 14/783,943, filed as application No. PCT/US2014/034003 on Apr. 14, 2014, now Pat. No. 10,227,384.

(Continued)

(51) Int. Cl.
*A61K 47/42* (2017.01)
*A61K 47/64* (2017.01)
(Continued)

(52) U.S. Cl.
CPC .............. *C07K 14/00* (2013.01); *A61K 47/42* (2013.01); *A61K 47/645* (2017.08);
(Continued)

(58) Field of Classification Search
CPC ........ A61K 38/02; A61K 38/03; A61K 38/10; A61K 38/16; A61K 38/1703; A61K 47/42; A61K 47/48246; A61K 47/48315; A61K 47/64; A61K 47/645; A61K 47/6455; C07K 2/00; C07K 4/12; C07K 7/08;
(Continued)

(56) References Cited

U.S. PATENT DOCUMENTS 5,093,241 A 3/1992 Bennett
6,664,040 B2 12/2003 Sherman
(Continued)

FOREIGN PATENT DOCUMENTS

WO 2008133929 A2 11/2008

OTHER PUBLICATIONS

Appelbaum et al. Arginine Topology Controls Escape of Miniature Proteins from Early Endosomes. Chemistry & Biology. Jul. 27, 2012, vol. 19, pp. 819-830.
(Continued)

*Primary Examiner* — Jeffrey E. Russel
(74) *Attorney, Agent, or Firm* — Riverside Law LLP

(57) ABSTRACT

This invention is generally related to small proteins, such as miniature proteins, including avian pancreatic polypeptide (aPP), modified so that the small proteins reach the cytosol. In some embodiments, the modified protein molecules deliver an associated cargo molecule to the cytosol. Other embodiments of the invention relate to modified protein fusion molecules that reach the cytosol.

19 Claims, 36 Drawing Sheets

Specification includes a Sequence Listing.

| | | | |
|---|---|---|---|
| SAH-p53-4 | LSQETF*DLWKLL*EN | SEQ ID NO:38 | active *in vitro*, not *in cellulo* or *in vivo* |
| SAH-p53-4-5.3 | RSQERF*RLWRRL*EN | SEQ ID NO:39 | |
| SAH-p53-8 | QSQQTF*NLWRLL*QN | SEQ ID NO:40 | active *in vitro*, *in cellulo* and *in vivo* |
| SAH-p53-8-5.3 | RSQQRF*RLWRRL*QN | SEQ ID NO:41 | |

Related U.S. Application Data

(60) Provisional application No. 61/811,567, filed on Apr. 12, 2013, provisional application No. 61/858,874, filed on Jul. 26, 2013, provisional application No. 61/871,045, filed on Aug. 28, 2013.

(51) Int. Cl.
| | |
|---|---|
| *C07K 7/08* | (2006.01) |
| *C07K 14/00* | (2006.01) |
| *C07K 19/00* | (2006.01) |
| *C07K 14/575* | (2006.01) |
| *C07K 14/465* | (2006.01) |
| *C07K 14/47* | (2006.01) |
| *A61K 38/00* | (2006.01) |

(52) U.S. Cl.
CPC ............ *A61K 47/6455* (2017.08); *C07K 7/08* (2013.01); *C07K 14/465* (2013.01); *C07K 14/47* (2013.01); *C07K 14/575* (2013.01); *A61K 38/00* (2013.01); *C07K 2319/10* (2013.01); *C07K 2319/81* (2013.01)

(58) Field of Classification Search
CPC .... C07K 14/00; C07K 14/465; C07K 14/575; C07K 2319/10; C07K 2319/81
See application file for complete search history.

(56) References Cited

U.S. PATENT DOCUMENTS

| | | | | |
|---|---|---|---|---|
| 7,101,844 | B2 | 9/2006 | Dae-You | |
| 7,297,762 | B2 | 11/2007 | Shrader | |
| 8,124,721 | B2* | 2/2012 | Donini | A61P 31/10 530/300 |
| 8,329,650 | B2* | 12/2012 | Walsh | A61P 3/10 514/15.1 |
| 10,227,384 | B2* | 3/2019 | Schepartz | C07K 14/575 |
| 2005/0118678 | A1 | 6/2005 | Mayo | |
| 2010/0036088 | A1 | 2/2010 | Barron | |
| 2012/0270808 | A1* | 10/2012 | Kolonin | C12N 15/1037 514/21.2 |
| 2012/0321668 | A1* | 12/2012 | Shai | A61P 13/12 424/281.1 |
| 2017/0081425 | A1* | 3/2017 | Colletti | C12N 15/113 |

OTHER PUBLICATIONS

Ho et al. Synthetic Protein Transduction Domains: Enhanced Transduction Potential in Vitro and in Vivo. Cancer Research. Jan. 15, 2001, vol. 61, pp. 474-477.
Holub, et al., 2013, 'Improved assays for determining the cytosolic access of peptides, proteins, and their mimetics'. Biochemistry, 52(50):9036-9046.
Luedtke et al., 2003, "Cellular Uptake of Aminoglycosides, Guanidinoglycosides, and Poly-arginine". J Am Chem Soc. 125:12374-12375.
Ryser et al., 1965, "Histones and Basic Polyamino Acids Stimulate the Uptake of Albumin by Tumor Cells in Culture". Science. 150:501-503.
Zhou et al., 2009, "Generation of Induced Pluripotent Stem Cells Using Recombinant Proteins". Cell Stem Cell. 4:381-384.
Theodore et al., 1995, "Intraneuronal Delivery of Protein Kinase C Pseudosubstrate Leads to Growth Cone Collapse". J. Neurosci. 15:7158-7167.
Futaki et al., 2001, Arginine-rich Peptides—"An Abundant Source of Membrane-Permeable Peptides Having Potential as Carriers Forintracellular Protein Delivery". J Biol Chem. 276:5836-5840.
Wender et al., 2008, "The design of guanidinium-rich transporters and their internalization mechanisms". Adv Drug Deliv Rev 60:452-172.

Cronican et al., 2011, "A Class of Human Proteins that Deliver Functional Proteins into Mammalian Cells In Vitro and In Vivo". Chem Biol. 18:833-838.
Johannes et al., 2008, "Tracing the Retrograde Route in Protein Trafficking". Cell. 135:1175-1187.
Rothbard et al., 2005, "Adaptive translocation: the role of hydrogen bonding and membrane potential in the uptake of guanidinium-rich transporters into cells". Adv Drug Deliv Rev. 57:495-504.
Fischer, 2007, "Cellular uptake mechanisms and potential therapeutic utility of peptidic cell delivery vectors: Progress 2001-2006". Med Res Rev. 27:755-795.
Duchardt et al., 2007, "A Comprehensive Model for the Cellular Uptake of Cationic Cell-penetrating Peptides". Traffic. 8:848-866.
Palm-Apergi et al., 2009, "The membrane repair response masks membrane disturbances caused by cell-penetrating Peptide uptake". FASEB J 23:214-223.
Derossi et al., 1996, "Cell Internalization of the Third Helix of the Antennapedia Homeodomain Is Receptor-Independent". J Biochem. 271:18188-18193.
Wadia et al., 2004, "Transducible TAT-HA fusogenic peptide enhances escape of TAT-fusion proteins after lipid raft Macropinocytosis". Nat Med. 10:310-315.
Fischer et al., 2004, "A Stepwise Dissection of the Intracellular Fate of Cationic Cell-penetrating Peptides". J Biol Chem. 279:12625-12635.
Ter-Avetisyan et al., 2009, "Cell Entry of Arginine-rich Peptides Is Independent of Endocytosis". J Biol Chem 284:3370-3378.
Belitsky et al., 2002, "Cellular Uptake of N-Methylpyrrole/N-Methylimidazole Polyamide-Dye Conjugates". Bioorg Med Chem 10:3313-3318.
Richard et al., 2003, Cell-penetrating Peptides—"A Reevaluation of the Mechanism of Cellular Uptake". J Biol Chem. 278:585-590.
Maiolo et al., 2004, "Specific Redistribution of Cell-Penetrating Peptides from Endosomes to the Cytoplasm and Nucleus upon Laser Illumination". J Am Chem Soc. 126:15376-15377.
Erazo-Oliveras et al., 2012, "Improving the Endosomal Escape of Cell-Penetrating Peptides and Their Cargos: Strategies and Challenges". Pharmaceuticals 5:1177-1209.
Blundell et al., 1981, "X-ray analysis (1,4-A resolution) of avian pancreatic polypeptide: Small globular protein hormone". Proc Natl Acad Sci USA. 78:4175-4179.
Hodges et al., 2007, "Engineering a Monomeric Miniature Protein". J Am Chem Soc. 129:11024-11025.
Zondlo et al., 1999, "Highly Specific DNA Recognition by a Designed Miniature Protein". J Am Chem Soc. 121:6938-6939.
Zellefrow et al., 2006, "Encodable Activators of Src Family Kinases". J Am Chem Soc. 128:16506-16507.
Chin et al., 2001, "Design and Evolution of a Miniature Bcl-2 Binding Protein". Chem. Int. Ed. Engl. 40:3806-3809.
Rutledge et al., 2003, "Molecular recognition of protein surfaces: High affinity ligands for the CBP KIX domain". J Am Chem Soc. 125:14336-14347.
Golemi-Kotra et al., 2004, "High Affinity, Paralog-Specific Recognition of the Mena EVH1 Domain by a Miniature Protein". J Am Chem Soc. 126:4-5.
Gemperli et al., 2005, "Paralog-Selective Ligands for Bcl-2 Proteins". J Am Chem Soc. 127:1596-1597.
Daniels et al., 2007, Intrinsically Cell-Permeable Miniature Proteins Based on a Minimal Cationic PPII Motif. J Am Chem Soc. 129:14578-14579.
Smith et al., 2008, "Minimally Cationic Cell-Permeable Miniature Proteins via a-Helical Arginine Display". J Am Chem Soc. 130:2948-2949.
Simpson, 2004, "Identification of the Major Steps in Botulinum Toxin Action", Annual Review Pharmacology Toxicology, 44:167-193.
Vonderheit et al., 2005, "Rab7 Associates with Early Endosomes to Mediate Sorting and Transport of Semliki Forest Virus to Late Endosomes". Plos Biol. 3:e233.
Vidricaire et al., 2005, "Rab5 and Rab7, but Not ARF6, Govern the Early Events of HIV-1 Infection in Polarized Human Placental Cells". J Immunol. 175:6517-6530.

(56) References Cited

OTHER PUBLICATIONS

Lipinski et al., 2001, "Experimental and computational approaches to estimate solubility and permeability in drug discovery and development settings". Adv Drug Deliv Rev. 46:3-26.

Gaj et al., 2012, "Targeted gene knockout by direct delivery of ZFN proteins". Nat. Methods 9:805-807.

Yu et al., 2011, "Overcoming Endosomal Barrier by Amphotericin B-Loaded Dual pH-Responsive PDMA-b-PDPA Micelleplexes for siRNA Delivery". ACS Nano 5:9246-9255.

Yu et al., 2005, "A high-throughput assay for assessing the cell permeability of combinatorial libraries". Nat Biotechnol. 23:746-751.

Carey et al., 1996, "Evidence Using a Green Fluorescent Protein-Glucocorticoid Receptor Chimera that the RAN/TC4 GTPase Mediates an Essential Function Independent of Nuclear Protein Import". J Cell Biol. 133:985-996.

Palm et al., 2007, "Peptide degradation is a critical determinant for cell-penetrating peptide uptake". Biochim Biophys Acta 1768:1769-1776.

Lakadamyali et al., 2006, "Ligands for Clathrin-Mediated Endocytosis Are Differentially Sorted into Distinct Populations of Early Endosomes". Cell. 124:997-1009.

Zoncu et al., 2009, "A Phosphoinositide Switch Controls the Maturation and Signaling Properties of APPL Endosomes". Cell. 136:1110-1121.

Zeigerer et al., 2012, "Rab5 is necessary for the biogenesis of the endolysosomal system in vivo". Nature 485:465-470.

Christoforidis et al., 1999, "Phosphatidylinositol-3-OH kinases are Rab5 effectors". Nat Cell Biol. 1:249-252.

Stenmark et al., 1994, "Inhibition of rab5 GTPase activity stimulates membrane fusion in endocytosis". EMBO J 13:1287-1296.

Puthenveedu et al., 2010, "Sequence-Dependent Sorting of Recycling Proteins by Actin-Stabilized Endosomal Microdomains". Cell. 143:761-773.

Cantalupo et al., 2001, "Rab-interacting lysosomal protein (RILP): the Rab7 effector required for transport to ysosomes". EMBO J. 20:683-693.

Huotari et al., 2011, "Endosome maturation". EMBO J. 30:3481-3500.

Sera, 2009, "Zinc-finger-based artificial transcription factors and their applications". Adv Drug Deliv Rev. 61:513-526.

Urnov et al., 2010, "Genome editing with engineered zinc finger nucleases". Nat Rev Genet. 11:636-646.

Krizek et al., 1991, "A consensus zinc finger peptide: design, high-affinity metal binding, a pH-dependent structure, and a His to Cys sequence variant". J Am Chem Soc. 113:4518-4523.

Picard et al., 1987, "Two signals mediate hormone-dependent nuclear localization of the glucocorticoid receptor". EMBO J. 6:3333-3340.

Beato, 1989, "Gene Regulation by Steroid Hormones". Cell 56:335-344.

Kwon et al., 2007, "Quantitative Evaluation of the Relative Cell Permeability of Peptoids and Peptides". J. Am. Chem. Soc. 129:1508-1509.

Chakraborti et al., 1991, "Creation of "Super" Glucocorticoid Receptors by Point Mutations in the Steroid Binding Domain". J. Biol. Chem. 266:22075-22078.

Chakraborti et al., 1992, "Role of Cysteines 640, 656, and 661 in Steroid Binding to Rat Glucocorticoid Receptor". J. Biol. Chem. 267, 11366-11373.

Mitchell et al., 2000, "Polyarginine enters cells more efficiently than other polycationic homopolymers". J. Peptide Res. 56:318-325.

Luedtke et al., 2007, "Surveying polypeptide and protein domain conformation and association with FlAsH and ReAsH". Nat. Chem. Biol. 3, 779-784.

\* cited by examiner

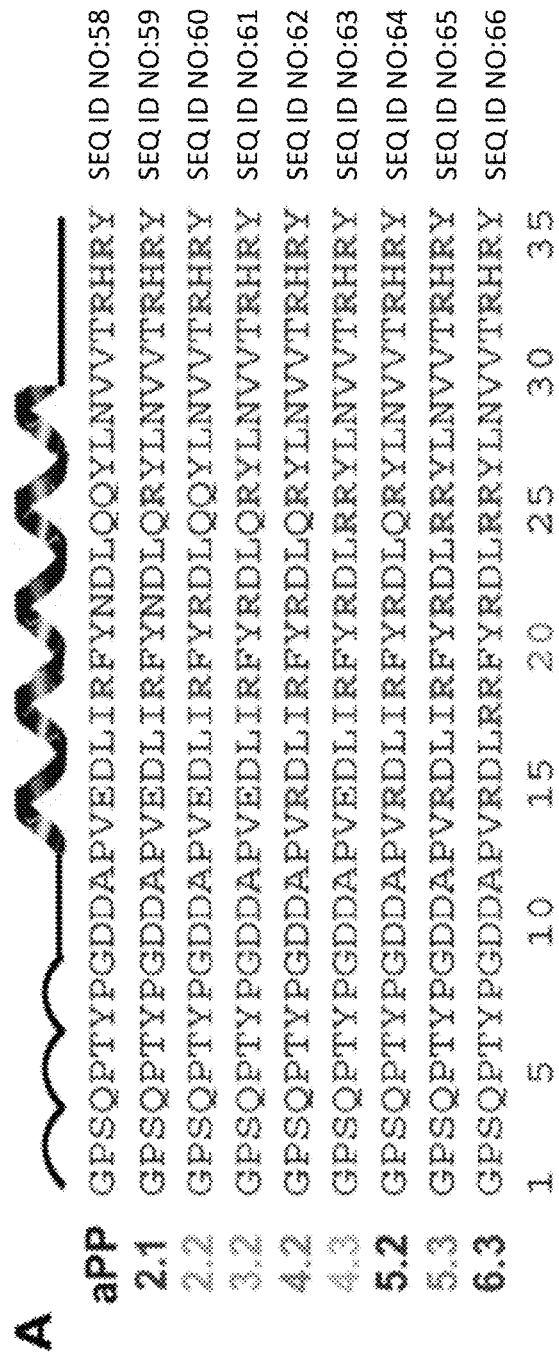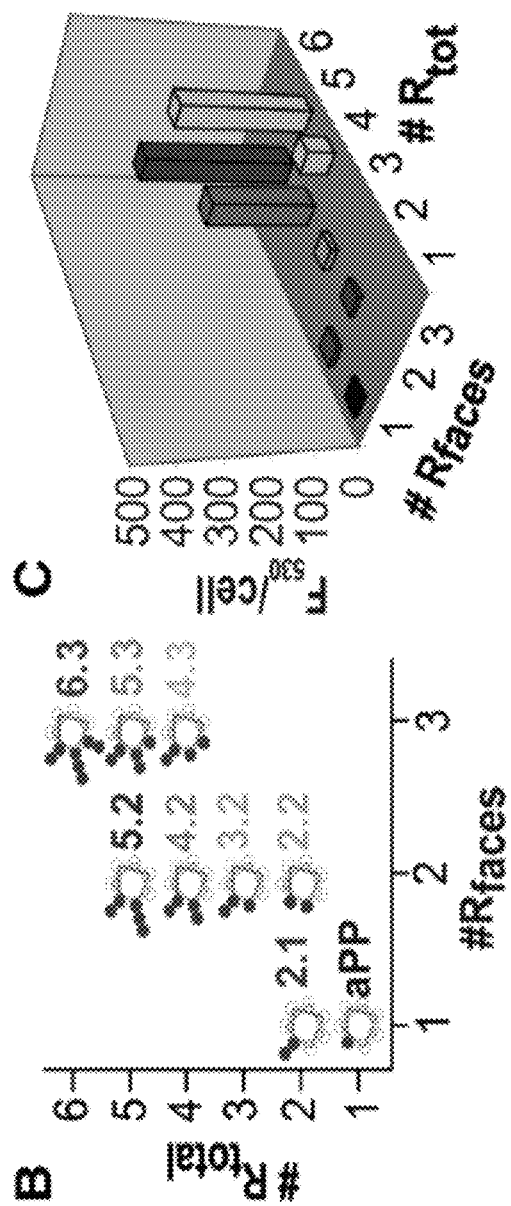
Figure 1

| molecule | [molecule] in cytosol (nM) | % in cytosol |
|---|---|---|
| ZF5.3 | 249 | 59 |
| aPP5.3 | 152 | 30 |
| stapled peptide | 211 | 42 |
| Tat | 4.63 | 0.93 |
| Arg8 | 14.0 | 2.8 |
| +36GFP | N/A | N/A |

Figure 15

| | | | |
|---|---|---|---|
| SAH-p53-4 | LSQETF*DLWKLL*EN | SEQ ID NO:38 | active *in vitro*, not *in cellulo* or *in vivo* |
| SAH-p53-4-5.3 | RSQERF*RLWRRL*EN | SEQ ID NO:39 | |
| SAH-p53-8 | QSQQTF*NLWRLL*QN | SEQ ID NO:40 | active *in vitro*, *in cellulo* and *in vivo* |
| SAH-p53-8-5.3 | RSQQRF*RLWRRL*QN | SEQ ID NO:41 | |

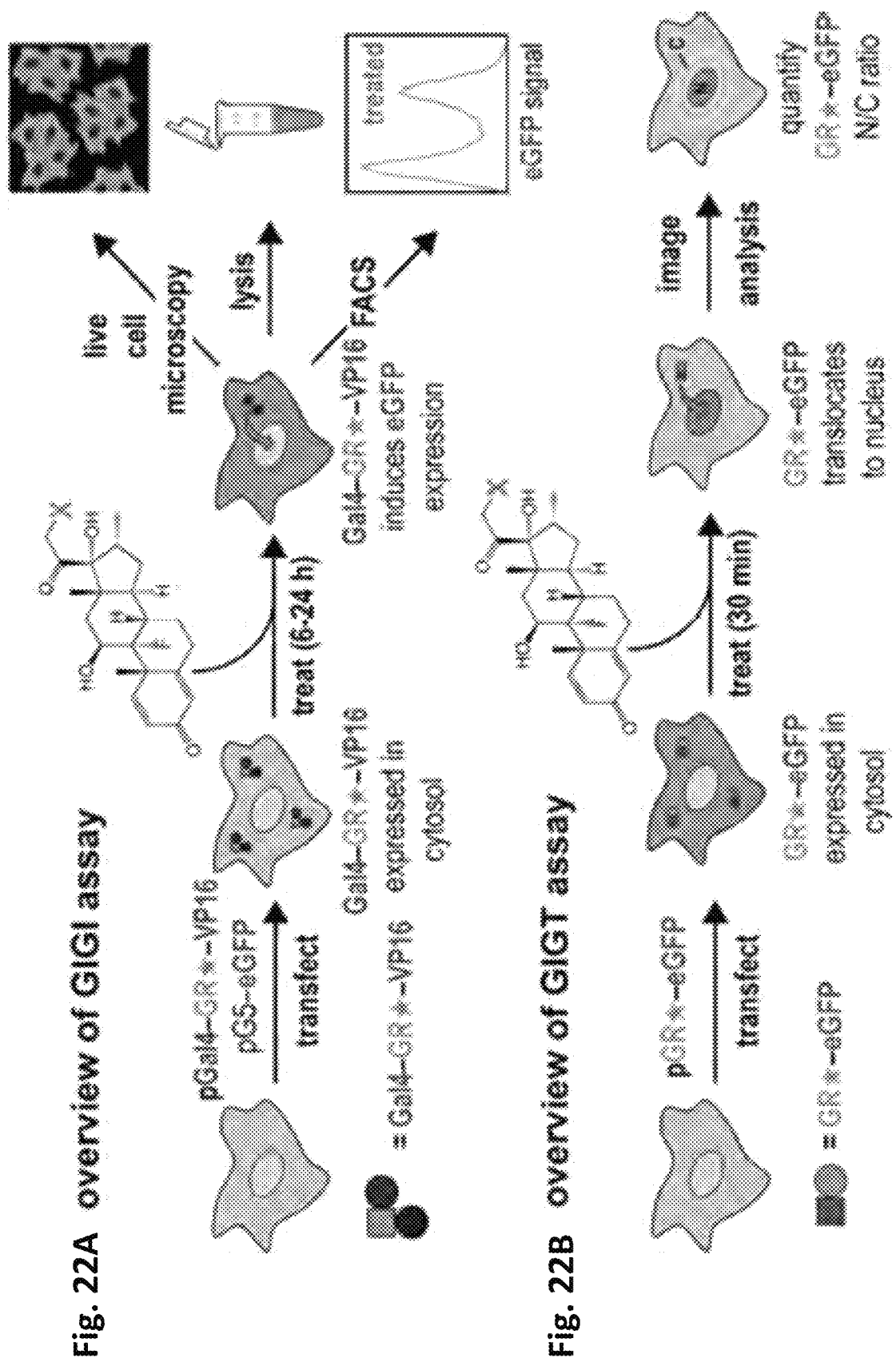
Fig. 22A overview of GIGI assay
Fig. 22B overview of GIGT assay

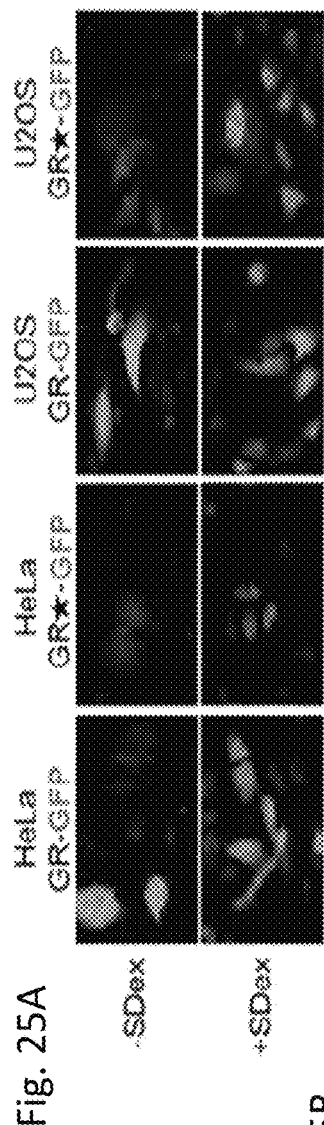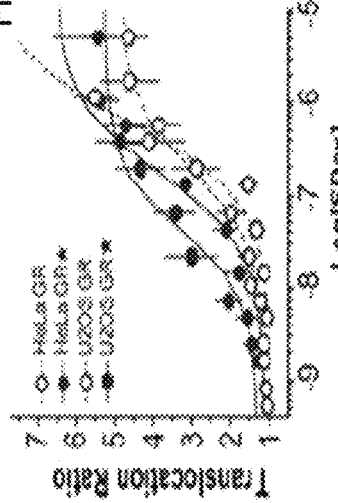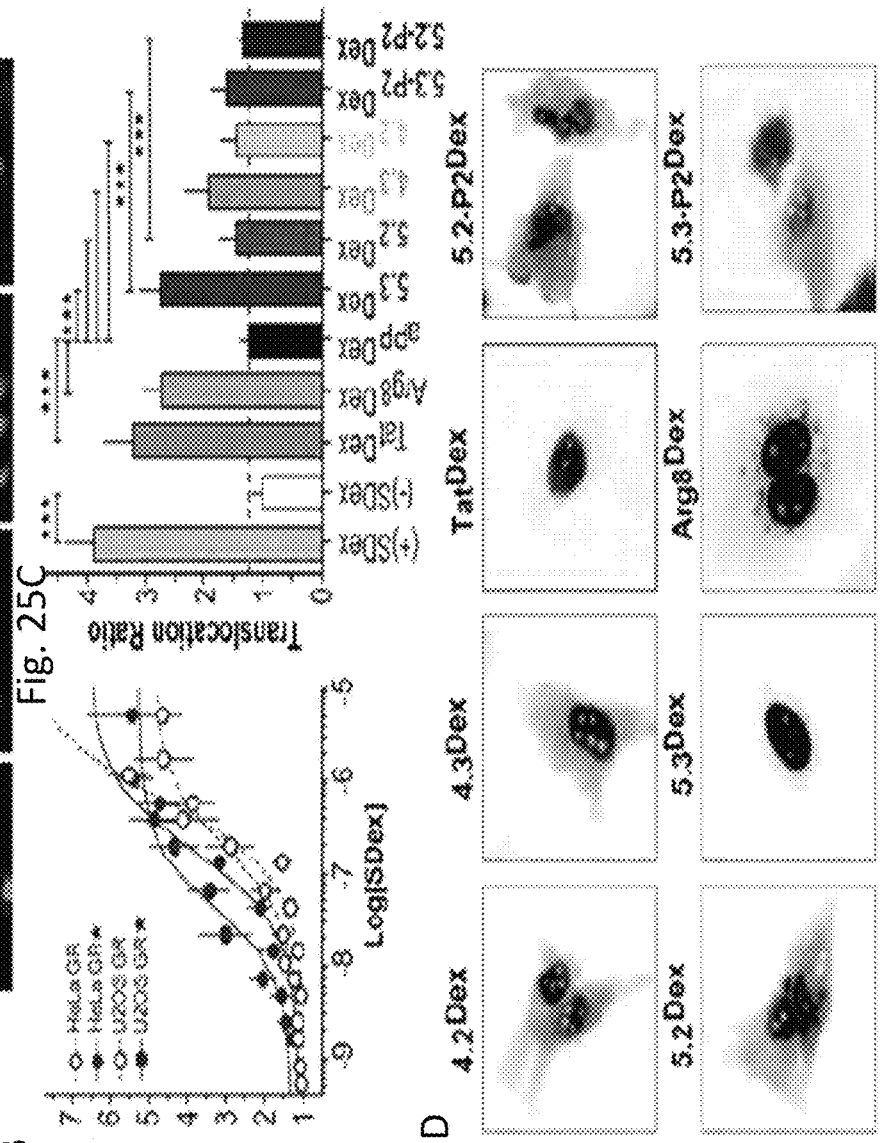
Fig. 25A
Fig. 25B
Fig. 25C
Fig. 25D

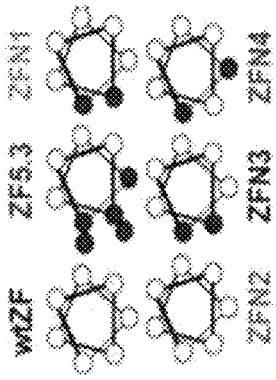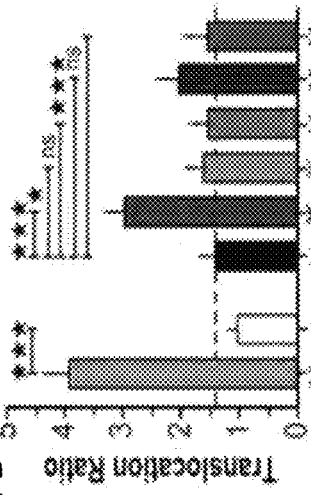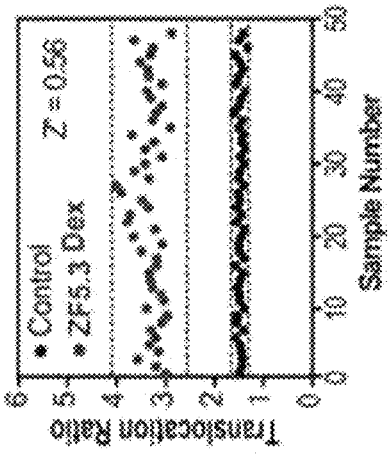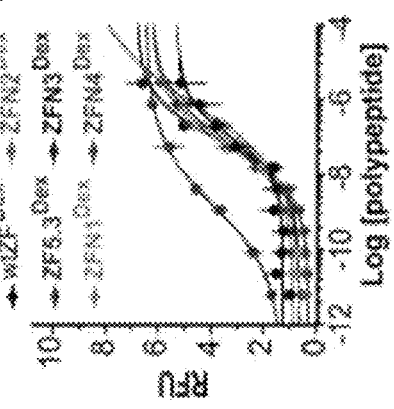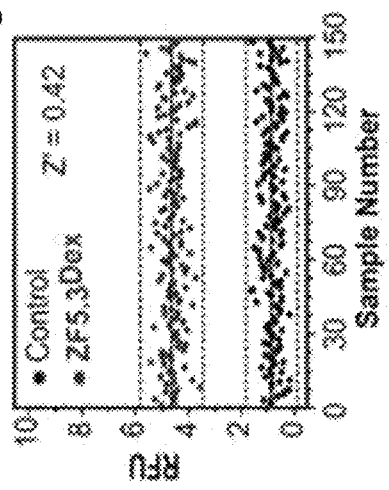
Fig. 27A, Fig. 27B, Fig. 27C, Fig. 27D, Fig. 27E, Fig. 27F

MODIFIED PROTEINS AND METHODS OF USE THEREOF

CROSS-REFERENCE TO RELATED APPLICATIONS

The present application is a Continuation of U.S. patent application Ser. No. 14/783,943, filed Oct. 12, 2015, which is the U.S. national phase application filed under 35 U.S.C. § 371 claiming benefit to International Patent Application No. PCT/US14/34003, filed Apr. 14, 2014, which claims priority to U.S. Provisional Application Ser. No. 61/811,567, filed Apr. 12, 2013, U.S. Provisional Application Ser. No. 61/858,874, filed Jul. 26, 2013, and U.S. Provisional Application Ser. No. 61/871,045, filed Aug. 28, 2013, and all of which applications are hereby incorporated by reference in their entireties herein.

STATEMENT REGARDING FEDERALLY SPONSORED RESEARCH OR DEVELOPMENT

This invention was made with government support under Grant Nos. HV028186 and GM74756 awarded by the National Institutes of Health (NIH). The government has certain rights in the invention.

BACKGROUND OF THE INVENTION

Protein and peptide drugs represent a rapidly expanding class of therapeutic molecules (Strohl and Knight, 2009, Curr Opin Biotechnol. 20:668-672). However, the actions of peptidic moelcues are limited primarily to extracellular targets (Fischer, 2007, Med Res Rev. 27:755-795; Johnson et al., 2011, Methods Mol Biol. 683:535-551) because the size and composition of most polypeptides and peptide mimetics do not facilitate efficient transport across the plasma membrane into the cytosol or nucleus of mammalian cells (Luedtke et al., 2003, J Am Chem Soc. 125:12374-12375). It has been known for over 40 years that addition of cationic charges to a peptide or protein can aid transport into cells (Ryser and Hancock, 1965, Science. 150:501-503), and many reports have demonstrated the utility of appending basic sequences derived from the HIV Trans-Activator of Transcription (Tat) (Zhou et al., 2009, Cell Stem Cell. 4:381-384), *D. melanogaster* Antennapedia (Théodore et al., 1995, J. Neurosci. 15:7158-7167), or simply polyarginine (for example, Arg8 (SEQ ID NO:68)) (Futaki et al., 2001, J Biol Chem. 276:5836-5840) to peptides or small molecules (Wender et al., 2008, Adv Drug Deliv Rev 60:452-472) to increase 'cell uptake'. Certain highly positively charged proteins (Cronican et al., 2011, Chem Biol. 18:833-838) and toxins (Johannes and Popoff, 2008, Cell. 135:1175-1187) are also 'taken up' by cells with varying levels of efficiency.

Two contrasting mechanisms have been proposed for the cytosolic entry of cationic proteins and related molecules. The first (ion pair-guided passive diffusion) posits that guanidinium side chains on the polypeptide form hydrogen bonds with cell surface phospholipids creating neutral ion pairs that passively diffuse across the plasma membrane (Rothbard et al., 2005, Adv Drug Deliv Rev. 57:495-504). The second model (endosomal release), asserts that endocytosis is a major portal through which cationic polypeptides and peptide mimetics enter the cell (Fischer, 2007, Med Res Rev. 27:755-795). Previous investigations have attempted to distinguish between these two models by blocking endocytosis, via thermal (Derossi et al., 1996, J Biochem. 271:18188-18193), pharmacologic (Wadia et al., 2004, Nat Med. 10:310-315; Fischer et al., 2004, J Biol Chem. 279:12625-12635), or genetic means (Ter-Avetisyan et al., 2008, J Biol Chem 284:3370-3378). The interpretation of these experiments is complicated, however, by differences in protein/polypeptide concentration and analytical method. For example, incubation of living cells with cationic proteins/polypeptides at concentrations ≥10 μM leads to the formation of nucleation zones (Duchardt et al., 2007, Traffic. 8:848-866) that transiently disrupt membranes (Palm-Apergi et al., 2009, FASEB J 23:214-223), causing the spontaneous release of peptide into the cytosol. Incubation of cells at lower concentrations (≤5 μM) of peptide, in the presence of drugs that inhibit endocytosis, prevents cytoplasmic access (Wadia et al., 2004, Nat Med. 10:310-315), implying that at low concentrations, the molecules studied cannot diffuse through the plasma membrane. Moreover, the many studies using microscopy to examine cells fixed by treatment with formaldehyde or methanol must be reevaluated in light of evidence that the fixation process can release fluorescently labeled peptides from endosomes (Belitsky et al., 2002, Bioorg Med Chem 10:3313-3318; Richard et al., 2003, J Biol Chem. 278:585-590), an artifact not observed during microscopic examination of living cells. Finally, the high-intensity light used during microscopy can itself facilitate the redistribution of fluorescently labeled peptides from endosomes to cytoplasm (Maiolo et al., 2004, J Am Chem Soc. 126:15376-15377). Unfortunately, most cationic peptides and proteins that engage the endocytic machinery remain trapped within vesicles where they are topologically separated from the cell interior and unable to access targets in the cytosol or nucleus (Erazo-Oliveras et al., 2012, Pharmaceuticals 5:1177-1209). Intracellular function, when observed, is believed to result from the mechanistically indistinct, unpredictable, and inefficient process of endosomal escape. Thus, whether, when, and how these cationic molecules escape endocytic vesicles to access the cytosol remain unanswered questions.

Attempts to identify structural determinants of cell permeability are complicated by the above experimental details as well as the fact that neither Tat (SEQ ID NO:67) nor Arg8 (SEQ ID NO:68) possesses a defined fold. Miniature proteins are a family of small (36-aa), well-folded polypeptides that adopt a characteristic hairpin fold consisting of axially packed α- and PPII helices (Blundell et al., 1981, Proc Natl Acad Sci USA. 78:4175-4179; Hodges and Schepartz, 2007, J Am Chem Soc. 129:11024-11025). Other small well-folded polypeptides include those with a zinc finger fold and others known as talens. Miniature proteins identified through both rational design (Zondlo et al., 1999, J Am Chem Soc. 121:6938-6939; Zellefrow et al., 2006, J Am Chem Soc. 128:16506-16507) and molecular evolution (Chin and Schepartz, 2001, Chem. Int. Ed. Engl. 40:3806-3809; Rutledge et al., 2003, J Am Chem Soc. 125:14336-14347; Golemi-Kotra et al., 2004, J Am Chem Soc. 126:4-5; Gemperli et al., 2005, J Am Chem Soc. 127:1596-1597) can modulate protein function by inhibiting protein interactions (Rutledge et al., 2003, J Am Chem Soc. 125:14336-14347; Gemperli et al., 2005, J Am Chem Soc. 127:1596-1597); both loss of function and gain of function activities have been observed (Golemi-Kotra et al., 2004, J Am Chem Soc. 126:4-5; Gemperli et al., 2005, J Am Chem Soc. 127:1596-1597; Zellefrow et al., 2006, J Am Chem Soc. 128:16506-16507). It has been reported previously that minimally cationic miniature proteins containing between 2 and 6 arginine residues embedded within the α- or PPII helix were taken up by mammalian cells in culture more efficiently than Tat (SEQ ID NO:67) or Arg8 (SEQ ID NO:68) (Daniels and Schepartz, 2007, J Am Chem Soc. 129:14578-14579; Smith et al., 2008, J Am Chem Soc. 130:2948-2949).

Despite advances made in the art, there remains a need in the art for improved peptides, proteins and fusion molecules capable of efficiently crossing biological membranes with low toxicity. The present invention fulfills this need.

SUMMARY OF THE INVENTION

The invention is based in part on the discovery that cationic modifications made to small proteins allow them to reach the cytosol of living cells. Thus, in one embodiment, the invention is a modified protein comprising at least 4 cationic residues, wherein the at least 4 cationic residues are displayed on at least 3 α-helical cationic faces. In some embodiments, the at least 4 cationic residues are selected from the group consisting of arginine and histidine. In some embodiments, the modified protein comprises at least 5 cationic residues, wherein the at least 5 cationic residues are displayed on at least 3 α-helical cationic faces. In some embodiments, the at least 5 cationic residues are selected from the group consisting of arginine and histidine. In some embodiments, the modified protein comprises an amino acid sequence selected from the group consisting of SEQ ID NOS: 10, 19, 25, 33, 35, 39, 41, 53, 65 and 70, or a variant thereof.

In another embodiment, the invention is a method of treating a disease or disorder in a subject in need thereof, the method comprising administering to the subject a therapeutically effective amount of a modified protein of the invention. In some embodiments, the subject is human.

In one embodiment, the invention is a modified protein fusion molecule comprising a modified protein domain (MPD) and a cargo domain, wherein the MPD comprises at least 4 cationic residues, wherein the at least 4 cationic residues are displayed on at least 3 α-helical cationic faces. In some embodiments, the at least 4 cationic residues are selected from the group consisting of arginine and histidine. In some embodiments, the MPD comprises at least 5 cationic residues, wherein the at least 5 cationic residues are displayed on at least 3 α-helical cationic faces. In some embodiments, the at least 5 cationic residues are selected from the group consisting of arginine and histidine. In some embodiments, the MPD comprises an amino acid sequence selected from the group consisting of SEQ ID NOS: 10, 19, 25, 33, 35, 39, 41, 53, 65 and 70. In some embodiments, the cargo domain comprises at least one selected from the group consisting of a small molecule, a nucleic acid and a polypeptide. In some embodiments, the modified protein fusion molecule further comprises a linker. In some embodiments, the modified protein fusion molecule further comprises a label.

In another embodiment, the invention is a method of treating a disease or disorder in a subject in need thereof, the method comprising administering to the subject a therapeutically effective amount of the modified protein fusion molecule of the invention. In some embodiments, the subject is human.

In one embodiment, the invention is a composition comprising a modified protein and a cargo molecule, wherein the modified protein comprises at least 4 cationic residues, wherein the at least 4 cationic residues are displayed on at least 3 α-helical cationic faces. In some embodiments, the at least 4 cationic residues are selected from the group consisting of arginine and histidine. In some embodiments, the modified protein comprises at least 5 cationic residues, wherein the at least 5 cationic residues are displayed on at least 3 α-helical cationic faces. In some embodiments, the at least 5 cationic residues are selected from the group consisting of arginine and histidine. In some embodiments, the modified protein comprises an amino acid sequence selected from the group consisting of SEQ ID NOS: 10, 19, 25, 33, 35, 39, 41, 53, 65 and 70. In some embodiments, the cargo molecule comprises at least one selected from the group consisting of a small molecule, a nucleic acid and a polypeptide. In some embodiments, the cargo molecule is not covalently bound to the modified protein.

In another embodiment, the invention is a method of treating a disease or disorder in a subject in need thereof, the method comprising administering to the subject a therapeutically effective amount of composition comprising a modified protein and a cargo molecule of the invention. In some embodiments, the subject is human.

In one embodiment, the invention is a method of determining whether a Dex-tagged molecule is able to reach the cytosol of a cell, the method including the steps of providing at least one cell, wherein the at least one cell comprises a Gal4-driven report gene and an artificial transcription factor comprising a glucocorticoid receptor ligand-binding domain variant (OR), a Gal4 DNA binding domain (Gal4), and a VP16 transactivation domain (VP16), contacting the at least one cell with a Dex-tagged molecule, and measuring the level of Gal4-driven reporter gene expression in the at least one cell contacted with the Dex-tagged molecule, wherein when the level of Gal4-driven reporter gene expression increases after the cell is contacted with the Dex-tagged molecule, the Dex-tagged molecule is determined to be able to reach the cytosol. In some embodiments, the glucocorticoid receptor ligand-binding domain variant (GR) comprises a cysteine-to-glycine substitution within the ligand-binding domain, at position 656 (C656G). In some embodiments, the reporter gene is eGFP. In some embodiments, the at least one cell s transiently transfected with a nucleic acid expressing the artificial transcription factor. In some embodiments, the at least one cell is stably transfected with a nucleic acid expressing the artificial transcription factor. In some embodiments, the at least one cell is transiently transfected with a nucleic acid expressing the Gal4-driven reporter gene. In some embodiments, the at least one cell is stably transfected with a nucleic acid expressing the Gal4-driven reporter gene. In some embodiments, the at least one cell is at least one selected from the group consisting of U2OS, HeLa, Saos-2, and HEK293T. In some embodiments, the Dex-tagged molecule is a Dex-tagged protein.

In another embodiment, the invention is a method of determining whether a Dex-tagged molecule is able to reach the cytosol of a cell, the method including the steps of providing at least one cell, wherein the at least one cell comprises a fusion protein comprising eGFP and a glucocorticoid receptor ligand-binding domain (GR) variant, measuring the level of eGFP in the cytosol of the at least one cell, measuring the level of eGFP in the nucleus of the at least one cell, determining the relative level of eGFP in the nucleus of the cell compared with the cytosol of the cell, contacting the at least one cell with a Dex-tagged molecule, measuring the level of eGFP in the cytosol of the at least one cell contacted with the Dex-tagged molecule, measuring the level of eGFP in the nucleus of the at least one cell contacted with the Dex-tagged molecule, determining the relative level of eGFP in the nucleus of the cell contacted with the Dex-tagged molecule compared with the cytosol of the cell contacted with the Dex-tagged molecule, wherein when the relative level of eGFP in the nucleus of the cell increases after the cell is contacted with the Dex-tagged molecule, the Dex-tagged molecule is determined to be able to reach the cytosol. In some embodiments, the glucocorticoid receptor ligand-binding domain (GR) variant comprises a cysteine-to-glycine substitution within the ligand-binding domain, at position 656 (C656G). In some embodiments, the at least one cell is transiently transfected with a nucleic acid expressing the fusion protein. In some embodiments, the at least one cell is stably transfected with a nucleic acid expressing the fusion protein. In some embodiments, the at least one cell is at least one selected from the group consisting of U2OS, HeLa, Saos-2, and HEK293T. In some embodiments, the Dex-tagged molecule is a Dex-tagged protein.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIGS. 1A-1C, depicts miniature protein design. (FIG. 1A) Sequences of cationic miniature proteins evaluated in the studies described herein. (FIG. 1B) A plot of the relationship between $\#R_{total}$ (the number of α-helical arginine residues) and $\#R_{faces}$ (the number of α-helical faces on which these arginines are displayed) for each aPP variant. The location of each α-helical arginine residue is represented by a filled circle on the helical wheel. (FIG. 1C) A plot of mean total cellular fluorescence at 530 nm of HeLa cells treated with fluorescently tagged miniature protein variants (5 μM, 30 min). (See also FIG. 8)

FIGS. 2A-2G, depicts the results of experiments demonstrating that arginine topology controls cell binding and uptake. (FIG. 2A) Surface binding of rhodamine labeled cationic miniature proteins in the absence of endocytosis and removal by trypsin treatment. HeLa cells were treated with 1 μM rhodamine labeled cationic miniature protein for 30 min. Cell were then treated with trypsin (0.05%, 10 min, 37° C.) or PBS before washing and analysis by flow cytometry. (FIG. 2B) Fraction of cell-associated fluorescence remaining after trypsin treatment. These data represent the ratio of black to gray bars shown in FIG. 2A. (FIG. 2C) Cell uptake of rhodamine labeled peptides by HeLa cells after 30 min and 90 min. (FIGS. 2D-2G) AlexaFluor-488-transferrin (Tf488) when added to HeLa cells (FIG. 2D) colocalizes with (FIG. 2E) Tf546 and (FIG. 2F) rhodamine labeled miniature proteins. Perfect colocalization is characterized by a Pearson's R value (R) equal to 1, while R values near 0 represent little or no colocalization. The correlation value observed when cells were treated with both Tf488 and alexa-fluor-546-labeled transferrin (Tf546) is 0.905. (FIG. 2G) When added with Tf488, rhodamine labeled aPP (aPPR) shows little intracellular signal. Rhodamine labeled cationic miniature proteins and Tf546 are shown, Tf488 is shown, and Hoescht (nucleus) is shown. For FIG. 2A and FIG. 2B, the amino acid sequence of Arg8 is provided in SEQ ID NO:68. Error bars shown represent mean ±SE. (See also FIG. 9)

FIGS. 3A-3D, depicts the results of experiments demonstrating translocation of GR-GFP after treatment with dexamethasone and certain dexamethasone labeled peptides but not aPPDex. (FIG. 3A) HeLa cells transfected with GR-GFP (which appears black in the top row) after no treatment (–), or treatment with 1 μM dexamethasone or 1 μM aPPDex for 30 min at 37° C. The lower panel is an overlay of the GFP signal, and the nuclear Hoescht signal. (FIG. 3B) Quantification scheme. (FIG. 3C) Quantification of the changes visible in FIG. 3D. ns, not significant. * p≤0.05, *** p≤0.001, ANOVA. (FIG. 3D) Visualization of the change in GR-GFP after treatment with 1 μM Dex-labeled cationic miniature protein for 30 min. For FIG. 3C and FIG. 3D, the amino acid sequence of Arg8 is provided in SEQ ID NO:68. (See also FIG. 10)

FIGS. 4A-4E, depicts the results of experiments demonstrating that endocytosis is required for cytosolic access. (FIG. 4A) Confocal microscopy images of HeLa cells treated with the indicated rhodamine- or AlexaFluor488-labeled peptide or miniature protein and various endocytosis inhibitors. (FIGS. 4B-4E) Translocation ratio after treatment of HeLa cells with 1 mM Dex, 5.3Dex (SEQ ID NO:33), TatDex (SEQ ID NO:36), Arg8Dex (SEQ ID NO:37), or aPPDex in the presence (black bars) or absence (gray bars) of various inhibitors of endocytosis, including 80 mM dynasore (FIG. 4B), 5 mM methyl-b-cyclodextrin (MbCD) (FIG. 4C), 50 mM EIPA (FIG. 4D), and 200 nM bafilomycin (FIG. 4E). *p%0.05; ***p % 0.001, ANOVA with Bonferroni post-test. Error bars shown represent mean ±SE. The amino acid sequence of Arg8 is provided in SEQ ID NO:68. (See also FIG. 11)

FIGS. 5A-5K, depicts the results of experiments demonstrating that miniature protein 5.3R enters via endocytosis into Rab5+ vesicles before trafficking to Rab7+ vesicles. HeLa cells transfected with the indicated GFP fusion protein (FIGS. 5A-5I) were treated with 1 μM 5.3R (FIGS. 5A-5C), TatR (FIGS. 5D-5F) or Arg8R (FIGS. 5G-5I) before being washed and imaged by confocal microscopy. Colocalization of 5.3R, TatR and Arg8R with Rab5-GFP is moderate (FIGS. 5A, 5D, 5G) but can be increased by arresting Rab5 maturation via overexpression of Rab5Q79L-GFP. (FIGS. 5B, 5E, 5H). 5.3R, TatR and Arg8R are delivered to Rab7+ endosomes (Figures 5C, 5F, 5I). (Figure 5J) Transfection with Rab5Q79L-GFP does not block the increase of translocation ratio seen after treatment with dexamethasone, 5.3Dex (SEQ ID NO:33), or Arg8Dex (SEQ ID NO:37), but decreases the translocation ratio measured after treatment with TatDex (SEQ ID NO:36) (p=0.005). (FIG. 5K) HeLa cells treated with 200 nM wortmannin for 30 min before treatment with 1 μM Dex, 5.3Dex (SEQ ID NO:33), TatDex (SEQ ID NO:36), Arg8Dex (SEQ ID NO:37), or aPPDex for 30 additional min in the continued presence of the drug. Wortmannin decreased the translocation ratio measured after treatment with TatDex (SEQ ID NO:36) (p=8.1×10$^{-15}$) and Arg8Dex (SEQ ID NO:37) (p=2.3×10$^{-5}$). Errors shown represent ±SE. ns, not significant; * p≤0.05;  p≤0.01; * p≤0.001, ANOVA with Bonferroni post test. For FIG. 5D-FIG. 5GF and FIG. 5J-FIG. 5K, the amino acid sequence of Arg8 is provided in SEQ ID NO:68. (See also FIG. 12)

FIGS. 6A-6D, depicts the results of experiments demonstrating that the 5.3 arginine motif is transportable into a zinc finger domain context. (FIG. 6A) Primary sequences of a generic zinc finger domain (ZF), an analogous domain in which all five arginines have been substituted with alanine (ZF5.3), and aPP5.3 (5.3). (FIG. 6B) Translocation ration observed after cells expressing GR-GFP were treated with 1 mM SDex or the indicated Dex-labeled molecule in the presence and absence of endocytic inhibitors, as described in FIG. 5. (FIG. 6C) Colocalization of Rab5-GFP with ZF5.3R and Hoescht 33342. (FIG. 6D) Rab5Q79L-GFP overexpression does not block the increase of translocation ratio seen after treatment with ZF 5.3Dex. Errors shown represent mean±standard error. ns, not significant. *** p≤0.001, ANOVA with Bonferroni post test. (See also FIG. 13)

FIGS. 8A-8C, depicts the results of circular dichroism (CD) analysis of miniature proteins studied herein. (FIG. 8A) Wavelength dependent CD spectra of miniature proteins at 25 μM concentration in PBS at 37° C. (FIG. 8B) Temperature dependent ellipticity at 222 nm of miniature proteins at 25 μM. (FIG. 8C) Calculated Tm of thermal melts shown in FIG. 8B.

FIGS. 10A-10L, depicts the results of validation of an assay to determine the cytosolic localization of Dex-labeled molecules by monitoring the nuclear to cytoplasmic ratio of a GR-GFP fusion protein. (FIG. 10A) Representative images of HeLa cells transfected with GR-GFP and treated with various concentrations of dexamethasone as indicated. Dotted outlines show regions defined as 'nucleus' and 'surround'. (FIGS. 10B-10G) Competition binding experiment in which various concentrations of aPP-Dex, 4.2Dex (SEQ ID NO:30), 5.2Dex (SEQ ID NO:32), 5.3Dex (SEQ ID NO:33), TatDex (SEQ ID NO:36), Arg8Dex (SEQ ID NO:37), or dexamethasone itself competes with Fluormone® (a fluorescently modified steroid) for binding to the GR. (FIGS. 10H-10L) Absence of degradation of cationic miniature proteins during incubation with HeLa cells. HeLa cells, treated for 30 min with 1 μM aPPR, 5.3R, TatR (SEQ ID NO:67), Arg8R (SEQ ID NO:68) or ZF5.3R were washed with PBS, lysed in RIPA buffer, and the lysates examined by HPLC. Traces of lysate from HeLa cells treated with aPPR, 5.3R, or ZF5.3R proteins are virtually identical to control samples spiked with miniature protein and do not show peaks the elute at the same time as rhodamine alone. By contrast, samples of cell lysate from HeLa cells treated with Arg8R (FIG. 10J) or TatR (FIG. 10K) show the appearance of numerous additional peaks, indicating modification of the peptide backbone. Cell lysate from untreated cells is shown for comparison, wherein a single peak due to light scatter from the detergent is present. For FIG. 10F and FIG. 10J, the amino acid sequence of Arg8 is provided in SEQ ID NO:68.

FIGS. 11A-11B, depicts the results of experiments demonstrating the absence of membrane permeabilization after treatment with Dex-labeled cationic miniature proteins and peptides. HeLa cells were incubated with 1 μM of the indicated dexamethasone labeled miniature protein or peptide in the presence of 200 nM Syto Orange (a cell permeable dye) and 200 nM Sytox Blue, a dye that is not cell permeable but binds to nuclear DNA when cell membranes are disrupted. Saponin (10 μg/mL) a detergent that permeabilizes mammalian cell membranes was used as a positive control. (FIG. 11A) Schema showing experimental design; cells with intact membranes exclude Sytox blue, cells with permeabilized membranes do not exclude Sytox blue. (FIG. 11B) Images of cells treated as described in FIG. 11A with aPPDex, 4.2Dex (SEQ ID NO:30), 4.3Dex (SEQ ID NO:31), 5.2Dex (SEQ ID NO:32), 5.3Dex (SEQ ID NO:33), TatDex (SEQ ID NO:36), and Arg8Dex (SEQ ID NO:37). The amino acid sequence of Arg8 is provided in SEQ ID NO:68. Very few show signal in the nucleus, indicating intact cell membranes.

FIGS. 12A-12C, depicts the results of demonstrating that cell permeable cationic modified proteins are not found within the Golgi. HeLa cells were transfected with galactosyltransferase (galT) tagged to GFP (galT-GFP) a marker of the Golgi, before plating in 96 well glass bottom plates and growth overnight. The media was replaced with HKR buffer containing (FIG. 12A) 1 μM 5.3R, (FIG. 12B) TatR or (FIG. 12C) Arg8R and incubated at 37° C. for 30 min, after which the cells were washed and imaged. No fluorescence (arrowheads) was found within Golgi areas. The fraction of rhodamine signal overlapping (RεG) within the golgi region (boxed) is low (less than 0.1). Selected vesicles showing fluorescence are indicated with white arrowheads. None overlap. Scale bars are 20 μm. For FIG. 12B, the amino acid sequence of Arg8 is provided in SEQ ID NO:68.

FIGS. 13A-13I, depicts the results of experiments demonstrating that cell permeable modified proteins 5.3 and ZF5.3 are found intact within the cytoplasm. (FIG. 13A) CD spectra of ZF and ZF5.3 in the presence and absence of Zn2+. (FIGS. 13B and 13C) Validation that treatment of HeLa cells with streptolysin O (SLO) leads to decreased membrane integrity, but not release of cytoplasmic vesicles. (FIG. 13B) HeLa cells were treated with SLO and stained with propidium iodide (PI), a marker of cells with permeabilized membranes. In a control sample only 7.6% of cells were PI+, whereas this number increased to 85% after treatment with SLO. (FIG. 13C) Treatment of HeLa cells with SLO does not release detectable levels of lysosomal enzymes into the cytosol. The activity of the lysosomal enzyme beta-hexosaminidase was monitored in the pellet and the supernatants of cells treated with or without SLO. The absorbance of 4-nitrophenol liberated from 4-nitrophenyl-N-acetyl-β-D-glucosaminide was measured at 405 nm. (FIGS. 13D-13I) HPLC analysis of aPPR, 5.3R, 5.2R, TatR, Arg8R, and ZF5.3R before or after treatment with cathepsin B, cathepsin D, cathepsin L, or isolated from cell cytoplasm by treatment with SLO. The trace obtained after injection of free rhodamine is shown for comparison. While little or no aPPR is observed in SLO extracts of HeLa cells (FIG. 13D), cytoplasmic extracts from HeLa cells treated with 5.3R (FIG. 13E) and ZF5.3R (FIG. 13I) show a single peak with the same retention time as the starting material. By contrast, HPLC traces from cytoplasmic extracts of cells treated with TatR (FIG. 13G) and Arg8R (FIG. 13H) show the recovery of little or no material with the same retention time as the starting material, indicating that the peptides present within the cytoplasm of these cells are modified. (FIGS. 13D-13F) Miniature proteins aPPR, 5.2R and 5.3R are each in vitro substrates for at least one of three cathepsins tested, suggesting that differences in cytoplasmic access do not depend on differences among these peptides acting as cathepsin substrates. Indeed, the products observed after treatment of 5.3R with cathepsin D are not seen in SLO extracts from cells treated with this peptide (FIG. 13E). For FIG. 13H, the amino acid sequence of Arg8 is provided in SEQ ID NO:68.

FIG. 15 depicts the results of experiments demonstrating that the rule of five motif results in high levels of cytosolic localization of peptides and small proteins, as determined by FCS. The amino acid sequence of Arg8 is provided in SEQ ID NO:68.

FIG. 22, comprising FIGS. 22A-22B, provides and an overview of GIGI and GIGT assays for monitoring cytosolic localization of Dex-tagged peptides and proteins. (FIG. 22A) GIGI: glucocorticoid-induced eGFP induction. Cells are transfected (transiently or stably) with plasmids pG5-eGFP and pGal4-GR★-VP16 and treated with the glucocorticoid receptor (GR) ligand dexamethasone (Dex) or a conjugate thereof to induce the transcription and subsequent translation of eGFP. Relative eGFP levels are assessed by fluorimetry of lysed cells or by microscopy or FACS analysis of living cells. (FIG. 22B) GIGT: glucocorticoid-induced eGFP translocation. Cells are transfected (transiently or stably) with pk7-GR★-GFP and treated with Dex or a conjugate thereof to induce the nuclear translocation of GR★-GFP. The nuclear to cytoplasmic ratio of living cells is determined using fluorescence microscopy and high content image analysis software such as CellProfiler or Acapella.

FIG. 23, comprising (FIG. 23A) GIGI in lysates: comparison of eGFP expression in U2OS, HeLa, and HEK293T cells transiently transfected with pGal4-GR-VP16, pG5-eGFP and pmCherry-N1 and treated with SDex or without (control). (FIG. 23B) GIGI in lysates: comparison of eGFP expression in lysates of cells transiently transfected with pG5-eGFP, pmCherry-N1, and either pGal4-GR-VP16 or pGal4-GR★-VP16, treated with varying concentrations of SDex. RFU values were calculated from individual wells using Equation 1 (see Experimental Examples) and are expressed±standard deviation (Excel). Curves shown represent the best fit of the data to Equation 2 (see Experimental Examples). (FIG. 23C) GIGI in living cells: live-cell imaging of eGFP expression in three transiently transfected cell lines. Cells were incubated in the presence or absence of 1 µM SDex for 24 h before imaging by epifluorescence microscopy. Nuclei were stained using Hoechst 33342. Scale bar=50 µm. (d) GIGI in living cells: quantification of eGFP expression by FACS analysis in transiently transfected HeLa, U2OS, and HEK293T cells treated for 24 h with 1 µM SDex. The mean cellular fluorescence for untreated (control) transfectants was set to 1, and other values are expressed as the fold-increase in fluorescence emission at 533 nm±standard deviation. For FIGS. 23A and 23D, statistical analysis was performed using a two-tailed Student's t test with each cell line treated as a separate population;  p≤0.005, * p≤0.001.

FIG. 24, comprising (FIG. 24A) GIGI in live cells: live-cell epifluorescent imaging of U2OS(GIGI) cells treated for 24 h with or without 1 µM SDex. Nuclei were stained with Hoechst 33342. Scale bar=20 µm. (FIG. 24B) GIGI in lysates: comparison of eGFP expression in lysates prepared from transiently transfected U2OS and U2OS (GIGI) cells treated with varying concentrations of SDex for 24 h. (FIG. 24C) GIGI in live cells: quantification of eGFP expression by FACS analysis in transiently transfected U2OS and U2OS(GIGI) cells treated for 24 h with or without 1 µM SDex. The mean cellular fluorescence for untreated (control) transfectants was set to 1, and other values are expressed as the fold-increase in fluorescence emission at 533 nm standard deviation. (FIG. 24D) GIGI in lysates: relative eGFP expression levels in U2OS(GIGI) cells treated with 1 µM of the indicated Dex-tagged miniature protein or peptide. (FIG. 24E) GIGI in lysates: concentration-dependent effect of each miniature protein on eGFP expression in U2OS(GIGI) cells. EC50 values are shown in Table 4. (FIG. 24F) GIGI in lysates: well-to-well variability of GIGI in U2OS(GIGI) cells treated with 1 µM 5.3Dex or without (control). Randomized RFU values were then plotted as a function of sample number; n=150. Solid lines represent mean RFUs for treated or untreated cells. Dashed lines represent the mean value±3 times the standard deviation (Excel). The Z'-factor38 was calculated using Equation 3 (see Experimental Examples).

FIG. 25, comprising FIGS. 25A-25D, depicts the results of experiments performed for the validation of the GIGT assay in transiently transfected cells. (FIG. 25A) Images of HeLa and U2OS cells transiently transfected with GRGFP or GR★-GFP with or without treatment with 100 nM SDex for 30 min. Images show an overlay of GFP signal and Hoechst 33342. (FIG. 25B) Comparison of GR-GFP and GR★-GFP nuclear translocation values across varying SDex concentrations after 30 min of treatment. TRs, expressed±standard deviation, were calculated using CellProfiler as previously reported, and curves represent best fit of the data shown in Equation 2 (see Experimental Examples). (FIG. 25C) Analysis of GR★-GFP nuclear translocation in live HeLa cells with or without treatment with 500 nM SDex or Dex-labeled peptides for 30 min. *** p≤0.001, ANOVA. (FIG. 25D) Images of live HeLa cells treated with 500 nM Dex-tagged peptides for 30 min. For FIG. 25C and FIG. 25D, the amino acid sequence of Arg8 is provided in SEQ ID NO:68.

FIG. 26, comprising (FIG. 26A) Images of Saos-2(GIGT) cells stably transfected with GR★-GFP with or without treatment with 1 µM SDex for 30 min. Left images show an overlay of GFP signal with Hoechst 33342 and right images display GFP signal. (FIG. 26B) Effect of SDex on the calculated TR in HeLa cells transiently transfected with GR★-GFP and stable Saos-2(GIGT) cells. (FIG. 26C) Analysis of GR★-GFP nuclear translocation in Saos-2 (GIGT) cells after a 30 min treatment with 1 µM SDex or Dex-labeled peptides. TRs, expressed±standard deviation, were calculated using Acapella. *** p≤0.001; ANOVA. (FIG. 26D) Well-to-well variability of GIGT in Saos-2 (GIGT) cells treated for 30 min with 1 µM 5.3Dex (SEQ ID NO:33) or without (control). TR values calculated described were randomized and plotted as a function of sample number; n=50. Solid lines represent mean TRs for treated or untreated cells. Dashed lines represent mean value±3 times the standard deviation (Excel). The Z'-factor38 was calculated using Equation 3 (see Experimental Procedures). For FIG. 26C, the amino acid sequence of Arg8 is provided in SEQ ID NO:68.

FIG. 27, comprising FIGS. 27A-27F, depicts the analysis of natural and engineered ZF domains using GIGI and GIGT. (FIG. 27A) Primary sequences of zinc finger domains evaluated herein. (FIG. 27B) Helical wheel diagrams of each ZF domain illustrating the relative location of each α-helical arginine residue, which is represented as a filled circle. (FIG. 27C) GIGI in cell lysates: concentration-dependent effect of each Dex-labeled ZF domain on eGFP expression in U2OS (GIGI) cells after 24 h of treatment. EC50 values are shown in Table 3. RFUs, expressed±standard deviation, were calculated and curve fits performed as described (see Experimental Examples). (FIG. 27D) Analysis of GR★-GFP nuclear translocation in transiently transfected HeLa cells treated with or without 500 nM SDex or Dex-labeled ZF proteins for 30 min. TRs, expressed±standard deviation, were calculated using CellProfiler as previously reported. * p≤0.05; *** p≤0.001; ns, not significant, ANOVA. (FIG. 27E) GIGI in cell lysates. Well-to-well variability of GIGI in U2OS(GIGI) cells treated for 24 h with or without (control) 1 µM ZF5.3Dex. RFU values were calculated as described above, randomized, and plotted as a function of sample number; n=150. Solid lines represent mean RFUs for treated or untreated cells. Dashed lines represent the mean value±3 times the standard deviation. (FIG. 27F) Well-to-well variability of GIGT in Saos-2(GIGT) cells treated for 30 min with or without (control) 1 µM ZF5.3Dex. TR values were calculated using Acapella image analysis software as described and plotted as a function of sample number; n=48. Solid lines represent mean TRs for treated or untreated cells. Dashed lines represent the mean value±3 times the standard deviation. Z'-factors were calculated using Equation 3 (see Experimental Examples).

Figure 32:
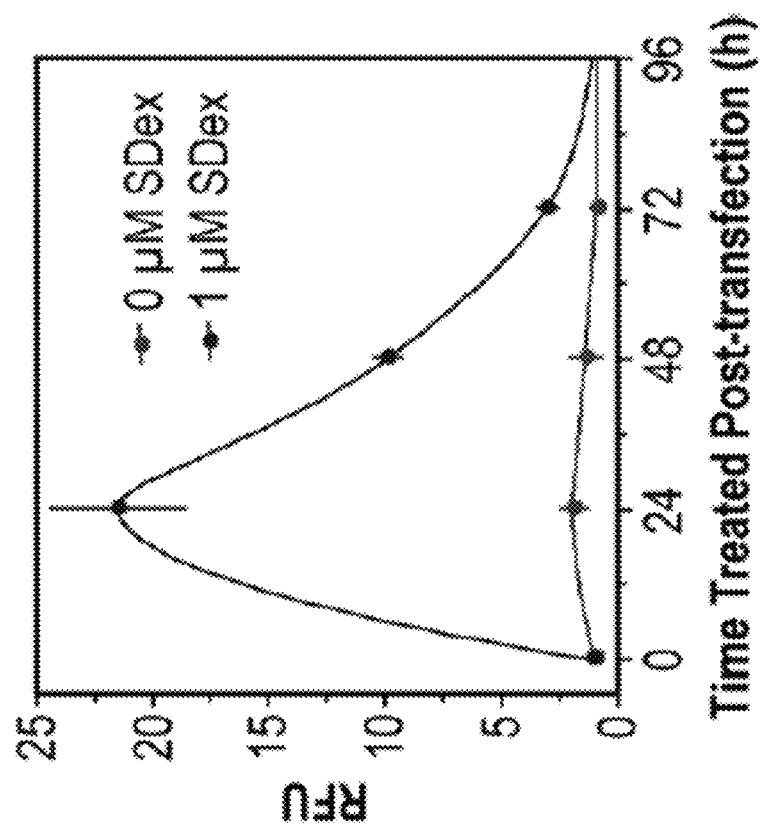

FIG. 32 depicts the results of experiments showing that the GIGI assay is time-sensitive in transiently transfected cells. HEK293T cells were transiently transfected with GIGI component plasmids as described and were allowed to incubate for 24, 48 or 72 h before treatment. Following incubation the cells were treated with or without 1 mM SDex for 24 h before lysis and analysis as described in the main text.

Figure 33:
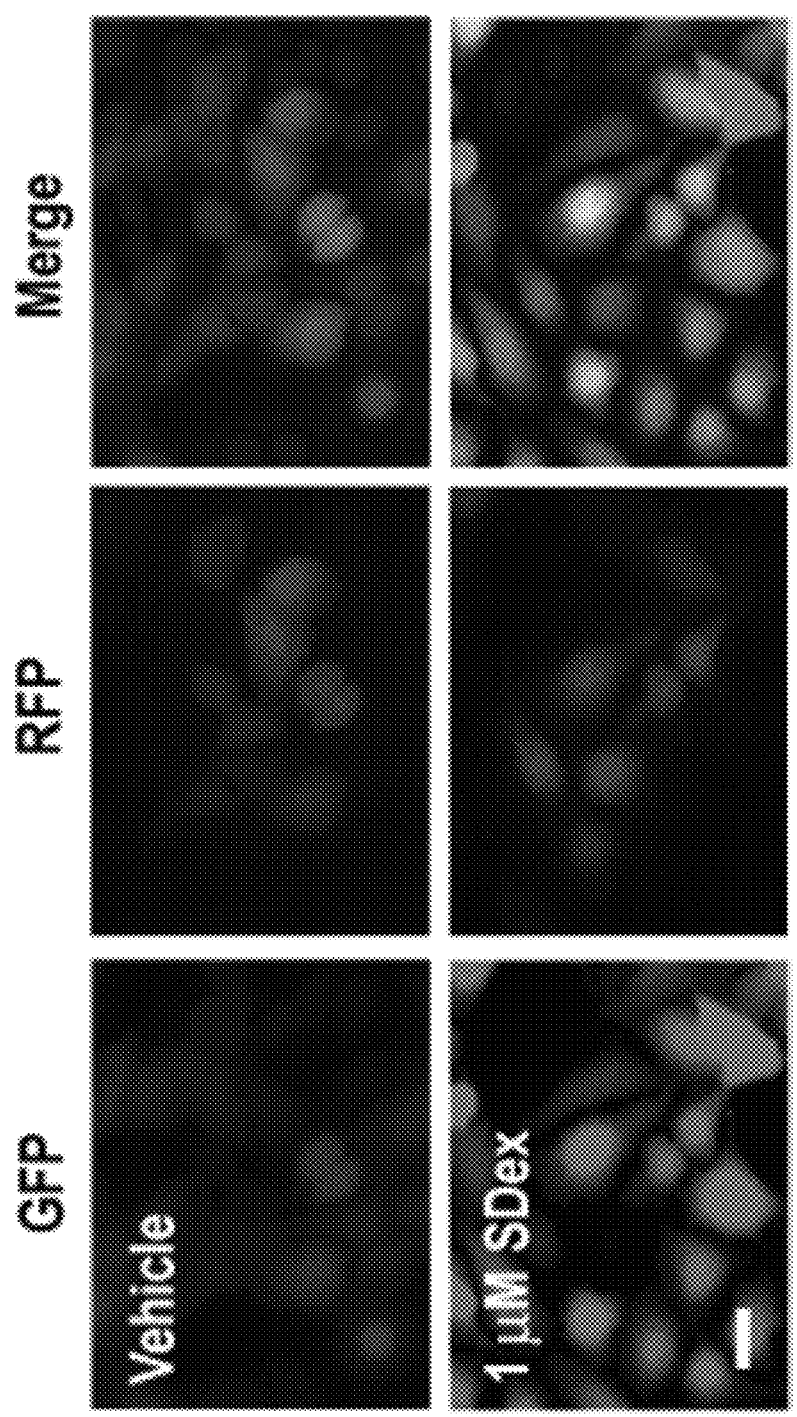

FIG. 33 depicts the results of experiments demonstrating the development of stable U2OS(GIGI) cells. Low-passage U2OS cells (ATCC #HTB-96) were transfected in Opti-MEM reduced serum media (Life Technologies, #31985-070) with 0.667 mg/ml pG5-eGFP and 0.1667 mg/ml pGal4-GRH-VP16 plasmids complexed with Lipofectamine 2000 (Invitrogen). Cells were allowed to transfect for 18 h at 37° C. under 5% CO2. Stable transfectants were selected with McCoy's 5A media supplemented with 10% FBS, pen/strep and 500 mg/mL G418 for 21 days, replenishing media every three days. Isolated colonies were collected using sterile 3 mm cloning disks (Scienceware, #Z374431) soaked in 0.25% trypsin—EDTA. Stable clones were identified using GIGI lysis assays. To provide an internal normalization control for lysis experiments, U2OS(eGFP) cells were stably transfected in Opti-MEM reduced serum media (Life Technologies, #31985-070) with 0.333 mg/ml pmCherry-N1 complexed with Lipofectamine 2000 (Invitrogen). Cells were allowed to transfect for 18 h at 37° C. under 5% CO2. Stable transfectants were selected with McCoy's 5A media supplemented with 10% FBS, pen/strep and 500 mg/mL G418 for 14 days, replenishing media every three days. Transfected colonies were identified by fluorescence microscopy, isolated from the population and sorted multiple times on a FACS Vantage cell sorter to enrich the brightest cells. Robust GIGI response to 1 mM SDex and expression of mCherry was confirmed in the final cell population, dubbed U2OS(GIGI), by epifluorescence microscopy. Scale bar: 20 mm.

Figure 34:
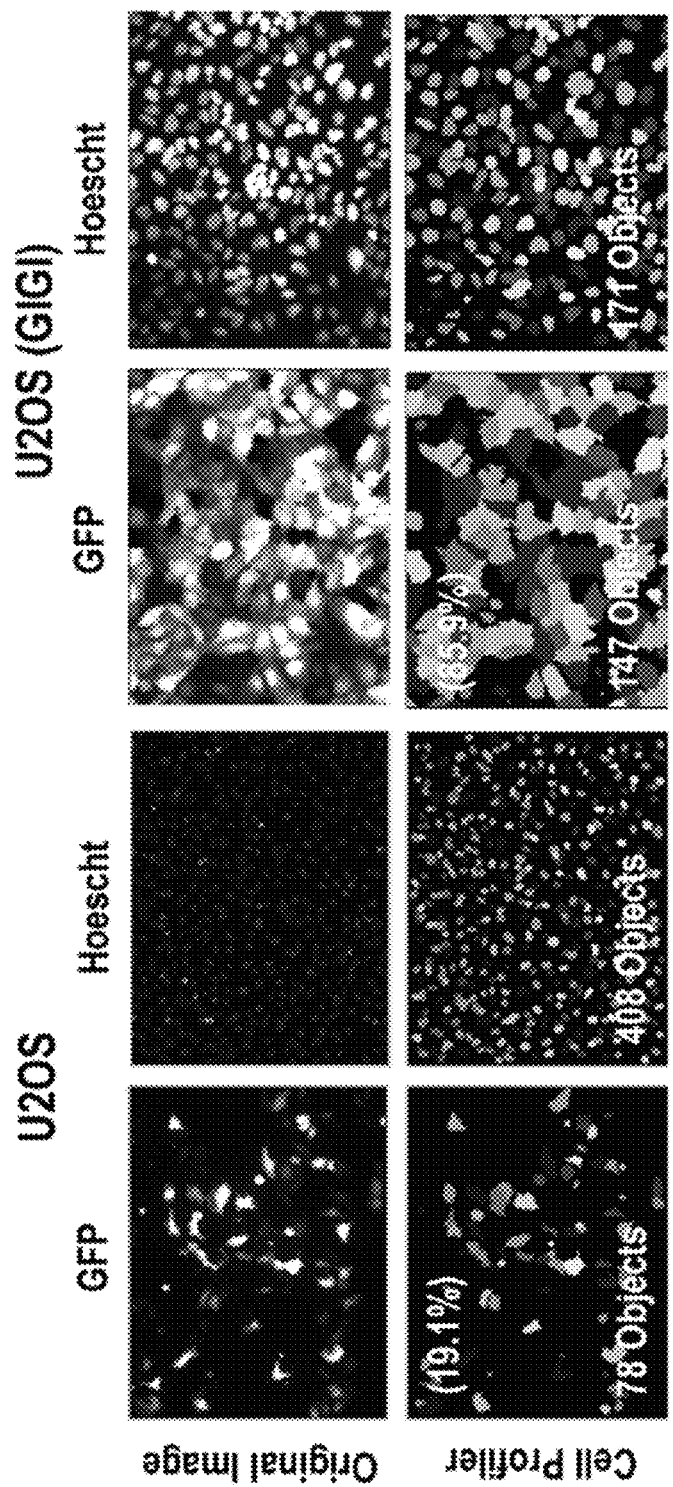

FIG. 34 depicts the results of experiments showing that eGFP expression is more robust in stably transfected cell lines following treatment with SDex. U2OS cells were transiently transfected with GIGI component plasmids. Following transfection, the cells were treated with 1 mM SDex for 24 h and 1 mg/mL Hoechst 33342 and imaged by fluorescence microscopy. U2OS(GIGI) cells were similarly treated with 1 mM SDex for 24 h and 1 mg/mL Hoechst 33342 and imaged. Raw images were processed using CellProfiler. Top row shows images of cells visualized to detect GFP and Hoechst 33342. Bottom row shows 'object' images generated by CellProfiler from the images from the top row. Excitation and emission wavelengths for imaging eGFP were set at 470 and 509 nm respectively. Excitation and emission wavelengths for imaging Hoechst were set at 359 nm and 461 nm respectively. Transfection efficiencies (shown as percentages, Table 2) were obtained by dividing the number of objects counted in the GFP channel by the number of objects counted in the Hoechst channel.

Figure 35:
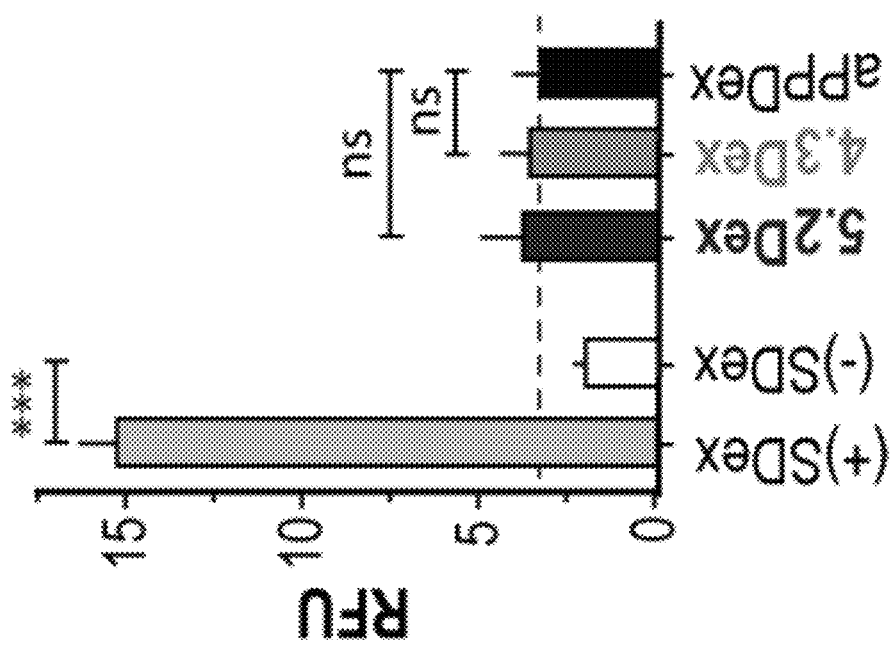

FIG. 35 depicts the results of experiments showing that Dex-labeled miniature proteins 4.3Dex and 5.2Dex do not induce eGFP expression in transiently transfected HeLa cells. HeLa cells transiently transfected with GIGI component plasmids were treated for 24 h with or without 1 mM of the indicated Dex-tagged miniature protein. Relative fluorescence units (RFU) were calculated from individual wells using Equation 1. All RFUs are expressed±standard deviation (Excel). Statistical analysis was performed using a two-tailed Student's t-test; *** p≤0.001; ns, not significant.

Figure 36:
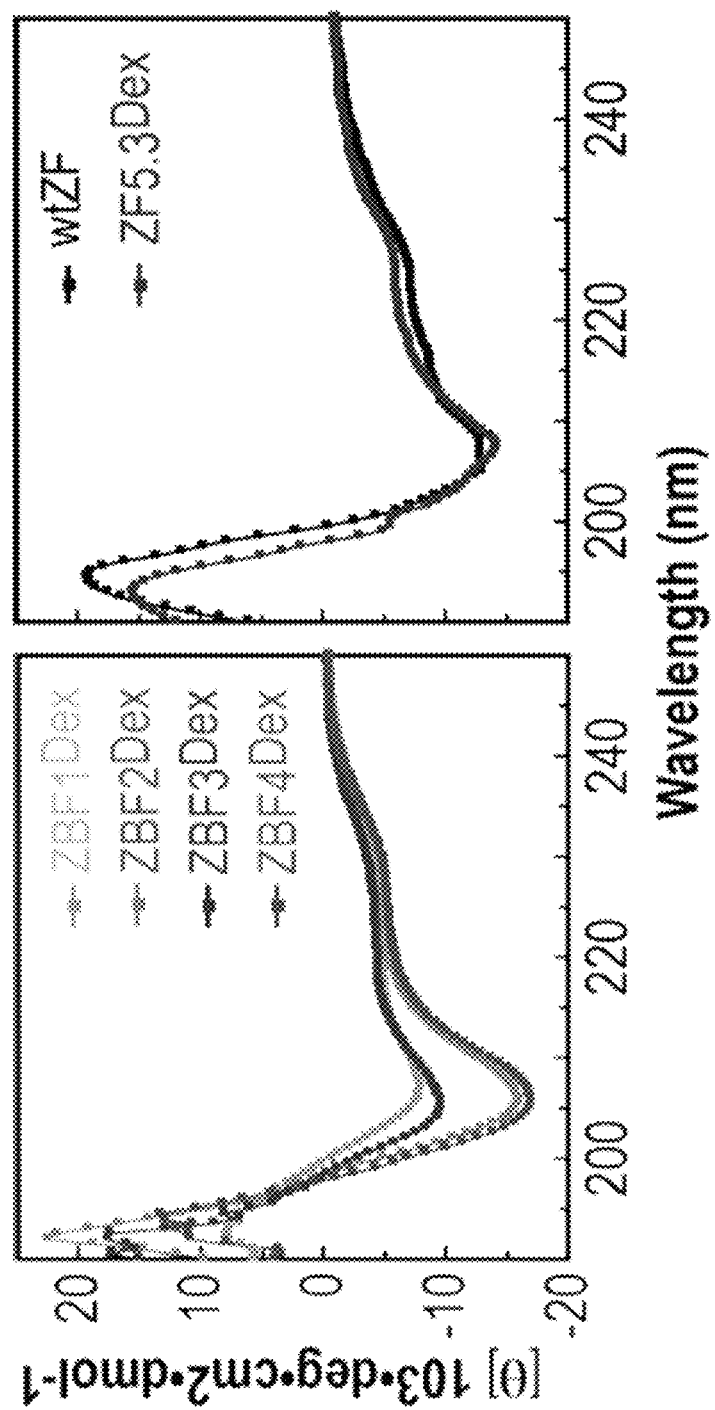

FIG. 36 depicts the results of experiments showing that Dex-labeled zincfinger domains retain secondary structure in solution as measured by wavelength-dependent circular dichroism spectroscopy. Samples were prepared by dissolving peptides to a final concentration of 25 mM in argon purged 10 mM Tris buffer (pH 7.4) in the presence of 50 mM ZnC12. Samples were incubated at room temperature for 30 minutes and spectra were recorded at 25° C. on a Jasco J-810-150S spectropolarimeter. Plots show background-subtracted average of six scans.

DETAILED DESCRIPTION OF THE INVENTION

The present invention is based on the discovery that cationic modifications made to small proteins allow them to reach the cytosol of living cells. Certain embodiments of the invention are generally related to small proteins, such as miniature proteins, including avian pancreatic polypeptide (aPP), modified so that the small proteins reach the cytosol. In some embodiments, the modified protein molecules deliver an associated cargo molecule to the cytosol. Other embodiments of the invention relate to modified protein fusion molecules that reach the cytosol. In various embodiments, the modified proteins, and fusion molecules thereof, have additional functions, such as the ability to bind to other molecules. Still other embodiments of the invention are generally directed to methods of making such modified proteins and fusions thereof, methods of using such modified proteins and fusions thereof, and kits comprising such modified proteins, and fusions thereof.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, or ±5%, or ±1%, or ±0.1% from the specified value, as such variations are appropriate to perform the disclosed methods.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "housekeeping gene" as used herein refers to genes that are generally always expressed and thought to be involved in routine cellular metabolism. Housekeeping genes are well known and include such genes as glyceraldehyde-3-phosphate dehydrogenase (G3PDH or GAPDH), albumin, actins, tubulins, cyclophilin, hypoxanthine phsophoribosyltransferase (HRPT), 28S, and 18S rRNAs and the like.

"Instructional material," as that term is used herein, includes a publication, a recording, a diagram, or any other medium of expression which can be used to communicate the usefulness of the nucleic acid, polypeptide, peptide, and/or compound of the invention in the kit for identifying, diagnosing or alleviating or treating the various diseases or disorders recited herein. Optionally, or alternately, the instructional material may describe one or more methods of identifying, diagnosing or alleviating the diseases or disorders in a cell or a tissue of a subject. The instructional material of the kit may, for example, be affixed to a container that contains the nucleic acid, peptide, and/or compound of the invention or be shipped together with a container that contains the nucleic acid, peptide, and/or compound. Alternatively, the instructional material may be shipped separately from the container with the intention that the recipient uses the instructional material and the compound cooperatively.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "label" when used herein refers to a detectable compound or composition that is conjugated directly or indirectly to a molecule to generate a "labeled" molecule. The label may be detectable by itself (e.g. radioisotope labels or fluorescent labels) or, in the case of an enzymatic label, may catalyze chemical alteration of a substrate compound or composition that is detectable (e.g., avidin-biotin).

By the term "modulating," as used herein, is meant mediating a detectable increase or decrease in the level of a mRNA, polypeptide, or a response in a subject, or a cell or tissue of a subject, as compared with the level of a mRNA, polypeptide or a response in the subject, or a cell or tissue of the subject, in the absence of a treatment or compound, and/or compared with the level of a mRNA, polypeptide, or a response in an otherwise identical but untreated subject, or cell or tissue of the subject. The term encompasses perturbing and/or affecting a native signal or response thereby mediating a beneficial therapeutic response in a subject, preferably, a human.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this disclosure. It will be understood that when a nucleotide sequence is represented herein by a DNA sequence (e.g., A, T, G, and C), this also includes the corresponding RNA sequence (e.g., A, U, G, C) in which "U" replaces "T".

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

The term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

As used herein, the terms "therapy" or "therapeutic regimen" refer to those activities taken to alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more drugs or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

As used herein, the term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention generally relates to modified proteins, and modified protein fusion molecules, that efficiently reach the cytosol of living cells. Certain embodiments of the invention are generally related to modified proteins, such as miniature proteins, including avian pancreatic polypeptide (aPP), modified such that the proteins efficiently reach the cytosol of living cells. For instance, a portion of the aPP, such as the alpha helix region, may be modified to render the region substantially cationic. As an example, one or more residues may be substituted with cationic amino acid residues such as arginine.

The modified proteins and fusion molecules of the invention may also have additional functions, such as the ability to bind to other proteins. In certain embodiments, the modified protein molecules deliver an associated cargo molecule to the cytosol. Still other embodiments of the invention are generally directed to methods of making such modified proteins, methods of using such modified proteins, kits involving such modified proteins, and the like.

Compositions

Various embodiments of the invention are generally directed to various modified proteins that have been modified so that the proteins efficiently reach the cytosol of living cells. For example, the modified proteins may be modified at one or more regions in a manner that causes the regions to become substantially cationic. One or more residues of a protein may be substituted with, for example, cationic amino acid residues. Non-limiting examples of cationic amino acid residues include arginine or histidine. As used herein throughout, the terms "miniature protein" or "miniprotein" refer to a relatively small protein containing at least a protein scaffold and one or more additional domains or regions that help to stabilize its tertiary structure, but the proteins, and fusions thereof, of the invention are not limited to miniature proteins. In some cases, the protein may have a length of no more than 40 or 45 residues. For instance, in various embodiments, the miniature protein may have a length of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more residues.

In some embodiments, the modified protein of the invention comprises at least 4 cationic amino acid residues, such as arginine, wherein the at least 4 cationic residues are displayed on at least 3 α-helical faces. In other embodiments, the modified protein of the invention comprises at least 5 cationic amino acid residues, such as arginine, wherein the at least 5 cationic residues are displayed on at least 3 α-helical faces. In various embodiments, the modified protein of the invention comprises at least one selected from the group consisting of SEQ ID NOS: 10, 19, 25, 33, 35, 39, 41, 53, 65 and 70.

In some cases, a modified protein of the invention may be identified as one that efficiently reaches the cytosol of living cells by exposing a cell to a modified protein and comparing the concentration of the modified protein within the cell after equilibration (e.g., when a steady-state concentration is reached) to the concentration of an unmodified protein exposed to the cell under the same conditions. A cell permeable protein, or fusion thereof, of the invention has a greater ability to reach the cytosol of the cell, e.g., it can reach the cytosol of the cell at a greater concentration than an unmodified protein under the same conditions. In some cases, the concentration of the modified protein within the cytosol of the cell reaches a level that is greater than the concentration of an unmodified protein by at least about 2 times, at least about 5 times, at least about 10 times, or at least about 50 times. For example, for a modified aPP as used herein, cells may be exposed to a concentration of 1 micromolar of protein (modified and unmodified), and the concentrations of each within the cell may be determined in some fashion. As a specific example, the proteins may be labeled with a fluorescent entity, such as fluorescein, and their relative concentrations determined using techniques such as fluorescence correlation spectroscopy, using routine techniques known to those of ordinary skill in the art.

Non-limiting examples of miniature proteins include the PP fold protein scaffolds, which generally contain thirty-six amino acids and are the smallest known globular proteins. Despite their small size, PP fold proteins are stable and remain folded under physiological conditions. Some PP fold protein scaffolds of the invention comprise two anti-parallel helices, an N-terminal type II polyproline helix (PPII) and an alpha helix. The stability of the PP fold protein scaffolds of the invention derives predominantly from interactions between hydrophobic residues on the interior face of the alpha helix and the residues on the two edges of the polyproline helix.

Positions for grafting these binding site residues on the protein scaffold include, but are not limited to, positions on the solvent-exposed alpha-helical face of aPP. Substitutions of binding site residues may be made, in some cases, for residues involved in stabilizing the tertiary structure of the modified protein. As used herein, the term "exposed on the alpha helix domain" means that an amino acid substituted into aPP is available for association or interaction with another molecule and is not otherwise bound to or associated with another amino acid residue on the aPP. This term is used interchangeably with the term "solvent-exposed alpha helical face" and similar terms (e.g., "solvent-exposed face of the aPP alpha helix").

Members of the PP fold family of protein scaffolds which are contemplated for use in the present invention include, but are not limited to, avian pancreatic polypeptide (aPP), Neuropeptide Y, lower intestinal hormone polypeptide and pancreatic peptide YY (PYY). In one embodiment, the protein scaffold comprises the PP fold protein, avian pancreatic polypeptide (aPP). aPP is a PP fold polypeptide characterized by a short (eight residue) amino-terminal type II polyproline helix linked through a type I beta turn to an eighteen residue alpha helix. Because of its small size and stability, aPP is an excellent protein scaffold for, e.g., protein grafting of alpha-helical recognition epitopes.

The natural sequence of aPP is as shown in FIG. 1A. However, in some cases, the aPP may be modified by the addition of a terminal C, as is shown in SEQ ID NO: 3. The C may be added to the end of aPP to facilitate the binding of other species to aPP, for example, a reporter species such as fluorescein, as is shown in SEQ ID NO: 12, for aPP-Flu. Similarly, any other modified protein or peptide discussed herein may be modified by the addition of a terminal C or a terminal Y (if one is not already present), e.g., to facilitate binding.

One embodiment of the invention is generally directed to miniature proteins, such as avian pancreatic polypeptide (aPP), that include an alpha helix region that is modified by the substitution and/or addition of various amino acid residues with cationic amino acid residues such as arginine or histidine. The modified aPP may also include other substitutions, e.g., for improving binding properties.

Cationic properties can be determined, for instance, by using charge electrophoresis or isoelectric focusing to determine the charge of the protein (or portions of the protein) under various conditions. Any number of residues within the alpha helix region may be substituted with arginine residues or the like, for instance, at least two residues, at least three residues, at least four residues, at least five residues, etc. In some cases, there may be between 3 and 6 or between 3 and 5 residues (inclusively) that are substituted with a cationic amino acid residue, such as arginine. The substitutions may be present on any location within the alpha helix region, and may be consecutive or non-consecutive, in some cases.

Still other non-limiting examples include the modification of proteins of the invention to be able to bind to (or otherwise interact with) other proteins. It should be noted that such binding may be specific or non-specific, and involve various noncovalent interactions such as including hydrogen bonding, metal coordination, hydrophobic forces, van der Waals forces, pi-pi interactions, and/or electrostatic effects.

Another set of embodiments is directed to a miniature protein, such as aPP, that includes an alpha helix region modified by the substitution and/or addition of various amino acid residues with cationic amino acid residues. A non-limiting example of a cationic amino acid residue is arginine. The residues chosen for substitution may be present anywhere within the alpha helix region, and may be independently consecutive or non-consecutive.

In one embodiment, the residues chosen for substitution may be ones that are located on one portion or side or face of the alpha helix. For instance, the residues to be substituted may be chosen from the ones located on one side of the alpha helix, e.g., on an exterior side or a solvent-exposed face of the alpha helix when the protein is properly folded. Without wishing to be bound by any theory, it is believed that such substitutions can cause the exterior side of the modified protein to appear positively charged or cationic, to facilitate permeation of the modified protein into the cytosol of cells.

In some embodiments, the modified proteins of the invention are able to associate with (or bind to) specific sequences of DNA or other proteins. These proteins may be able to bind, for example, to DNA or other proteins with high affinity and selectivity. As used herein, the term "bind" or "binding" refers to the specific association or other specific interaction between two molecular species, such as, but not limited to, protein-DNA interactions and protein-protein interactions, for example, the specific association between proteins and their DNA targets, receptors and their ligands, enzymes and their substrates, etc. Such binding may be specific or non-specific, and can involve various noncovalent interactions such as including hydrogen bonding, metal coordination, hydrophobic forces, van der Waals forces, pi-pi interactions, and/or electrostatic effects. It is contemplated that such association may be mediated through specific sites on each of two (or more) interacting molecular species. Binding can be mediated by structural and/or energetic components. In some cases, the latter will comprise the interaction of molecules with opposite charges.

In one set of embodiments, the invention involves a technique known as protein grafting. Protein grafting has generally been described, for example, in U.S. patent application Ser. No. 09/840,085, filed Apr. 24, 2001, entitled "Modified Avian Pancreatic Polypeptide Miniature Binding Proteins," by A. Shepartz Shrader, et al, now U.S. Pat. No. 7,297,762, issued Nov. 20, 2007, incorporated herein by reference. Briefly, protein grafting identifies binding site residues from a globular protein that is able to participate in binding-type associations between that protein and its specific binding partners, then the residues are grafted onto a small but stable protein scaffold. As used herein, the term "binding site" refers to the reactive region or domain of a molecule that directly participate in its specific binding with another molecule. For example, when referring to the binding site on a protein or nucleic acid, binding occurs as a result of the presence of specific amino acids or nucleotide sequence, respectively, that interact with the other molecule. Examples of protein scaffolds of the invention comprise members of the pancreatic fold (PP fold) protein family, particularly avian pancreatic polypeptide (aPP).

Thus, in one embodiment, a modified protein may be able to associate with or bind to a specific sequence of DNA. In some embodiments, the DNA sequence may comprise sites for known proteins that bind to that specific DNA sequence (contemplated known proteins would be, e.g., a promotor or regulator). For example, in the design of a DNA-binding protein, the amino acid residues of a known protein that participate in binding or other association of the protein to that particular DNA sequence are identified.

Generally, it is contemplated that any potential binding site on a DNA sequence can be targeted using the DNA binding proteins of the invention. Certain embodiments include proteins having helical structures which bind to a DNA binding site. In some embodiments, the binding involves a basic region leucine zipper (bZIP) structure, while in other embodiments the structure involves a basic-helix-loop-helix (bHLH) structure. In another embodiment, the binding involves a structure like those found in homeodomain proteins. Example bZIP structures include, but are not limited to, those found in GCN4 and C/EBP-delta, and example bHLH structures include, but are not limited to, those found in Max, Myc and MyoD. Example homeodomain structures include, but are not limited to, those found in the Q50 engrailed variant protein.

The cell permeability of the modified protein may be determined, for example, as previously described. Thus, for example, cells may be exposed to a concentration of 1 micromolar of modified protein, and the concentrations of each within the cell, or the cytosol of the cell, may be determined in some fashion. For example, the protein may be labeled with a fluorescent entity, such as fluorescein, and the relative concentrations determined using techniques described elsewhere herein. In some embodiments, a protein of the present invention is produced and selected using a phage display method. In such a method, display of recombinant proteins on the surface of viruses which infect bacteria (bacteriophage or phage) make it possible to produce soluble, recombinant proteins having a wide range of affinities and kinetic characteristics.

To display the proteins on the surface of phage, a synthetic gene encoding the protein is inserted into the gene encoding a phage surface protein (pIII) and the recombinant fusion protein is expressed on the phage surface. Variability may be introduced into the phage display library to select for proteins which not only maintain their tertiary, helical structure but which also display increased affinity for a preselected target because the critical (or contributing but not critical) binding residues are optimally positioned on the helical structure.

Since the recombinant proteins on the surface of the phage are functional, phage bearing proteins that bind with high-affinity to a particular target DNA or protein can be separated from non-binding or lower affinity phage by using techniques such as antigen affinity chromatography. Mixtures of phage are allowed to bind to the affinity matrix, non-binding or lower affinity phage are removed by washing, and bound phage are eluted by treatment with acid or alkali. Depending on the affinity of the protein for its target, enrichment factors of twenty-fold to a million-fold are obtained by a single round of affinity selection. By infecting bacteria with the eluted phage, however, more phage can be grown and subjected to another round of selection. In this way, an enrichment of a thousand-fold in one round becomes a million-fold in two rounds of selection. Thus, even when enrichments in each round are low, multiple rounds of affinity selection leads to the isolation of rare phage and the genetic material contained within which encodes the sequence of the domain or motif of the recombinant protein that binds or otherwise specifically associates with it binding target.

Accordingly, in various embodiments of the invention, the methods disclosed herein are used to produce a phage expression library encoding proteins capable of binding to a DNA or to a protein that has already been selected using the protein grafting procedure described above. In such embodiments, phage display can be used to identify proteins that display an even higher affinity for a particular target DNA or protein than that of the proteins produced without the aid of phage display. In yet another embodiment, the invention encompasses a universal phage display library that can be designed to display a combinatorial set of epitopes or binding sequences to permit the recognition of nucleic acids, proteins or small molecules by a protein without prior knowledge of the natural epitope or specific binding residues or motifs natively used for recognition and association.

Various structural modifications also are contemplated for the present invention that, for example, include the addition of restriction enzyme recognition sites into the polynucleotide sequence encoding the modified protein that enable genetic manipulation of these gene sequences. Accordingly, the re-engineered modified proteins can be ligated, for example, into an M13-derived bacteriophage cloning vector that permits expression of a fusion protein on the phage surface. These methods allow for selecting phage clones encoding fusion proteins that bind a target ligand and can be completed in a rapid manner allowing for high-throughput screening of proteins to identify the protein with the highest affinity and selectivity for a particular target.

According to the methods of the invention, a library of phage displaying modified proteins is incubated with the immobilized target DNA or proteins to select phage clones encoding proteins that specifically bind to or otherwise specifically associate with the immobilized DNA or protein. This procedure involves immobilizing an oligonucleotide or polypeptide sample on a solid substrate. The bound phage are then dissociated from the immobilized oligonucleotide or polypeptide and amplified by growth in bacterial host cells. Individual viral plaques, each expressing a different recombinant protein, are expanded to produce amounts of protein sufficient to perform a binding assay. The DNA encoding this recombinant binding protein can be subsequently modified for ligation into a eukaryotic protein expression vector. The modified protein, adapted for expression in eukaryotic cells, is ligated into a eukaryotic protein expression vector.

In another embodiment, the invention encompasses proteins that bind to other proteins and methods for making these proteins. The binding of the proteins modulates protein-protein and/or protein-ligand interactions. Thus, in some embodiments the binding blocks the association (or specific binding) of ligands and receptors. The ligand can be either another protein but also can be any other type of molecule such as a chemical substrate. In one embodiment of the present invention, making the protein-binding protein of the invention involves determining the amino acid residues which are essential to binding of the ligand protein to its target receptor protein. In some embodiments, these essential residues are identified using three-dimensional models of a protein or protein complex which binds to or interacts with another protein based on crystallographic studies while in other embodiments they are identified by studies of deletion or substitution mutants of the protein. The residues that participate in binding of the protein to are then grafted onto those positions which are not necessary to maintain the tertiary structure of the protein scaffold to form the protein-binding protein.

The modified proteins of the present invention further include conservative variants of the modified proteins herein described, according to another embodiment. As used herein, a "conservative variant" refers to alterations in the amino acid sequence that do not substantially and adversely affect the binding or association capacity of the modified protein. A substitution, insertion or deletion is said to adversely affect the modified protein when the altered sequence prevents, reduces, or disrupts a function or activity associated with the modified protein. For example, the overall charge, structure or hydrophobic-hydrophilic properties of the modified protein can be altered without adversely affecting an activity. Accordingly, the amino acid sequence can be altered, for example to render the peptide more hydrophobic or hydrophilic, without adversely affecting the activities of the modified protein.

These variants, though possessing a slightly different amino acid sequence than those recited elsewhere herein, will still have the same or similar properties associated with any of the modified proteins discussed herein. Ordinarily, the conservative substitution variants, will have an amino acid sequence having at least 75%, at least 80%, at least 85%, at least 90%, at least 95% amino acid, at least 98%, or at least 99% sequence identity with any of the modified proteins discussed elsewhere herein.

Thus, the modified proteins of the present invention include molecules comprising any of the amino acid sequences discussed herein, including SEQ ID NOS: 10, 19, 25, 33, 35, 39, 41, 53, 65 and 70; or fragments thereof having a consecutive sequence of at least about 15, 20, 25, 30, 35 or more amino acid residues of the modified proteins of the invention; amino acid sequence variants of such sequences wherein at least one amino acid residue has been inserted N- or C-terminal to, or within, the disclosed sequence; amino acid sequence variants of the disclosed sequences, or their fragments as defined above, that have been substituted by another residue. Contemplated variants further include those derivatives wherein the modified protein has been covalently modified by substitution, chemical, enzymatic, or other appropriate means with a moiety other than a naturally occurring amino acid (for example, a detectable moiety such as an enzyme or radioisotope).

The present invention further provides, in another embodiment, nucleic acid molecules that encode any of the amino acid sequences discussed herein, including any of SEQ ID NOS: 10, 19, 25, 33, 35, 39, 41, 53, 65 and 70, or the related modified proteins herein described, preferably in isolated form. As used herein, "nucleic acid" includes cDNA and mRNA, as well as nucleic acids based on alternative backbones or including alternative bases whether derived from natural sources or synthesized. Those of ordinary skill in the art, given an amino acid sequence, will be able to generate corresponding nucleic acid sequences that can be used to generate the amino acid sequence, using no more than routine skill.

Modifications to the primary structure itself by deletion, addition, or alteration of the amino acids incorporated into the modified protein sequence during translation can be made without destroying the activity of the modified protein. Such substitutions or other alterations result in modified proteins having an amino acid sequence encoded by a nucleic acid falling within the contemplated scope of the present invention.

The present invention further provides, in some embodiments, recombinant DNA molecules that contain a coding sequence. As used herein, a "recombinant DNA molecule" is a DNA molecule that has been subjected to molecular manipulation. Methods for generating recombinant DNA molecules are well known in the art, for example, see Sambrook et al., 2012, Molecular Cloning: A Laboratory Manual, Cold Spring Harbor Laboratory, New York. In some recombinant DNA molecules, a coding DNA sequence is operably linked to expression control sequences and vector sequences.

The choice of vector and expression control sequences to which one of the modified protein family encoding sequences of the present invention is operably linked depends directly, as is well known in the art, on the functional properties desired (e.g., protein expression, and the host cell to be transformed). A vector of the present invention may be at least capable of directing the replication or insertion into the host chromosome, and preferably also expression, of the structural gene included in the recombinant DNA molecule.

Expression control elements that are used for regulating the expression of an operably linked protein encoding sequence are known in the art and include, but are not limited to, inducible promoters, constitutive promoters, secretion signals, and other regulatory elements. In some embodiments, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extra-chromosomal in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical of bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as *E. coli*. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Any suitable prokaryotic host can be used to express a recombinant DNA molecule encoding a modified protein of the invention.

Expression vectors compatible with eukaryotic cells, including those compatible with vertebrate cells, can also be used to form recombinant DNA molecules that contain a coding sequence. Eukaryotic cell expression vectors are well known in the art and are available from several commercial sources. Typically, such vectors are provided containing convenient restriction sites for insertion of the desired DNA segment.

Eukaryotic cell expression vectors used to construct the recombinant DNA molecules of the present invention may further include a selectable marker that is effective in a eukaryotic cell, such as a drug resistance selection marker. An example drug resistance marker is the gene whose expression results in neomycin resistance, i.e., the neomycin phosphotransferase (neo) gene. Alternatively, the selectable marker can be present on a separate plasmid, the two vectors introduced by co-transfection of the host cell, and transfectants selected by culturing in the appropriate drug for the selectable marker.

The present invention further provides, in yet another embodiment, host cells transformed with a nucleic acid molecule that encodes a modified protein of the present invention. The host cell can be either prokaryotic or eukaryotic. Eukaryotic cells useful for expression of a modified protein of the invention are not limited, so long as the cell line is compatible with cell culture methods and compatible with the propagation of the expression vector and expression of the gene product.

Transformation of appropriate cell hosts with a recombinant DNA molecule encoding a modified protein of the present invention is accomplished by well-known methods that typically depend on the type of vector used and host system employed. With regard to transformation of prokaryotic host cells, electroporation and salt treatment methods can be employed (see, for example, Sambrook et al., 2012, Molecular Cloning: A Laboratory Manual, Cold Spring Harbor Laboratory Press). With regard to transformation of vertebrate cells with vectors containing recombinant DNA, electroporation, cationic lipid or salt treatment methods can be employed (see, for example, Graham et al, (1973) Virology 52, 456-467; Wigler et al., (1979) Proc. Natl. Acad. Sci. USA 76, 1373-1376).

Successfully transformed cells can be identified by well-known techniques including the selection for a selectable marker. For example, cells resulting from the introduction of a recombinant DNA of the present invention can be cloned to produce single colonies. Cells from those colonies can be harvested, lysed and their DNA content examined for the presence of the recombinant DNA using a method such as that described by Southern, (1975) J. Mol. Biol. 98, 503-517 or the modified proteins produced from the cell assayed via an immunological method.

The present invention further provides, in still another embodiment, methods for producing a modified protein of the invention using nucleic acid molecules herein described. In general terms, the production of a recombinant form of a modified protein typically involves the following steps: a nucleic acid molecule is obtained that encodes a modified protein of the invention, such as the nucleic acid molecule encoding any of the modified proteins described herein, including any of SEQ ID NOS: 10, 19, 25, 33, 35, 39, 41, 53, 65 and 70.

The nucleic acid molecule may then be placed in operable linkage with suitable control sequences, as described above, to form an expression unit containing the modified protein open reading frame. The expression unit is used to transform a suitable host and the transformed host is cultured under conditions that allow the production of the recombinant modified protein. Optionally the recombinant modified protein is isolated from the medium or from the cells; recovery and purification of the modified protein may not be necessary in some instances where some impurities may be tolerated.

Each of the foregoing steps can be done in a variety of ways. The construction of expression vectors that are operable in a variety of hosts is accomplished using appropriate replicons and control sequences, as set forth above. The control sequences, expression vectors, and transformation methods are dependent on the type of host cell used to express the gene. Suitable restriction sites, if not normally available, can be added to the ends of the coding sequence so as to provide an excisable gene to insert into these vectors. An artisan of ordinary skill in the art can readily adapt any host/expression system known in the art for use with the nucleic acid molecules of the invention to produce a recombinant modified protein.

In another embodiment, the present invention provides methods for use in isolating and identifying binding partners of the modified proteins of the invention. In some embodiments, a modified protein of the invention is mixed with a potential binding partner or an extract or fraction of a cell under conditions that allow the association of potential binding partners with the modified protein of the invention. After mixing, peptides, polypeptides, proteins or other molecules that have become associated with a modified protein of the invention are separated from the mixture. The binding partner bound to the modified protein of the invention can then be removed and further analyzed. To identify and isolate a binding partner, the entire modified protein can be used. Alternatively, a fragment of the modified protein which contains the binding domain can be used.

In another embodiment, the nucleic acid molecules encoding a modified protein of the invention can be used in a yeast two-hybrid system. The yeast two-hybrid system has been used to identify other modified protein partner pairs and can readily be adapted to employ the nucleic acid molecules herein described (see, e.g., Stratagene Hybrizap® two-hybrid system).

According to some embodiments, the modified proteins of the invention are useful for drug screening to identify agents capable of binding to the same binding site as the modified proteins. The modified proteins are also useful for diagnostic purposes to identify the presence and/or detect the levels of DNA or protein that binds to the modified proteins of the invention. In one diagnostic embodiment, the modified proteins of the invention are included in a kit used to detect the presence of a particular DNA or protein in a biological sample. The modified proteins of the invention also have therapeutic uses in the treatment of disease associated with the presence of a particular DNA or protein. In one therapeutic embodiment, the modified proteins can be used to bind to DNA to promote or inhibit transcription, while in another therapeutic embodiment, the proteins bind to a protein resulting in inhibition or stimulation of the protein.

In some embodiments of the invention, modified proteins of the invention are administrated to a subject in an effective amount to treat a cancer or a disease or disorder. Non-limiting examples of such modified proteins include those comprising SEQ ID NOS: 10, 19, 25, 33, 35, 39, 41, 53, 65 and 70. The modified proteins of the invention may be administrated to cells of a subject to treat or prevent a disease or disorder (e.g., cancers) alone or in combination with the administration of other therapeutic compounds for the treatment or prevention of these diseases or disorders.

In certain embodiments, the modified proteins of the invention are useful for diagnostic purposes to identify the presence and/or detect the levels of a target protein that binds to the proteins of the invention. The modified proteins of this method can be labeled with a detectable marker. A wide range of detectable markers can be used, including but not limited to biotin, a fluorogen, an enzyme, an epitope, a chromogen, or a radionuclide. The method for detecting the label will depend on the nature of the label and can be any known in the art, e.g., film to detect a radionuclide, an enzyme substrate that gives rise to a detectable signal to detect the presence of an enzyme, antibody to detect the presence of an epitope, etc.

Modified Protein Mediated Cargo Delivery

The present invention relates to compositions and methods for promoting transduction of cargo molecules into the cytosol of cells. In one embodiment, the present invention relates to a composition comprising a modified protein, as described herein, and a cargo molecule. In one embodiment, the modified protein compositions serve to transduce the molecules, and associated cargo, into cells. In certain embodiments, the cargo molecule is not covalently linked to the modified protein. For example, as demonstrated herein co-administration of the modified protein composition and a cargo molecule results in cytosolic delivery of the modified protein and associated, non-covalently linked, cargo molecule. Modified protein compositions have the property of being able to cross a cell membrane and transport an associated cargo molecule to an intracellular compartment of a cell, including the cytosol.

In some embodiments, the modified protein composition of the invention comprises at least 4 cationic amino acid residues, such as arginine, wherein the at least 4 cationic residues are displayed on at least 3 α-helical faces. In other embodiments, the modified protein of the invention comprises at least 5 cationic amino acid residues, such as arginine, wherein the at least 5 cationic residues are displayed on at least 3 α-helical faces. In various embodiments, the modified protein of the invention comprises at least one selected from the group consisting of SEQ ID NOS: 10, 19, 25, 33, 35, 39, 41, 53, 65 and 70.

As described herein, components of the modified protein composition and associated cargo can be organized in nearly any fashion provided that the cargo has the function for which it was intended. In some embodiments, the cargo molecule may include tags, e.g., to facilitate detection, quantification, identification and/or purification of the fusion protein.

The modified protein composition can be synthesized in solid or solution phase, for example, using Fmoc or tBOC chemistries (Merrifield, J. Am. Chem. Soc. 85, 2149-2154, 1963; Roberge et al., Science 269, 202-204, 1995). Peptide synthesis can be performed using manual techniques or by automation. Automated synthesis can be achieved, for example, using an Applied Biosystems 431A Peptide Synthesizer (Perkin Elmer).

Peptides can be made recombinantly by cloning a coding sequence for the peptide and expressing it in vitro. Any polynucleotide sequence that encodes a modified protein composition can be used. The polynucleotide sequence can be synthesized in vitro using, e.g., phosphoroamidite chemistry. Nucleic acid synthesis can be performed using manual techniques or by automation. Automated synthesis can be achieved, for example, using an Applied Biosystems 3900 DNA Synthesizer (Perkin Elmer).

In some embodiments, the present invention is a nucleic acid encoding a modified protein and associated cargo of the invention. In certain embodiments, when the cargo is a polypeptide sequence, the modified protein composition and cargo peptide are not linked. For example, in certain embodiments, the invention comprises a nucleic acid encoding at least two polypeptides, including the modified protein composition at the cargo polypeptide.

In some embodiments, the modified protein composition and associated cargo described herein are produced by recombinant DNA techniques. For example, a DNA molecule encoding the modified protein composition can be ligated to another DNA molecule encoding the associated cargo polypeptide. In this instance, the resultant hybrid DNA molecule can be expressed in a suitable host cell to produce the modified protein composition and/or associated cargo. The DNA molecules are ligated to each other in a 5' to 3' orientation such that, after ligation, the translational frame of the encoded polypeptides is not altered (i.e., the DNA molecules are ligated to each other in-frame).

A polynucleotide can be inserted into an expression vector which contains the necessary elements for the transcription and translation of the inserted coding sequence. Transcription and translation control elements include, for example, a promoter (e.g., T7 or T3), ribosome binding site, start codon, stop codon, and polyadenylation site. Methods which are well known to those skilled in the art can be used to construct expression vectors containing sequences encoding the modified protein composition and associated cargo polypeptides and appropriate transcriptional and translational control elements. These methods include in vitro recombinant DNA techniques, synthetic techniques, and in vivo genetic recombination. Such techniques are described, for example, in Sambrook et al., 2012, Molecular Cloning: A Laboratory Manual, Cold Spring Harbor Laboratory, New York and in Ausubel et al., 1997, Current Protocols in Molecular Biology, John Wiley & Sons, New York.

A variety of expression systems are available for expressing sequences that encode the modified protein composition and associated cargo. Examples of such systems include, but are not limited to, bacteria, yeast, insect, plant, and animal cell systems. Bacteria can be transformed with recombinant bacteriophage, expression plasmids, or cosmid expression vectors. Yeast can be transformed with yeast expression vectors. Insect cells can be transfected with expression vectors or transduced with recombinant insect viruses (e.g., baculovirus). Plant cells can be transduced with recombinant plant viruses (e.g., cauliflower mosaic virus or tobacco mosaic virus). Animal cells can be transfected with expression vectors (e. g., pcDNA3 or pCMV-Sport) or transduced with recombinant viruses (e.g., retroviruses, adenoviruses, or semliki forest virus). Methods for transforming, transfecting, or transducing host cells are well-known in the art, and any appropriate method can be used.

Nucleic acid encoding the modified protein composition and associated cargo can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et al., 2012, Molecular Cloning: A Laboratory Manual, Cold Spring Harbor Laboratory, New York and other laboratory textbooks.

The modified protein composition and associated cargo can be purified from host cells or host cell culture medium by any method known in the art for purifying polypeptides. Examples of such methods include salt fractionation, high pressure liquid chromatography, antibody column chromatography, affinity tag column chromatography, and acrylamide gel electrophoresis. Such methods are well known to those skilled in the art.

As described elsewhere herein, the modified protein composition and associated cargo of the present invention are transduced into target cells or groups of such target cells. Transduction efficiency can be monitored and quantified if desired by one or a combination of different strategies. For example, one approach involves an in vitro assay that measures uptake of the modified protein composition and associated cargo by the cell. The assay includes detectably-labeling the modified protein composition, associated cargo, or both, with, e.g., a radioactive atom, fluorescent, phosphorescent, dexamethasone, or luminescent tag (e.g., fluorescein, rhodamine or FITC) and then measuring uptake of the labeled modified protein composition or associated cargo. Alternatively, the modified protein composition, associated cargo, or both can be labeled with an enzyme capable of forming a detectable label such as horseradish peroxidase, P-galactosidase, chloramphenicol acetyl transferase or luciferase. In a preferred approach, it is possible to genetically fuse a modified protein composition or associated cargo to florescent protein, such as green fluorescent protein (GFP), and then assay the location of the modified protein composition or associated cargo. Uptake can be measured by several conventional methods such as by quantifying labeled cells in a standard cell sorter (e.g., FACS), by fluorescence microscopy or by autoradiography.

The modified protein composition and associated cargo of the invention are capable of transducing at least about 5%, 10%, 20%, or more of the total number of target cells as determined by any methods for monitoring uptake of the fusion molecule by cells, such as FACS or related microscopical techniques. The total number of target cells can be estimated by standard techniques.

The modified protein composition and associated cargo can also be made by transcribing and translating a coding sequence in a cell-free expression system. A coding sequence for the modified protein composition and associated cargo can be linked to appropriate transcription and translation control elements by methods well known in the art. Examples of such methods include PCR, restriction enzyme digestion and ligation, and chemical synthesis. Such techniques are described, for example, in Sambrook et al., 2012, Molecular Cloning: A Laboratory Manual, Cold Spring Harbor Laboratory, New York and in Ausubel et al., 1997, Current Protocols in Molecular Biology, John Wiley & Sons, New York. Cell-free transcription and translation can be accomplished, for example, using components of rabbit reticulocyte or wheat germ extracts, which are available in kits from commercial suppliers such as Promega Corporation.

The modified protein composition and associated cargo of the invention can contain conservative substitutions, i.e., exchange of one amino acid for another having similar properties. Examples of conservative substitutions include, but are not limited to, 1) glycine and alanine; 2) valine, isoleucine, and leucine; 3) aspartic acid and glutamic acid; 4) lysine and arginine; 5) asparagine and glutamine; and 6) serine and threonine.

The modified protein composition and associated cargo can be synthesized from D- or L-amino acids. In addition, use of amino acid analogs is also contemplated. Examples of amino acid analogs includes, but is not limited to, ethyl esters, methyl esters, naphthylamides, and 7-amido-4-methyl coumarin.

The modified protein composition, associated cargo, or both can also have a linker attached to the N-terminus or the C-terminus. The linker is usually 0, 1, 2, 3, 4, 5 or more amino acids in length and can be a small neutral polar or non-polar amino acid such as glycine, cysteine, serine, or threonine. An exemplary linker has an amino acid sequence Lys-Xaa-Xaa, wherein Xaa is a small neutral polar or nonpolar amino acid. In some embodiments, Xaa is glycine.

The cargo can be a small molecule (e.g., a radionuclide, a fluorescent marker, a dye, or a pharmaceutical agent), a protein (e.g., an immortalizing agent, an anti-apoptotic agent, an enzyme, an oncoprotein, a cell cycle regulatory protein, or an antibody), or a nucleic acid (e.g., RNA, DNA, and cDNA). Any of these cargo can be pharmaceutical agents. The small molecule also can be, for example, a radionuclide, a fluorescent marker, or a dye. A polypeptide according to the invention is a polymer of amino acids comprising two or more amino acid residues and includes peptides and proteins. The polypeptide can be, for example, an immortalization protein (e.g., SV40 large T antigen and telomerase), an anti-apoptotic protein (e.g., mutant p53 and Bclx L), an antibody, an oncogene (e.g., ras, myc, HPV E6/E7, and Adenovirus Ela), a cell cycle regulatory protein (e.g., cyclin and cyclin-dependent kinase), a zinc finger nuclease (ZFN), or an enzyme (e.g., green fluorescent protein, β-galactosidase, and chloramphenicol acetyl transferase). The nucleic acid can be, e.g., RNA, DNA, or cDNA. The sequence of the nucleic acid can be a coding or a non-coding sequence (e.g., an antisense oligonucleotide). Nucleotides in the nucleic acid cargo domain can be standard nucleotides (e.g., adenosine, cytosine, guanine, thymine, inosine, and uracil) or they can be nucleotide derivatives (e.g., biotinylated nucleotide) or analogs (e.g., phosphorothioate nucleotides). For example, the nucleic acid cargo can be an antisense sequence comprising phosphorothioate nucleotides.

Exemplary cargo will have sizes conducive to the function for which those domains are intended. In particular, preferred cargo can be at least about 0.1, 0.2, 0.5, 0.75, 1, 5, 10, 25, 30, 50, 100, 200, 500 kD, up to about 1000 kD or more.

A cargo can be complexed to the modified protein composition by any method known in the art and which is appropriate for a particular cargo. The skilled artisan will be able to choose the appropriate method to complex a cargo with the modified protein composition. In certain embodiments, the cargo is not covalently linked or attached to the modified protein composition. For example, in certain embodiments, the association of the modified protein composition and associated cargo involves various noncovalent interactions such as including hydrogen bonding, metal coordination, hydrophobic forces, van der Waals forces, pi-pi interactions, and/or electrostatic effects.

The modified protein composition and associated cargo of the present invention can be separated and purified by appropriate combination of known techniques. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electrical charge such as ion-exchange column chromatography, methods utilizing specific affinity such as affinity chromatograph, methods utilizing a difference in hydrophobicity such as reverse-phase high performance liquid chromatograph and methods utilizing a difference in isoelectric point, such as isoelectric focusing electrophoresis, metal affinity columns such as Ni-NTA. See generally Sambrook et al., 2012, Molecular Cloning: A Laboratory Manual, Cold Spring Harbor Laboratory Press and Ausubel et al., 1997, Current Protocols in Molecular Biology, John Wiley & Sons, New York for disclosure relating to these methods.

In some embodiments, the modified protein composition and associated cargo of the present invention are part of a substantially pure preparation. That is, the modified protein composition and associated cargo have been isolated from cell substituents that naturally accompany it so that the fusion proteins are present in at least 80% or 90% to 95% homogeneity (w/w). The modified protein composition and associated cargo having at least 98 to 99% homogeneity (w/w) are most preferred for many pharmaceutical, clinical and research applications. Once substantially purified the modified protein composition and associated cargo should be substantially free of contaminants for therapeutic applications. Once purified partially or to substantial purity, the modified protein composition and associated cargo can be used therapeutically, or in performing in vitro or in vivo assays as disclosed herein. Substantial purity can be determined by a variety of standard techniques such as chromatography and gel electrophoresis.

The modified protein composition can transport a cargo into a variety of mammalian, amphibian, reptilian, avian, or insect cells. Cells can be primary cells or cell lines. Mammalian cells can be, e.g., human, monkey, rat, mouse, dog, cow, pig, horse, hamster, and rabbit. Primary cells from mammalians include, but are not limited to, adipocytes, astrocytes, cardiac muscle cells, chondrocytes, endothelial cells, epithelial cells, fibroblasts, gangliocytes, glandular cells, glial cells, hematopoietic cells, hepatocytes, keratinocytes, myoblasts, neural cells, osteoblasts, ovary cells, pancreatic beta cells, renal cells, smooth muscle cells, and striated muscle cells.

Modified Protein Fusion Molecules

The present invention relates to compositions and methods for promoting transduction of cargo molecules into the cytosol of cells. The modified protein domains (MPDs) of the fusion molecule compositions described herein serve to transduce the molecules, and fusion molecules, into cells. By the term "fusion molecule" as it is used herein is meant a MPD and a cargo domain covalently linked (i.e., fused) by recombinant, chemical or other suitable method. If desired, the fusion molecule can be fused at one or several sites through a linker sequence, such as a peptide linker sequence. In some embodiments, the fusion molecules are fusion proteins.

Modified protein fusion molecules having an MPD have the property of being able to cross a cell membrane and transport a cargo domain to an intracellular compartment of a cell, including the cytosol. MPDs of the present invention can be made by any method known in the art for synthesizing peptide fusion molecules. For example, MPDs can be synthesized chemically or can be made recombinantly.

In some embodiments, the MPD of the invention comprises at least 4 cationic amino acid residues, such as arginine, wherein the at least 4 cationic residues are displayed on at least 3 α-helical faces. In other embodiments, the modified protein of the invention comprises at least 5 cationic amino acid residues, such as arginine, wherein the at least 5 cationic residues are displayed on at least 3 α-helical faces. In various embodiments, the modified protein of the invention comprises at least one selected from the group consisting of SEQ ID NOS: 10, 19, 25, 33, 35, 39, 41, 53, 65 and 70.

As described herein, components of the fusion molecules disclosed herein, e.g., a transducing MPD and a cargo domain, can be organized in nearly any fashion provided that the fusion protein has the function for which it was intended. In some embodiments, each component of the fusion protein can be spaced from another component by at least one suitable linker sequence, such as a peptide linker sequence, if desired. In some embodiments, the fusion proteins may include tags, e.g., to facilitate identification and/or purification of the fusion protein.

Preferred peptide linker sequences typically comprise up from about 1 to about 30 amino acids. In some embodiments, the linker sequence is flexible so as not to hold the fusion molecule in a single rigid conformation. The linker sequence can be used, for example, to space the DNA binding protein from another domain. In some embodiments, the peptide linker sequence can be positioned between the modified protein domain and the cargo domain, e.g., to chemically cross-link the domains and to provide molecular flexibility.

MPDs can be synthesized in solid or solution phase, for example, using Fmoc or tBOC chemistries (Merrifield, J.

Am. Chem. Soc. 85, 2149-2154, 1963; Roberge et al., Science 269, 202-204, 1995). Peptide synthesis can be performed using manual techniques or by automation. Automated synthesis can be achieved, for example, using an Applied Biosystems 431A Peptide Synthesizer (Perkin Elmer).

Peptides can be made recombinantly by cloning a coding sequence for the peptide and expressing it in vitro. Any polynucleotide sequence that encodes a MPD can be used. The polynucleotide sequence can be synthesized in vitro using, e.g., phosphoroamidite chemistry. Nucleic acid synthesis can be performed using manual techniques or by automation. Automated synthesis can be achieved, for example, using an Applied Biosystems 3900 DNA Synthesizer (Perkin Elmer).

In some embodiments, the present invention is a nucleic acid encoding a fusion protein of the invention. When the cargo domain is a polypeptide sequence, the term fusion protein is intended to describe at least two polypeptides, typically from different sources, which are operatively linked. With regard to the polypeptides, the term "operatively linked" is intended to mean that the two polypeptides are connected in manner such that each polypeptide can serve its intended function. In some embodiments, the two polypeptides are covalently attached through peptide bonds. As discussed elsewhere herein, the two polypeptides may be separated by a peptide linker when desired.

In some embodiments, the fusion proteins described herein are produced by recombinant DNA techniques. For example, a DNA molecule encoding the first polypeptide can be ligated to another DNA molecule encoding the second polypeptide. In this instance, the resultant hybrid DNA molecule can be expressed in a suitable host cell to produce the fusion protein. The DNA molecules are ligated to each other in a 5' to 3' orientation such that, after ligation, the translational frame of the encoded polypeptides is not altered (i.e., the DNA molecules are ligated to each other in-frame). The resulting DNA molecules encode an in-frame fusion protein. The components of the fusion protein can be organized in nearly any order provided each is capable of performing its intended function. In an exemplary configuration, the C-terminus of the modified protein domain is operatively linked to the N-terminus of the cargo domain. That linkage can be achieved by recombinant methods if desired. However, in another configuration, the N-terminus of the modified protein domain is linked to the C-terminus of the cargo domain.

A MPD-encoding polynucleotide can be inserted into an expression vector which contains the necessary elements for the transcription and translation of the inserted coding sequence. Transcription and translation control elements include, for example, a promoter (e.g., T7 or T3), ribosome binding site, start codon, stop codon, and polyadenylation site. Methods which are well known to those skilled in the art can be used to construct expression vectors containing sequences encoding MPD-containing polypeptides and appropriate transcriptional and translational control elements. These methods include in vitro recombinant DNA techniques, synthetic techniques, and in vivo genetic recombination. Such techniques are described, for example, in Sambrook et al., 2012, Molecular Cloning: A Laboratory Manual, Cold Spring Harbor Laboratory, New York and in Ausubel et al., 1997, Current Protocols in Molecular Biology, John Wiley & Sons, New York.

A variety of expression systems are available for expressing sequences that encode a MPD. Examples of such systems include, but are not limited to, bacteria, yeast, insect, plant, and animal cell systems. Bacteria can be transformed with recombinant bacteriophage, expression plasmids, or cosmid expression vectors. Yeast can be transformed with yeast expression vectors. Insect cells can be transfected with expression vectors or transduced with recombinant insect viruses (e.g., baculovirus). Plant cells can be transduced with recombinant plant viruses (e.g., cauliflower mosaic virus or tobacco mosaic virus). Animal cells can be transfected with expression vectors (e. g., pcDNA3 or pCMV-Sport) or transduced with recombinant viruses (e.g., retroviruses, adenoviruses, or semliki forest virus). Methods for transforming, transfecting, or transducing host cells are well-known in the art, and any appropriate method can be used.

Nucleic acid encoding a desired fusion protein can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et al., 2012, Molecular Cloning: A Laboratory Manual, Cold Spring Harbor Laboratory, New York and other laboratory textbooks.

A MPD can be purified from host cells or host cell culture medium by any method known in the art for purifying polypeptides. Examples of such methods include salt fractionation, high pressure liquid chromatography, antibody column chromatography, affinity tag column chromatography, and acrylamide gel electrophoresis. Such methods are well known to those skilled in the art. As described elsewhere herein, the fusion molecules of the present invention are transduced into target cells or groups of such target cells. Transduction efficiency can be monitored and quantified if desired by one or a combination of different strategies. For example, one approach involves an in vitro assay that measures uptake of the fusion protein by the cell. The assay includes detectably-labeling the fusion protein with, e.g., a radioactive atom, fluorescent, phosphorescent, dexamethasone, or luminescent tag (e.g., fluorescein, rhodamine or FITC) and then measuring uptake of the labeled fusion protein. Alternatively, the fusion protein can be labeled with an enzyme capable of forming a detectable label such as horseradish peroxidase, P-galactosidase, chloramphenicol acetyl transferase or luciferase. In a preferred approach, it is possible to genetically fuse a desired fusion protein to florescent protein, such as green fluorescent protein (GFP), and then assay the location of the fusion protein. Uptake can be measured by several conventional methods such as by quantifying labeled cells in a standard cell sorter (e. g., FACS), by fluorescence microscopy or by autoradiography.

The fusion molecules of the invention are capable of transducing at least about 5%, 10%, 20%, or more of the total number of target cells as determined by any methods for monitoring uptake of the fusion molecule by cells, such as FACS or related microscopical techniques. The total number of target cells can be estimated by standard techniques.

A MPD can also be made by transcribing and translating a MPD coding sequence in a cell-free expression system. A coding sequence for a MPD can be linked to appropriate transcription and translation control elements by methods well known in the art. Examples of such methods include PCR, restriction enzyme digestion and ligation, and chemical synthesis. Such techniques are described, for example, in Sambrook et al., 2012, Molecular Cloning: A Laboratory Manual, Cold Spring Harbor Laboratory, New York and in Ausubel et al., 1997, Current Protocols in Molecular Biology, John Wiley & Sons, New York. Cell-free transcription and translation can be accomplished, for example, using components of rabbit reticulocyte or wheat germ extracts, which are available in kits from commercial suppliers such as Promega Corporation.

MPDs of the invention can contain conservative substitutions, i.e., exchange of one amino acid for another having similar properties. Examples of conservative substitutions include, but are not limited to, 1) glycine and alanine; 2) valine, isoleucine, and leucine; 3) aspartic acid and glutamic acid; 4) lysine and arginine; 5) asparagine and glutamine; and 6) serine and threonine.

A MPD can be synthesized from D- or L amino acids. In addition, use of amino acid analogs is also contemplated. Examples of amino acid analogs includes, but is not limited to, ethyl esters, methyl esters, naphthylamides, and 7-amido-4-methyl coumarin.

MPDs of the present invention can also have a linker attached to the N-terminus or the C-terminus. The linker is usually 0, 1, 2, 3, 4, 5 or more amino acids in length and can be a small neutral polar or non-polar amino acid such as glycine, cysteine, serine, or threonine. An exemplary linker has an amino acid sequence Lys-Xaa-Xaa, wherein Xaa is a small neutral polar or nonpolar amino acid. In some embodiments, Xaa is glycine.

The cargo domain can be a small molecule (e.g., a radionuclide, a fluorescent marker, a dye, or a pharmaceutical agent), a protein (e.g., an immortalizing agent, an anti-apoptotic agent, an enzyme, an oncoprotein, a cell cycle regulatory protein, or an antibody), or a nucleic acid (e.g., RNA, DNA, and cDNA). Any of these cargo domains can be pharmaceutical agents. The small molecule also can be, for example, a radionuclide, a fluorescent marker, or a dye. A polypeptide according to the invention is a polymer of amino acids comprising two or more amino acid residues and includes peptides and proteins. The polypeptide can be, for example, an immortalization protein (e.g., SV40 large T antigen and telomerase), an anti-apoptotic protein (e.g., mutant p53 and Bclx L), an antibody, an oncogene (e.g., ras, myc, HPV E6/E7, and Adenovirus Ela), a cell cycle regulatory protein (e.g., cyclin and cyclin-dependent kinase), a zinc finger nuclease (ZFN), or an enzyme (e.g., green fluorescent protein, β-galactosidase, and chloramphenicol acetyl transferase). The nucleic acid can be, e.g., RNA, DNA, or cDNA. The sequence of the nucleic acid can be a coding or a non-coding sequence (e.g., an antisense oligonucleotide). Nucleotides in the nucleic acid cargo domain can be standard nucleotides (e.g., adenosine, cytosine, guanine, thymine, inosine, and uracil) or they can be nucleotide derivatives (e.g., biotinylated nucleotide) or analogs (e.g., phosphorothioate nucleotides). For example, the nucleic acid cargo domain can be an antisense sequence comprising phosphorothioate nucleotides.

Exemplary cargo domains will have sizes conducive to the function for which those domains are intended. In particular, preferred cargo domains can be at least about 0.1, 0.2, 0.5, 0.75, 1, 5, 10, 25, 30, 50, 100, 200, 500 kD, up to about 1000 kD or more. It should be apparent that in many cases, the size of the cargo domain dominates the size of the fusion protein.

A cargo domain can be complexed to a MPD by any method known in the art and which is appropriate for a particular cargo domain. The skilled artisan will be able to choose the appropriate method to complex a cargo domain with a MPD. Examples of such methods include, but are not limited to, chemical cross-linking, genetic fusion, and bridging.

A linker can be used to cross-link a MPD with a cargo domain. The linker can be cleavable to facilitate separation of the MPD from the cargo domain after the MPD transports the cargo domain across a cell membrane.

The fusion molecules of the present invention can be separated and purified by appropriate combination of known techniques. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electrical charge such as ion-exchange column chromatography, methods utilizing specific affinity such as affinity chromatograph, methods utilizing a difference in hydrophobicity such as reverse-phase high performance liquid chromatograph and methods utilizing a difference in isoelectric point, such as isoelectric focusing electrophoresis, metal affinity columns such as Ni-NTA. See generally Sambrook et al., 2012, Molecular Cloning: A Laboratory Manual, Cold Spring Harbor Laboratory Press and Ausubel et al., 1997, Current Protocols in Molecular Biology, John Wiley & Sons, New York for disclosure relating to these methods.

In some embodiments, the fusion molecules of the present invention are part of a substantially pure preparation. That is, the fusion molecules have been isolated from cell substituents that naturally accompany it so that the fusion proteins are present in at least 80% or 90% to 95% homogeneity (w/w). Fusion molecules having at least 98 to 99% homogeneity (w/w) are most preferred for many pharmaceutical, clinical and research applications. Once substantially purified the fusion molecule should be substantially free of contaminants for therapeutic applications. Once purified partially or to substantial purity, the fusion molecule can be used therapeutically, or in performing in vitro or in vivo assays as disclosed herein. Substantial purity can be determined by a variety of standard techniques such as chromatography and gel electrophoresis.

Genetic fusions can be generated by linking a coding sequence for a MPD in-frame with a coding sequence for a polypeptide cargo domain. Many methods exist in the art for linking coding sequences together. Exemplary methods include, but are not limited to, polymerase chain reaction (PCR), stitch PCR, and restriction endonuclease digestion and ligation. For example, a coding sequence for a MPD can be added to the 5'-end of a PCR primer for a cargo domain of choice; after PCR, the coding sequences for the MPD and the polypeptide cargo domain will be linked together. The skilled artisan will know how to ensure that the reading frames of the MPD and the cargo domain are in frame and where transcriptional control sequences (e.g., start codon and stop codon) should be placed. A protease cleavage site can be included between the MPD and the cargo domain. Examples of such protease cleavage sites include, but are not limited to Factor Xa and tobacco etch virus (TEV) protease.

MPDs and cargo domains can be complexed using pairs of bridging molecules. Examples of such pairs include, but are not limited to, (a) streptavidin and biotin, (b) glutathione and glutathione-S-transferase, and (c) polyhistidine and an affinity chromatography reagent (e.g., tetradentate nitrilotriacetic acid (NTA) or iminodiacetic acid (IDA)), which interact through an ion such as Ni+2. A MPD can be linked to either member of the pair, and a cargo is linked to the other bridging molecule. For example, if the MPD is linked to glutathione-S-transferase then the cargo is linked to glutathione. In some embodiments, the MPD is linked to streptavidin and the cargo is linked to biotin. The MPD and the streptavidin can be linked by any method known in the art for linking a peptide and a bridging molecule. Examples of such methods include, but are not limited to, chemical cross-linking or genetic fusion. The cargo is then linked to biotin by any method known in the art for biotinylating small molecules, proteins, or nucleic acids, such as chemical cross-linking. The MPD cargo domain complex can be formed by contacting the MPD-streptavidin with the biotinylated cargo domain.

In another embodiment, glutathione and glutathione-S-transferase are used as the pair of bridging molecules. In this case, for example, the MPD can be linked to the glutathione-S-transferase and the cargo can be linked to the glutathione. The MPD and the glutathione-S-transferase can be linked by any method described above, although genetic fusion is preferred. The cargo is linked to the glutathione by any method known in the art for linking glutathione to small molecules, proteins, or nucleic acids. An example of such method is chemical cross-linking. The MPD-cargo domain complex can be formed by contacting the MPD-glutathione-S-transferase with the glutathione-linked cargo domain.

In yet another embodiment, an affinity chromatography reagent and polyhistidine are used as the pair of bridging molecules. In this case, for example, the MPD can be linked to the affinity chromatography reagent. The affinity chromatography reagents bind ions such as Ni+2 with different affinities. NTA binds Ni+2 with stronger affinity that IDA. A skilled artisan will be able to choose which binding affinity is desired for a particular application. The MPD and affinity chromatography reagent can be linked by, for example, chemical cross linking. The cargo is linked to polyhistidine by any method known in the art for linking polyhistidine to small molecules, proteins, or nucleic acids. The MPD-cargo domain complex can be formed by contacting the MPD-affinity chromatography reagent complex with the polyhistidine-linked cargo domain in the presence of an ion such as Ni+2.

A MPD and cargo domain can be complexed chemically or using pairs of bridging molecules at any position on either the MPD or the cargo domain, providing that functionality of either the MPD or cargo domain is not destroyed. For example, a cross-linking agent will react with appropriate functional groups located at the amino-terminus or carboxy-terminus (for proteins), at the 5' end or 3' end (for nucleic acids), or throughout the small molecule. A skilled artisan will be able to determine if the respective parts of the MPD-cargo domain complex retains biological activity. By way of example, the MPD retains biological activity if it retains is ability to transport cargo into a cell. Transport activity can be ascertained, for example, by adding the MPD cargo domain complex to cells and assaying the cells to determine if the cargo domain was delivered across the cell membrane. One skilled in the art can determine if the cargo is located intracellularly using methods well known in the art (e.g., immunohistochemical staining). The cargo domain can be assayed for activity using a method acceptable for the type of cargo domain (e.g., an enzyme assay for an enzyme, a transformation assay for an oncoprotein, an anti-apoptotic assay for an anti-apoptosis protein, and an immortalization assay for an immortalization protein). These assays are well known in the art and are described in Sambrook et al., 2012, Molecular Cloning: A Laboratory Manual, Cold Spring Harbor Laboratory, New York and Ausubel et al., 1997, Current Protocols in Molecular Biology, John Wiley & Sons, New York.

If the MPD and polypeptide cargo domain are genetically linked, the polypeptide cargo domain can be complexed to either the amino terminus of the MPD or to the carboxy-terminus of the MPD. In some embodiments, the polypeptide cargo domain is complexed to the carboxy-terminus of the MPD.

MPDs of the invention can transport a cargo domain into a variety of mammalian, amphibian, reptilian, avian, or insect cells. Cells can be primary cells or cell lines. Mammalian cells can be, e.g., human, monkey, rat, mouse, dog, cow, pig, horse, hamster, and rabbit. Primary cells from mammalians include, but are not limited to, adipocytes, astrocytes, cardiac muscle cells, chondrocytes, endothelial cells, epithelial cells, fibroblasts, gangliocytes, glandular cells, glial cells, hematopoietic cells, hepatocytes, keratinocytes, myoblasts, neural cells, osteoblasts, ovary cells, pancreatic beta cells, renal cells, smooth muscle cells, and striated muscle cells.

Pharmaceutical Compositions and Methods of Treatment

In various embodiments, the present invention is a method of treating a disease or disorder in a subject in need thereof, by administering to the subject, a modified protein, or a modified protein fusion molecule, as described elsewhere herein.

In various embodiments, the modified proteins, or modified protein fusion molecules of the invention can be administered to cells in vitro, ex vivo, or in vivo, for example, by using a specified delivery mechanism suitable for introduction of into those cells. In general, the type of delivery mechanism selected will be guided by several considerations including the location of the cells, the degree of transduction needed to modulate a biologic activity within the cell, and the general health of the cells.

In particular, pharmaceutical compositions comprising at least one modified protein, and/or at least one modified protein fusion molecule of the invention may be administered to a mammal, particularly a primate such as a human, using a variety of suitable routes including oral, topical (including transdermal, buccal or sublingual), nasal and parenteral (including intraperitoneal, subcutaneous, intravenous, intradermal or intramuscular injection.

Formulations of the modified proteins include those suitable for oral/nasal, topical, parenteral and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Methods of preparing these formulations or compositions include combining one compound and a carrier and, optionally, one or more accessory ingredients. In general, the formulations are prepared by combining a compound with a liquid carrier, or a finely divided solid carrier, or both, and then, if necessary, shaping the product.

Formulations of the modified proteins, or modified protein fusion molecules, suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound as an active ingredient. A compound may also be administered as a bolus, electuary or paste. In solid dosage forms for oral administration (capsules, tablets, pills, dragees, powders, granules, and the like), a modified protein is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and/or (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration of a modified protein include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds (e.g., modified proteins), may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof. Methods of the invention can be administered topically in some embodiments, either to skin or to mucosal membranes (e.g., those on the cervix and vagina). This offers the greatest opportunity for direct delivery to tumor with the lowest chance of inducing side effects. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur. Dosage forms for the topical or transdermal administration of a compound (e.g., a modified protein) include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to a therapeutic compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Injectable depot forms are made by forming microencapsule matrices of the compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

Formulations of the compounds for intravaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound. Optionally, such formulations suitable for vaginal administration also include pessaries, tampons, creams, gels, pastes, foams or spray formulations containing such carriers as are known in the art to be appropriate.

The pharmaceutical compositions useful for practicing the invention may be administered to deliver a dose of between about 0.1 ng/kg/day and 100 mg/kg/day. In various embodiments, the pharmaceutical compositions useful in the methods of the invention may be administered, by way of example, systemically, parenterally, orally, or topically. In addition to the appropriate therapeutic composition, such pharmaceutical compositions may contain pharmaceutically acceptable carriers and other ingredients known to enhance and facilitate drug administration.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Pharmaceutical compositions that are useful in the methods of the invention may be prepared, packaged, or sold in formulations suitable for oral, parenteral, topical, intravenous, intramuscular, and other known routes of administration.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, cutaneous, subcutaneous, intraperitoneal, intravenous, and intramuscular.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g., sterile pyrogen-free water) prior to parenteral administration of the reconstituted composition.

Typically dosages of the compound of the invention which may be administered to an animal, preferably a human, range in amount from about 0.01 mg to 20 about 100 g per kilogram of body weight of the animal. While the precise dosage administered will vary depending upon any number of factors, including, but not limited to, the type of animal and type of disease state being treated, the age of the animal and the route of administration. In various embodiments, the dosage of the compound will vary from about 1 mg to about 100 mg per kilogram of body weight of the animal. In other various embodiments, the dosage will vary from about 1 µg to about 1 g per kilogram of body weight of the animal. The compound can be administered to an animal as frequently as several times daily, or it can be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

It will be appreciated by one of skill in the art, when armed with the present disclosure including the methods detailed herein, that the invention is not limited to treatment of a disease or disorder that is already established. Particularly, the disease or disorder need not have manifested to the point of detriment to the subject; indeed, the disease or disorder need not be detected in a subject before treatment is administered. That is, significant disease or disorder does not have to occur before the present invention may provide benefit. Therefore, the present invention includes a method for preventing a disease or disorder in a subject, in that the compositions of the invention, as discussed elsewhere herein, can be administered to a subject prior to the onset of the disease or disorder, thereby preventing the disease or disorder. The preventive methods described herein also include the treatment of a subject that is in remission for the prevention of a recurrence of a disease or disorder. One of skill in the art, when armed with the disclosure herein, would appreciate that the prevention of a disease or disorder encompasses administering to a subject a composition as a preventative measure against the disease or disorder.

Methods of Assessing

The present invention also relates to compositions and methods for assessing whether a molecule, such as a protein, is capable of transiting to the cytosol of cells. Modified protein compositions of the invention have the property of being able to cross a cell membrane and transit to the cytosol of a cell. Thus, in various embodiments, the invention includes methods of determining whether a modified protein is able to reach the cytosol of a cell, methods of quantifying the extent to which a modified protein is able to reach the cytosol of a cell, methods of assessing how efficiently a modified protein is able to reach the cytosol of a cell, and methods of comparing how well various modified proteins are able to reach the cytosol of a cell.

In some embodiments, the modified protein is a Dex-tagged, or Dex-labeled, modified protein. A Dex-tagged, or Dex-labeled, modified protein is a modified protein that has dexamethasone, or an analogue thereof, attached to it. In some embodiments, the invention is a cell comprising a Gal4-driven reporter gene and an artificial transcription factor, wherein the artificial transcription factor comprises a glucocorticoid receptor ligand-binding domain variant (GR), a Gal4 DNA binding domain (Gal4), and a VP16 transactivation domain (VP16). In another embodiment, the invention is a method that includes the step of providing at least one cell that comprises a Gal4-driven reporter gene and an artificial transcription factor, wherein the artificial transcription factor comprises a glucocorticoid receptor ligand-binding domain variant (GR), a Gal4 DNA binding domain (Gal4), and a VP16 transactivation domain (VP16). In some embodiments, the at least one cell is contacted with a Dex-tagged modified protein, and the level of Gal4-driven reporter gene expression in the cell that was contacted with the Dex-tagged modified protein is measured. When the level of Gal4-driven reporter gene expression is found to have increased after the cell is contacted with the Dex-tagged modified protein, then the Dex-tagged molecule is determined to have reached the cytosol.

In some embodiments, the glucocorticoid receptor ligand-binding domain (GR) variant comprises a cysteine-to-glycine substitution within the ligand-binding domain, at position 656 (C656G), relative to the rat GR.

Reporter genes useful in the methods of the invention include any reporter gene that expresses a gene product that can be detected. In some embodiments, the reporter gene is eGFP.

In some embodiments, the at least one cell is transiently transfected with a nucleic acid expressing an artificial transcription factor. In other embodiments, the at least one cell is stably transfected with a nucleic acid expressing an artificial transcription factor. In some embodiments, the at least one cell is transiently transfected with a nucleic acid expressing a Gal4-driven reporter gene. In other embodiments, the at least one cell is stably transfected with a nucleic acid expressing a Gal4-driven reporter gene.

Any suitable cell type can be used in the methods of the invention. In some embodiments, the cell type that is used is one of U2OS, HeLa, Saos-2, and HEK293T.

In another embodiment, the invention is a cell comprising a fusion protein comprising a detectable marker, such as eGFP, and a glucocorticoid receptor ligand-binding domain (GR) variant. In another embodiment, the invention is a method that includes the step of providing at least one cell comprising a fusion protein comprising a detectable marker, such as eGFP, and a glucocorticoid receptor ligand-binding domain (GR) variant. In some embodiments, the at least one cell is contacted with a Dex-tagged modified protein, and the level of the detectable marker (e.g., eGFP) present in the nucleus is measured and compared with level of the detectable marker (e.g., eGFP) present in the cytosol. When the Dex-tagged modified protein is able to reach the cytosol, the level of the detectable marker (e.g., eGFP) in the nucleus will increase, as compared with the level of the detectable marker (e.g., eGFP) in the nucleus before the cell was contacted with the Dex-tagged modified protein. Thus, in some embodiments, the relative levels of the detectable marker (e.g., eGFP) in the nucleus and the cytosol of a cell after it is contacted with the Dex-tagged modified protein is compared with the relative levels of the detectable marker (e.g., eGFP) in the nucleus and the cytosol of the cell before it was contacted with the Dex-tagged modified protein.

In some embodiments, the glucocorticoid receptor ligand-binding domain (GR) variant comprises a cysteine-to-glycine substitution within the ligand-binding domain, at position 656 (C656G), relative to the rat GR.

Any suitable cell type can be used in the methods of the invention. In some embodiments, the cell type that is used is one of U2OS, HeLa, Saos-2, and HEK293T.

In some embodiments, the at least one cell is transiently transfected with a nucleic acid expressing a fusion protein comprising a detectable marker, such as eGFP, and a glucocorticoid receptor ligand-binding domain (GR) variant. In other embodiments, the at least one cell is stably transfected with a nucleic acid expressing a fusion protein comprising a detectable marker, such as eGFP, and a glucocorticoid receptor ligand-binding domain (GR) variant.

Any method suitable for detecting or quantifying the detectable marker can be used to detect or quantify the detectable marker in the methods of the invention described herein. In some embodiments, the level of the detectable marker (e.g., eGFP) is detected or quantified using at least one technique selected from the group consisting of epifluorescence microscopy and fluorescence activated cell sorting.

Kits

Any of the compositions and methods described herein can be provided in the form of a kit. In various embodiments, a modified protein fusion molecule, and/or an MPD and/or a cargo domain are supplied in a kit. The cargo domain can be a small molecule (e.g., a radionuclide, a fluorescent marker, a dye, or a pharmaceutical agent), a protein (e.g., an immortalizing agent, an anti-apoptotic agent, an enzyme, an oncoprotein, a cell cycle regulatory protein, or an antibody), or a nucleic acid (e.g., RNA, DNA, and cDNA). The MPD and cargo domain can be supplied in single or divided aliquots, in single or divided containers. Written instructions can be included for assembling a MPD-cargo domain complex and/or for using the complex. The instructions can be on the label or container. The instructions may simply refer a reader to another location such as a website or other information source.

In another embodiment, a cell comprising a Gal4-driven reporter gene and an artificial transcription factor, wherein the artificial transcription factor comprises a glucocorticoid receptor ligand-binding domain variant (GR), a Gal4 DNA binding domain (Gal4), and a VP16 transactivation domain (VP16), is provided in a kit of the invention. Written instructions can be included for the use of the cell in one or more methods of the invention described herein. The instructions can be on the label or container, or the instructions may simply refer a reader to another location such as a website or other information source.

In one embodiment, a cell comprising a fusion protein comprising a detectable marker, such as eGFP, and a glucocorticoid receptor ligand-binding domain (GR) variant, is provided in a kit of the invention. Written instructions can be included for the use of the cell in one or more methods of the invention described herein. The instructions can be on the label or container, or the instructions may simply refer a reader to another location such as a website or other information source.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Arginine Topology Controls Escape of Minimally Cationic Proteins from Early Endosomes to the Cytoplasm Proteins capable of crossing biological membranes show great promise as therapeutics as well as agents for delivery of macromolecules, such as siRNA, to the cytoplasm of target cells. In a broader sense, proteins that effectively traffic across membranes offer the potential to illuminate fundamental principles of cell biology. In the studies described herein, two small folded proteins were identified, the cationic miniature protein 5.3 and the zinc finger module ZF5.3, that achieve cytosolic access through rapid internalization and efficient escape from Rab5+ endosomes. The trafficking pathway that was mapped for these molecules is similar to that taken by botulinum toxin and anthrax toxins, which also escape from early endosomes (Simpson, 2004, Annu. Rev. Pharmacol. Toxicol. 44:167-193). The pathways followed by Tat (SEQ ID NO:67) and Arg8 (SEQ ID NO:68), however, resemble those of SV40 (Vonderheit and Helenius, 2005, Plos Biol. 3:e233), and HIV-1 (Vidricaire and Tremblay, 2005, J Immunol. 175:6517-6530), and require transport beyond early Rab5+ endosomes to gain cytosolic access. This difference reveals that the ability of 5.3 and ZF5.3 to rapidly escape from early endosomes is a unique feature, not shared by canonical cell penetrating peptides, and implies the existence of distinct signals, encodable within short peptide sequences, that favor early versus late endosomal release. Identifying these signals and understanding their mechanistic basis will illustrate how cells control the movement of endocytic cargo and allow researchers to engineer molecules to follow a desired delivery pathway for rapid cytosolic access. Collectively, the investigations described herein support the optimization of well-folded functional cell penetrating proteins useful as pharmacologic tools and capable of modulating cytoplasmic protein function.

The interfaces that form between and among proteins and DNA—often large, flat, and polar—do not resemble those that bind small molecule substrates or traditional inhibitors (Rutledge et al., 2003, J Am Chem Soc. 125:14336-14347). Targeting these 'undruggable' interfaces is a task well suited to protein and peptide ligands, but can only be successful if such molecules reach their cytosolic targets. Unfortunately, the very properties that endow peptide mimetics with their promise—size and polarity—are precisely those properties forbidden by Lipinski's rules (Lipinski et al., 2001, Adv Drug Deliv Rev. 46:3-26). The challenge, therefore, is to identify the determinants that guide the uptake of peptide-like molecules and the mechanisms through which they gain cytosolic access, generating a new set of rules applicable to large peptidic molecules and their mimetics. Advancing this goal has been constrained by the absence of a rapid and robust assay capable of distinguishing between peptide-like molecules that remain trapped within endosomes and those that escape into the cytosol.

To learn more about the structural determinants of cytoplasmic access, a set of miniature proteins were designed that differed in the number and density of α-helical arginine side chains, and tracked their passage into the cell. Using low concentrations (1 μM) of fluorophore-conjugated variants, it was found that a minimum of 4 α-helical arginines was required for uptake, and that cell uptake was enhanced when the arginines were clustered on the same α-helix face. Next, a novel and rapid assay for evaluating cytoplasmic access revealed that of four cationic miniature proteins taken up by cells, only one reaches the cytosol. This miniature protein, which is named 5.3, possesses a distinct array of five dispersed α-helical arginines. Live cell confocal microscopy revealed that fluorophore-labeled 5.3 (5.3R) is taken up by an endocytic pathway that includes Rab5+ and Rab7+ endosomes. This pathway is shared by Tat (SEQ ID NO:67), Arg8 (SEQ ID NO:68), and cationic miniature proteins that do not reach the cytosol. However, for 5.3, Tat (SEQ ID NO:67) or Arg8 (SEQ ID NO:68) to gain cytosolic access, active endocytosis and endosomal acidification were required. These data indicate that none of the molecules evaluated could directly cross the plasma membrane; rather, they reach the cytoplasm by escaping from intracellular vesicles. In addition, it was found that unlike Tat (SEQ ID NO:67) or Arg8 (SEQ ID NO:68), which require vesicle maturation beyond the Rab5+ stage, miniature protein 5.3 accesses the cytosol by crossing specific membrane regions present in early Rab5+ endosomes. Finally, grafting the arginine array present in 5.3 into a well-folded zinc finger domain (Krizek et al., 1991, J Am Chem Soc. 113:4518-4523) successfully endowed this domain with the trafficking properties of 5.3. These experiments demonstrate that discrete arginine arrangements embedded within a well-folded miniature protein can direct cytosolic access by facilitating both efficient uptake and early endosomal escape.

In the studies described herein, developments in automated image analysis and the rapid cytoplasmic-to-nuclear translocation of the glucocorticoid receptor (GR) were utilized to develop an assay that, by monitoring nuclear accumulation of a GR-GFP fusion, reports on the cytoplasmic entry of traditionally impermeant molecules tagged with Dex. This assay offers advantages of both speed and cost over a first-generation assay developed by Kodadek and colleagues (Yu et al., 2005, Nat Biotechnol. 23:746-751), as it provides a readout in living cells within 30 min (as opposed to 48 hours) and eliminates the requirement for cell lysis or costly enzymatic substrates. With this assay, clear differences were measured in the cytosolic localization of four actively endocytosed miniature proteins and 5.3 was identified as a cationic miniature protein whose rapid cytosolic localization is equivalent to or better than Tat (SEQ ID NO:67) and Arg8 (SEQ ID NO:68). The large differences in cytosolic localization among the set of closely related miniature proteins emphasizes that distinct structural determinants control both endocytic uptake and endosomal release. Uptake is favored by clustered α-helical arginine side chains, whereas release requires a more dispersed arginine array.

Figure 7:
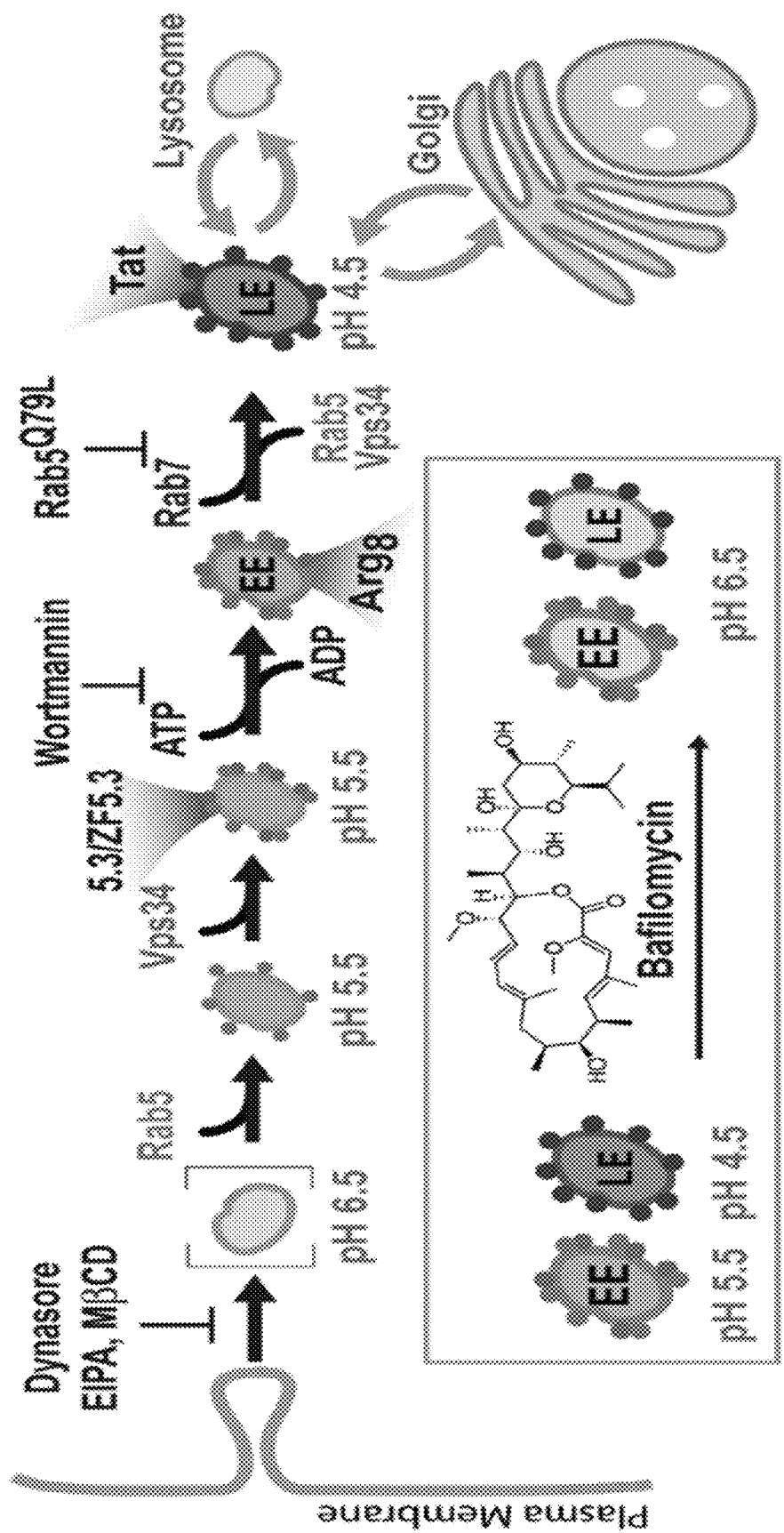
FIG. 7 depicts a scheme illustrating the stepwise pathway of traffic taken by 5.3, ZF5.3, Tat and Arg8 from the cell exterior into the cytosol. The path taken by 5.3, ZF5.3, Tat and Arg8 from the cell exterior to the cytosol begins with and requires endocytosis from the plasma membrane. 5.3, ZF5.3, Tat, and Arg8 bind to the cell surface and traffic into early endosomes, which rapidly acquire Rab5, followed by Vps34, a lipid kinase responsible for generating PI3P. Inhibition of Vps34 by Wortmannin fails to block escape of 5.3 or ZF5.3 (see FIGS. 5 and 6), indicating these molecules can escape vesicles prior to this stage. Rab5 and PI3P recruit Rab5 effectors, beginning endosome maturation. Recruitment of Rab7 leads to the formation of late endosomes (LE). The Rab5+-to-Rab7+ transition, which is blocked following transfection with Rab5Q79L, is not required for 5.3 or ZF5.3 to access the cytoplasm, but decreases the escape of Tat (see FIG. 5), suggesting Tat escapes later in the endocytic pathway. Arg8 escape is blocked by wortmannin treatment but not by transfection with Rab5Q79L, suggesting escape begins late in the Rab5 stage but prior to the Rab7 stage. Endosomes are progressively acidified, a process blocked by bafilomycin (structure shown) and required for 5.3, ZF5.3, Tat, and Arg8 to reach the cytoplasm. The amino acid sequence of Arg8 is provided in SEQ ID NO:68.

Coupling this new assay for cytosolic localization with live cell confocal microscopy allowed the further clarification of contrasting models for the intracellular pathway taken by cationic miniature proteins and peptides en route to the cytoplasm. At low concentrations, none of the molecules studied here crossed the plasma membrane directly. Miniature protein 5.3, with the lowest charge density, enters into and efficiently escapes from early (Rab5+) endosomes. In contrast, Tat (SEQ ID NO:67) and Arg8 (SEQ ID NO:68), which are also present in Rab5+ vesicles, require delivery to downstream Rab7+ vesicles or the recruitment of Rab5 effectors in order to reach the cytoplasm (FIG. 7). Although not wishing to be bound by any particular theory, the differences in arginine/lysine number and orientation in 5.3, Tat (SEQ ID NO:67), and Arg8 (SEQ ID NO:68) will likely affect their side chain pKa values and thus the overall charge of each molecule at any given pH.

Although not wishing to be bound by any particular theory, the findings described herein are consistent with the explanation that the distinct arginine array in 5.3 favors formation of a critical protonated species within the early endosome (pH≈6.5), whereas the lower pH present in lysosomes may be required to generate an equivalent state for Tat (SEQ ID NO:67) and Arg8 (SEQ ID NO:68). Alternatively, the findings described herein are consistent with the explanation that the distinct arginine array in 5.3 represents an export signal for cellular machinery that has yet to be identified.

The materials and methods of this example are now described.

Cell Culture and Transfections

HeLa cells (ATCC, Manassas, Va.) were grown in T-75 culture flasks containing Dulbecco's Modified Essential Medium (DMEM, Gibco Cat. #11995-065) supplemented with 10% FBS, and 100 U/mL each Penicillin and Streptomycin. Transient transfections were performed using Fugene 6 or XtremeGene HP (Roche) and protocols recommended by the manufacturer. Plasmids encoding Rab5-GFP and Rab5Q79L-GFP were gifts from Pietro DeCamilli. A plasmid containing Rab7-GFP was a gift (Addgene plasmid #28047). A plasmid containing GalT-EGFP was a gift (Addgene plasmid #11937). A plasmid containing the glucocorticoid receptor fused to EGFP (pK7-GR-GFP) was a gift (Addgene plasmid #15534).

Analysis of Surface Binding and Cell Uptake

HeLa cells grown to ~90% confluency were dissociated from flasks by incubation for 15 min at 37° C. with 2 mL PBS, 1 mM EDTA, 1 mM EGTA. Cells were collected in warmed media, and aliquots (150 µL, 200,000 cells) distributed to 96 well plates. The cells were incubated at 4° C. or 37° C. for 10 min, 1 µM fluorescently labeled peptide was added, and incubation continued for an additional 30 min. Cells were then washed twice with DMEM+10% FBS and treated with trypsin (30 µl, per well, 0.05%, 37° C.×10 min) before resuspending in 300 µl, PBS. Cells were analyzed by flow cytometry using an Accuri C6 flow cytometer. To confirm that trypsin treatment removed fluorescently labeled peptide remaining on the cell surface, HeLa cells were treated with 1 µM miniature protein or peptide at 4° C. to inhibit endocytosis. After washing twice, the cells were then treated with trypsin (30 µL, 0.05%, 37° C.×10 min) or PBS as a control. Cells were then resuspended in 300 µL PBS before analysis by flow cytometry. Data presented are the mean±SEM for 4 biological replicates measuring the mean fluorescence intensity of 30,000 cells. Dead cells defined by forward and side scatter were excluded.

Colocalization of Miniature Proteins with Alexa-488-Transferrin and Rab-GFP Fusions To examine the colocalization of rhodamine labeled miniature proteins or peptides with Alexa-488-transferrin (Tf488), HeLa cells were plated (200 µl, $10^4$ cells/well, 96 well glass bottom plates, Matrical) the day prior to experiments. The media was replaced with 150 µL Hepes-Krebs-Ringer's (HKR) buffer (140 mM NaCl, 2 mM KCl, 1 mM CaCl2, 1 mM MgCl2, 10 mM Hepes pH 7.4) containing 1 µM miniature protein or 25 nM Alexa-488-transferrin (Molecular Probes) and the cells incubated at 37° C. for 30 min. The cells were then rinsed twice with 200 µL, HKR buffer and nuclei were labeled by overlaying 200 µL HKR containing 300 nM Hoechst 33342 (Molecular Probes Cat. # H3570) for 5 minutes. Images of cells were acquired using a PerkinElmer LiveView spinning disk confocal microscope fitted with a 60×1.2 NA objective. Colocalization with Rab-GFP fusions was examined in an analogous way using HeLa cells transfected with the appropriate expression plasmid.

Effects of Inhibitors on Cell Uptake

HeLa cells grown for 24 h in glass bottom plates were incubated with HKR buffer, or HKR buffer containing 80 µM dynasore, 50 µM N-ethyl-isopropyl-amiloride, or 5 mM methyl-β-cyclodextrin for 30 min at 37° C. prior to the addition of 1 µM rhodamine-labeled miniature protein or peptide (Tat (SEQ ID NO:67) and Arg8 (SEQ ID NO:68)). The cells were washed twice with DMEM, the nuclei labeled with Hoescht, and images acquired as described above for colocalization experiments.

GR-GFP Translocation Assay

HeLa cells transfected with pK7-GR-GFP were plated in Matrical plates as described above. To label nuclei, the media was replaced with HKR buffer containing 300 nM Hoescht and the cells incubated for 30 min at 37° C. Cells were then treated with 150 µL HKR buffer or HKR buffer containing 1 µM dexamethasone, dexamethasone labeled miniature protein, or dexamethasone labeled peptides for 30 min at 37° C. before epifluorescence imaging. The translocation ratio (the ratio of the median intensities of GFP in the nuclear and surrounding region) for each cell imaged was measured using CellProfiler (Carpenter et al., 2006).

To examine the effects of various inhibitors, HeLa cells transfected and plated as above were pretreated with HKR buffer containing 300 nM Hoescht and 80 µM dynasore, 50 µM N-ethyl-isopropyl-amiloride, 200 nM wortmannin, 200 nM bafilomycin or 5 mM methyl-β-cyclodextrin for 30 min at 37° C., after which was added 1 µM dexamethasone, dexamethasone labeled miniature protein or peptide for an additional 30 min at 37° C. Cells were then analyzed as described above.

To evaluate the requirement of Rab5 activity for the ability of peptides to reach the cytoplasm, HeLa cells were transfected with pGR-mCherry and either Rab5-EGFP or Rab5Q79L-EGFP for 24 hrs before treatment with dexamethasone or dexamethasone labeled miniature proteins or peptides and imaging as described above. Cotransfected cells expressing Rab-GFP fusions and pGR-mCherry were identified via their characteristic pattern of green and red fluorescence. The translocation ratio was determined using median values of mCherry fluorescence within the nucleus and surrounding region using CellProfiler.

Statistical Analysis

Comparisons within groups were made using ANOVA. Pairwise comparisons within groups were made using Bonferroni's post-test after finding a significant difference using ANOVA. P-values are corrected using Bonferroni's method (Shaffer, 1995, Annual Review of Psychology. 46:561-584) so that the family-wise error rate=0.05. Otherwise, comparisons were made using a two tailed t-test.

Materials

Fmoc-protected amino acids and Rink-PAL amide resin were purchased from Novabiochem. All other reagents required for solid phase peptide synthesis were obtained from American Bioanalytical. SDEX was synthesized as previously described.

Miniature Protein Synthesis and Purification

Figure 14:
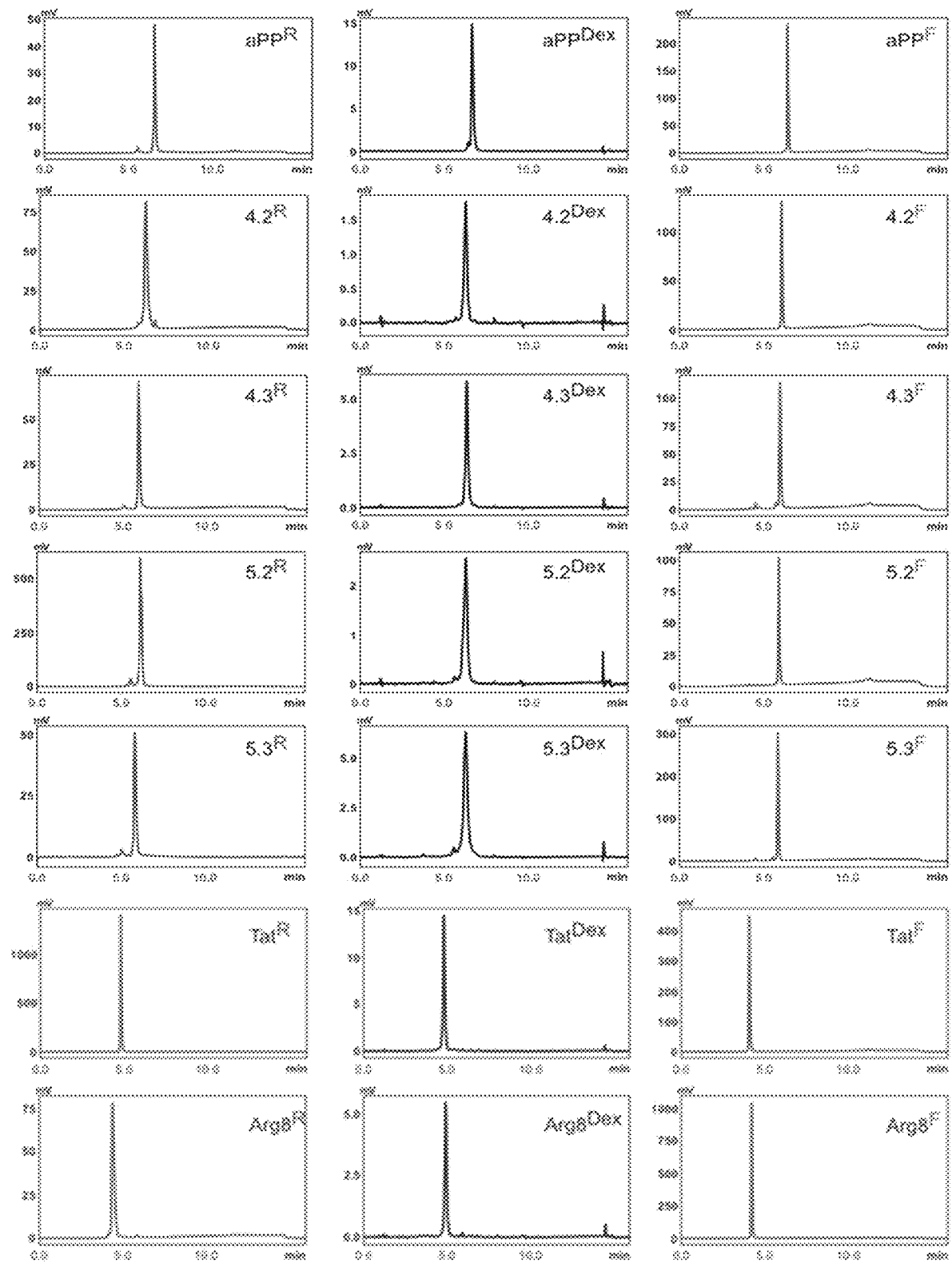
FIG. 14 depicts HPLC traces of labeled proteins and peptides. The amino acid sequence of Arg8 is provided in SEQ ID NO:68.
Figure 16:
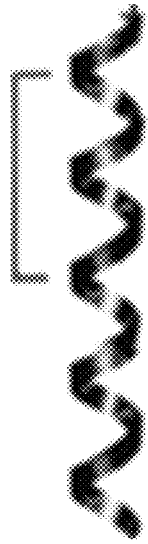
FIG. 16 depicts the results of experiments demonstrating that the rule of five motif improves cytosolic localization (and function) of a highly active but otherwise impermeant stapled peptide.
Figure 17:
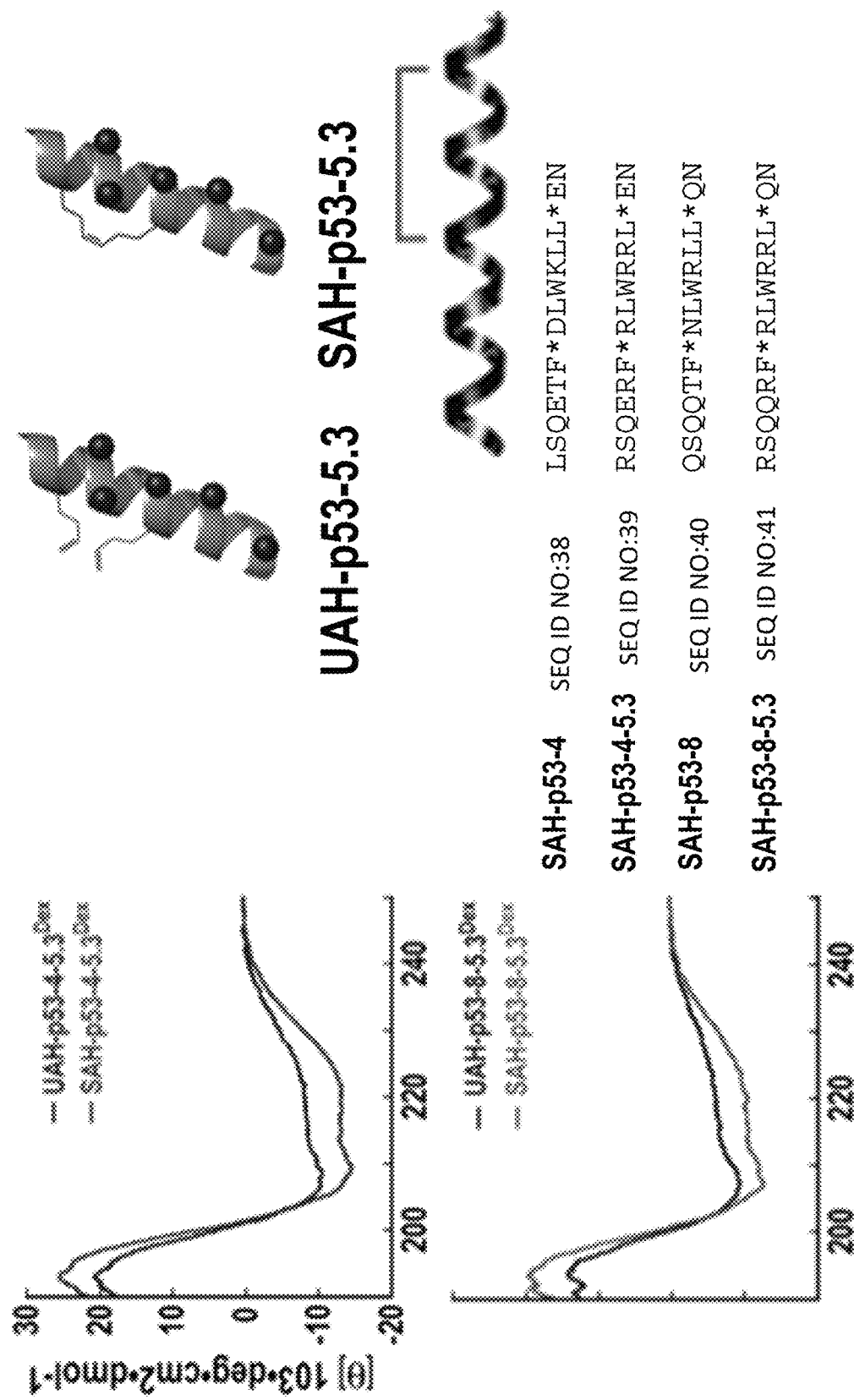
FIG. 17 depicts stapled peptides containing a penta-arg motif retain α-helical structure.
Figure 18:
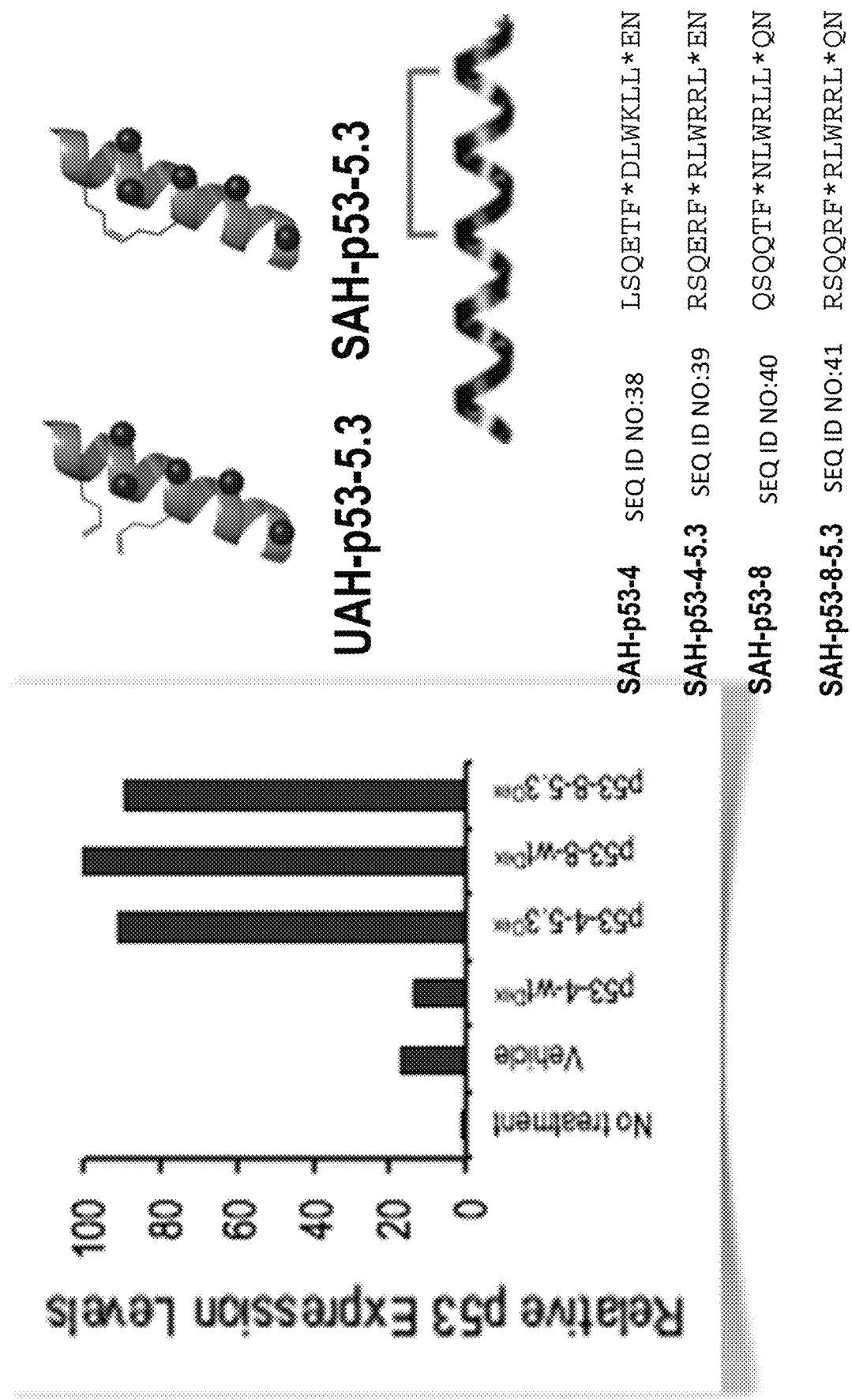
FIG. 18 depicts the results of experiments demonstrating that a penta-arg motif increases the function of an otherwise impermeant stapled peptide.

All miniature proteins and peptides were synthesized using a Liberty Automated Microwave Peptide Synthesizer (CEM) and standard solid phase synthesis techniques. Coupling reactions were performed using 5 equivalents of amino acid, 5 equivalents HBTU, and 10 equivalents of diisopropylethylamine in DMF. FMOC groups were removed using 20% piperidine in DMF containing 0.1 M HOBT to minimize aspartamide formation. Following synthesis, the peptides were cleaved from the resin by adding 5 mL of a solution containing 95% TFA, 2.5% water, 2.5% TIPS and incubating at 38° C. for 30 min using a microwave accelerator (MARS system, CEM). The solution containing the crude peptide was precipitated by the addition of 40 mL cold ether. The precipitate was dried under a nitrogen stream and lyophilized before purification via reverse phase HPLC (YMCbasic column, 150 mm×10 mm ID) using a linear gradient of CH3CN in water (both acidified with 1% TFA). Purified miniature proteins or peptides were collected and lyophilized, then reconstituted in water and kept at −4° C. protected from light. The purity and identity of purified miniature proteins was characterized by analytical HPLC (>95% in all cases) and either a Voyager (Applied Biosystems) MALDI-TOF (matrix-assisted laser desorption-ionization time-of-flight) spectrometer (337 nm laser, α-cyano-4-hydroxycinnaminic acid matrix), or a Waters QTof LC-MS. Molecular formulas, calculated masses, and measured (m/z) ratios of polypeptides and miniature protein domains are found in Table 1. HPLC traces of labeled miniature proteins and peptides are shown in FIG. 14.

Fluorescein Labeled Miniature Proteins

Fluorescein labeled miniature proteins were generated from purified peptides containing an appended C-terminal cysteine residue. The purified unlabeled product was reacted with 5-(iodoacetamido)fluorescein to generate the fluorescein labeled miniature protein as follows. To 500 μL of a 100 mM phosphate buffer, pH 7.25 was added 1 μmol of the miniature protein, then water to a total volume of 2.5 mL. Separately, 5 mg of 5-(iodoacetamido)fluorescein (Sigma Cat. #I9271) was dissolved in 2.5 mL DMF. This DMF solution was added to the aqueous miniature protein solution and the reaction was incubated in the dark at 25° C. for 2 hours. To generate unlabeled miniature proteins, the C-terminal cysteine was capped by reaction with iodoacetamide under analogous conditions. The reaction mixture was purified using reverse phase HPLC using the column and solvent system described above.

Rhodamine labeled miniature proteins and peptides. Rhodamine labeled miniature proteins were generated by carrying out labeling reactions on resin using an appended N-terminal lysine. For this purpose an amino acid monomer was employed in which Nα is BOC-protected and NE is protected with an FMOC group. The NE was deprotected using microwave acceleration and incubating the resin twice with 20% piperidine in DMF at 80° C. for 7 min. The resin was then washed thoroughly with DMF. To label peptides with tetraethyl rhodamine, to the deprotected resin was added 10 eq of Lissamine Rhodamine B sulfonyl chloride and 10 eq of diisopropylethylamine in 5 mL DMF at room temperature overnight. The resin was thoroughly washed with DMF and DCM before global deprotection and cleavage using the conditions for unlabeled peptides described elsewhere herein. Crude rhodamine labeled peptide was precipitated in 40 mL of cold ether and lyophilized. Peptides were purified by reverse phase HPLC as described above. Peptides lyophilized from HPLC solvents were stored in water at 4° C. protected from light.

SDEX Labeled Miniature Proteins and Peptides

SDEX labeled miniature proteins and peptides were generated in a manner analogous to the generation of rhodamine labeled miniature proteins; following peptide synthesis and additional amino acid, Nα-BOC-NE-FMOC-lysine, was coupled to the N-terminus of the peptide Nα-BOC-NE-FMOC-lysine. Deprotection of NE was carried out using microwave acceleration by incubating the resin twice with 20% piperidine in DMF at 80° C. for 7 min. The resin was then washed thoroughly with DMF. To the deprotected resin was added 5 eq SDEX, 5 eq HATU, 5 eq of HOAT, 5 eq of DIPEA, and 5 eq of 2,6-lutidine in 5 mL DMF. The reaction was shaken overnight at room temperature. The resin was thoroughly washed with DMF and DCM before global deprotection and cleavage using the conditions for unlabeled peptides described above. Crude SDEX labeled peptide was precipitated in 40 mL of cold ether and lyophilized. Peptides were purified by reverse phase HPLC as described above. Peptides lyophilized from HPLC solvents were stored in water at 4° C. protected from light.

Concentration Determination

Concentrations of labeled miniature proteins were calculated using the extinction coefficients of the strongest absorbing chromophores. In the case of unlabeled miniature proteins, the extinction coefficient was determined directly from the amino acid sequence. In the case of labeled peptides, fluorescein absorption at 500 nm in 8 M urea, 100 mM Tris-HCl, pH 9.0 was measured using the molar extinction coefficient 78,000 M-1 cm-1 at 500 nm (Invitrogen). The concentration of rhodamine labeled variants was determined in water using an extinction coefficient of 87000 M-1 cm-1. The concentration of SDEX labeled variants were determined using an extinction of 12000 M-1 cm-1 at 242 nm in DMSO1.

Circular Dichroism

CD spectra of unlabeled aPP-based miniature were recorded from samples containing 25 μM peptide in PBS as described (Luedtke et al., 2007, Nat Chem Biol. 3:779-784). CD spectra of ZF and ZF5.3 in the presence and absence of Zn2+ were recorded from solutions of peptide (12.5-25 μM) dissolved in 10 mM argon-purged Tris-HCL (pH 8.0) in the presence or absence of 0.5 mM dithiothreitol and 2 eq. ZnC12. Samples were incubated for 30 min at RT and analyzed on a Jasco J-810-150S spectropolarimeter. Final plots show background-normalized averages of six scans.

pGR-mCherry Vector Construction

The full length glucocorticoid receptor (NR3C1) was subcloned into pmCherry-N1 (Invitrogen), generating a C-terminal fluorescent protein fusion, by amplifying the gene from pK7-GR-GFP using the following PCR primers containing Sac1 and BamH1 restriction sites: Forward=CCG GAC TCA GAT CTC GAG CTC AAG CTT CGA ATT CGC CAT GGA CTC CAA AGA ATC ATT AAC TCC TGG TAG AGA AGA AAA CCC (SEQ ID NO:1). Reverse=GCG CGG ATC CCG CGG CTT TTG ATG AAA CAG AAG TTT TTT GAT ATT TCC ATT TGA ATA TTT TGG TAT CTG ATT GG (SEQ ID NO:2). The amplified PCR product was digested and ligated into the multiple cloning site of pmCherry-N1 digested with the same restriction enzymes.

Colocalization Analysis

Colocalization between rhodamine and fluorescein labeled miniature proteins and peptides, or between rhodamine labeled miniature proteins and markers of endocytosis was completed using confocal microscopy. Live cell confocal microscopy was conducted using a PerkinElmer LiveView spinning disk confocal microscope fitted with heated microscope enclosure (maintained at 37° C.), a 60×1.2 NA objective, laser illumination, a Nipkow CSU-1× spinning disk, and a Hammamatsu CS9100 EMCCD camera operated using Velocity software. Alexafluor-488-transferrin was detected using a 488 nm laser and a 520 nm long pass filter; tetraethylrhodamine and Alexafluor-546-transferrin were detected using a 546 nm laser line and a 580 nm long pass filter, Hoescht 33342 was detected using a 405 nm laser line and a 450 nm long pass filter. Images were processed for presentation by using the 'subtract background' option and linear contrast adjustments in Image J. All adjustments were applied uniformly to the entire image. Colocalization analysis was performed using the JACOP plugin (Bolte and Cordelières, 2006), available on the ImageJ website. The fraction of rhodamine signal overlapping with EGFP signal (R E G) was calculated using Mander's coefficient and automatic thresholding. Pearson's correlation coefficient (R) was also obtained using the JACOP plugin.

Activation of GR by Dexamethasone Labeled Peptides and Miniature Proteins

HeLa cells transfected with pK7-GR-GFP for 24-36 hr were plated ($10^4$/well in 200 µL) the day prior to experiments in 96 well glass bottom plates (Matrical). The media was replaced with HKR buffer containing 300 nM Hoescht and the cells incubated for 30 min at 37° C. The media was then replaced with 150 µL HKR buffer or HKR buffer containing 1 µM dexamethasone labeled cationic miniature protein or peptides or 1 µM dexamethasone as a positive control. The cells were incubated for a further 30 min at 37° C. before epifluorescence imaging using a Zeiss Axiovert 200M microscope fitted with a mRM digital camera, a 63×1.3NA PlanApo objective and an EXFO-Excite illumination source. Dual color epifluorescence images were acquired using the following filter sets: Hoescht, Zeiss Filter Set #49 (ex G 365 nm, FT 395, em BP 445/50 nm); EGFP, Zeiss Filter Set #44 (ex BP 475/50 nm, FT 500, em BP 530/50 nm).

To examine the effects of various inhibitors on the ability of dexamethasone labeled cationic miniature proteins to activate the glucocorticoid receptor, HeLa cells were transfected and plated as above. Thirty minutes prior to the addition of dexamethasone labeled cationic miniature proteins and peptides the media was replaced with HKR buffer containing 300 nM Hoescht and 80 µM dynasore, 50 µM N-ethyl-isopropyl-amiloride or 5 mM methyl-β-cyclodextrin and the cells incubated for 30 min at 37° C. after which 1 µM dexamethasone labeled miniature protein or peptide was added. Uptake was allowed to proceed for an additional 30 min at 37° C. before analysis by epifluorescence images as described elsewhere herein.

Requirement of RabS Activity for the Ability of Peptides to Reach the Cytoplasm

HeLa cells transfected for 24-36 hr with pGR-mCherry and either Rab5-GFP or Rab5Q79L-GFP were plated ($10^4$/well in 2004) the day prior to experiments in 96 well glass bottom plates (Matrical). The cells were washed with HKR buffer and the nuclei labeled using Hoescht as above. Then 150 µL HKR buffer or HKR buffer containing 1 µM dexamethasone labeled cationic miniature protein or peptides or 1 µM dexamethasone as a positive control was overlaid into the well. The cells were incubated for a further 30 min at 37° C. before imaging. Cells that had been cotransfected with EGFP fusions were identified via their characteristic pattern of green and red fluorescence. To evaluate the extent of GR activation, epifluorescence images were obtained as described above, except the fluorescence of pGR-mCherry was also visualized using Zeiss Filter Set #43 (ex BP 545/25 nm, FT 570, em BP 605/70 nm).

Image Analysis Using CellProfiler

The image analysis algorithm used by CellProfiler is customizable and contained within a 'Pipeline' that describes a series of image manipulation and evaluation steps, such as reading the image, adjusting the intensity, and identifying objects. Each step has several options. It was found that the translocation ratio was generally robust, provided nuclei were accurately identified. Using the image of Hoescht fluorescence and Otsu's method of automatic thresholding, nuclei were identified and segmented using 3 class thresholding. The middle class was assigned to background. Closely approximated objects were separated using 'Laplacian of Gaussian' modeling, and touching nuclei were divided using the 'shape' option. Nuclear regions were expanded by 2 µm to generate an enlarged region. The nuclear region was subtracted from enlarged region to generate a ring surrounding the nucleus (surround). The diameter of the surrounding region was chosen to be 2 µm larger than the nucleus, within the range (1-3 µm) used by previously reported high content screens (Ding et al., 1998, J Biol Chem. 273:28897-28905; Peeraniet al., 2007, EMBO J. 26:4744-4755). The ratio of the median intensities of the nuclear and surrounding region of the GFP or mCherry (as appropriate) image were collected for every cell examined. Those cells falling below a threshold of intensity (10% of the maximum intensity of the image) were discarded as 'untransfected'. Typically, 20-60 transfected cells from 15-30 images were examined for each experimental condition.

Examination of Membrane Integrity

The loss of membrane integrity was examined by visualizing nuclear fluorescence after exposure to Sytox Blue (Invitrogen), a cell impermeant dye that fluoresces brightly when complexed with DNA. Syto Orange 85 (Invitrogen) was used as a cell permeable counter stain. HeLa cells plated in glass bottom microtitre plates were exposed for 30 min at 37° C. to 1 µM dexamethasone labeled cationic miniature protein or peptide in HKR buffer containing 1 µM Sytox Blue and 1 µM Syto Orange. Buffer without peptide or containing 10 µg/mL Saponin was used as negative and positive controls respectively. After incubation, cells were washed briefly in HKR buffer, and examined immediately via epifluorescence microscopy (Zeiss Axiovert 200M). Sytox Blue fluorescence was visualized using Filter Set 49, Syto Orange 85 was visualized using Filter Set 43. Images were analyzed using ImageJ.

Competition Between Dexamethasone Labeled Miniature Proteins or Peptides and Fluormone™ for Binding to the Glucocorticoid Receptor Differences in the affinities of dexamethasone-labeled molecules for the human glucocorticoid receptor were assessed using the Glucocorticoid Receptor Competitor Assay Kit (Invitrogen). Varying concentrations of dexamethasone-labeled miniature protein or peptide (or dexamethasone as a control) were suspended in 48 µL Screening Buffer (10 mM NaPO4, pH 7.4; 20 mM Na2MoO4; 1 mM EDTA, 2% DMSO) and incubated with 2.5 nM Fluormone GS1 and 4 nM recombinant human GR for 3 h in the dark at RT. Following incubation, the fluorescence polarization of each solution was measured on an Analyst AD plate reader (LJL Biosystems). Each data point represents the average fluorescence polarization (+standard deviation) of three separate experiments. Data were plotted as polarization (mP) vs. Log [inhibitor] and fit to the following equation using GraphPad software (Prism):

$$mP = P\text{min} + [(P\text{max} - P\text{min})/(1 + 10^{\text{Log}([C]) - \text{Log}(IC50)})]$$

where mP is the polarization of the sample, [C] is the concentration of the test compound, Pmax is the polarization of the sample when no competitor is added, and Pmin is the polarization that represents maximum competition.

Peptide Degradation

Approximately 200,000 HeLa cells were treated with rhodamine labeled cationic miniature proteins and peptides as described for experiments using flow cytometry to measure peptide uptake. These cells were pelleted in 96 well microtitre plates (300 g, 3 min) and lysed in 40 μL RIPA buffer (150 mM NaCl, 50 mM Tris pH 7.4, 50 mM EDTA pH 7.4, 0.1% SDS, 1% Triton X-100) on ice for 30 min. The insoluble material was cleared from the cell lysate via centrifugation (10,000 g, 10 min) and 20 μL of the supernatant was diluted into 400 μL of 15% CH3CN in water. These samples were analyzed via reverse phase HPLC (Shimadzu Instruments) fitted with a fluorescence detector and a C18 column (Poroshell 120 SB-C18, 2.7 μm, 100 mm×3 mm ID, Agilent).

Preparation and Analysis of Cytosolic Extracts

To generate cytosolic extracts, HeLa cells were treated with streptolysin O (SLO), a well characterized bacterial toxin that creates pores in the plasma membranes of target cells (Walev et al., 2002, FASEB 16:237-239). Previous studies have found that at 4° C., SLO binds to cells but no permeabilization occurs (Hugo et al., 1986, Infect Immun 54:641-645). Moreover, when the toxin is added to cultured cells at 4° C. and washed with PBS before raising the temperature to 37° C., pores are created only in the plasma membrane and the release of ER, golgi, or endolysosomal contents are avoided (Androlewicz et al., 1993, Proc Natl Acad Sci USA 90:9130-9134).

First, selective release of the cytoplasmic contents of HeLa cells using the published procedures was verified. HeLa cells were treated with 20 μg/mL SLO in PBS containing 5 mM DTT (20 min, 4° C.), washed (three PBS washes, 150 μL each), resuspended in PBS, and incubated at 37° C. for 15 min, after which 1.5 μM propidium iodide (PI), a marker of permeabilized cell membranes, was added. Under these conditions, 89 to 95% of the cells accumulated PI (FIG. 13B), indicating that the plasma membrane had been disrupted.

To confirm that these conditions did not breach the integrity of lysosomal membranes, 2.5×105 HeLa cells were treated with SLO at 4° C., washed, resuspended in PBS, and incubated at 37° C. for 15 min as described above. The cells were then pelleted by centrifugation (3 min, 300 g) the supernatant removed and recovered, and after which the cell pellet was treated with detergent lysis buffer (1% SDS in PBS) to solubilize the membranes. Total cell lysate from an equal number of HeLa cells that were not treated with SLO served as a positive control. Incubation of these three fractions (total cell lysate, supernatant from SLO treated cells, and the solubilized cell pellet) with 7.5 mM 4-nitrophenyl-N-acetyl-β-D-glucosaminide (Sigma-Aldrich), a chromogenic substrate for the lysosomal enzyme β-hexosamididase, confirmed that >95% of the total hexoasamididase activity remained associated with the cell pellet and that <5% was released (FIG. 13C).

Resistance to Acid Proteases 50 pmol aPPR, 5.2R, 5.3R, ZF5.3R, TatR (SEQ ID NO:67), or Arg8R (SEQ ID NO:68) were incubated with 5 pg cathepsin B, D, or L for 30 min at 37° C. in 10 μL of 20 mM sodium phosphate buffer (pH 5) containing 150 mM NaCl. At the end of the incubation, the reaction was stopped by adding 40 μL of a solution containing a 84:15:1 ratio of water:EtOH:TFA before analysis by HPLC.

Figure 13:
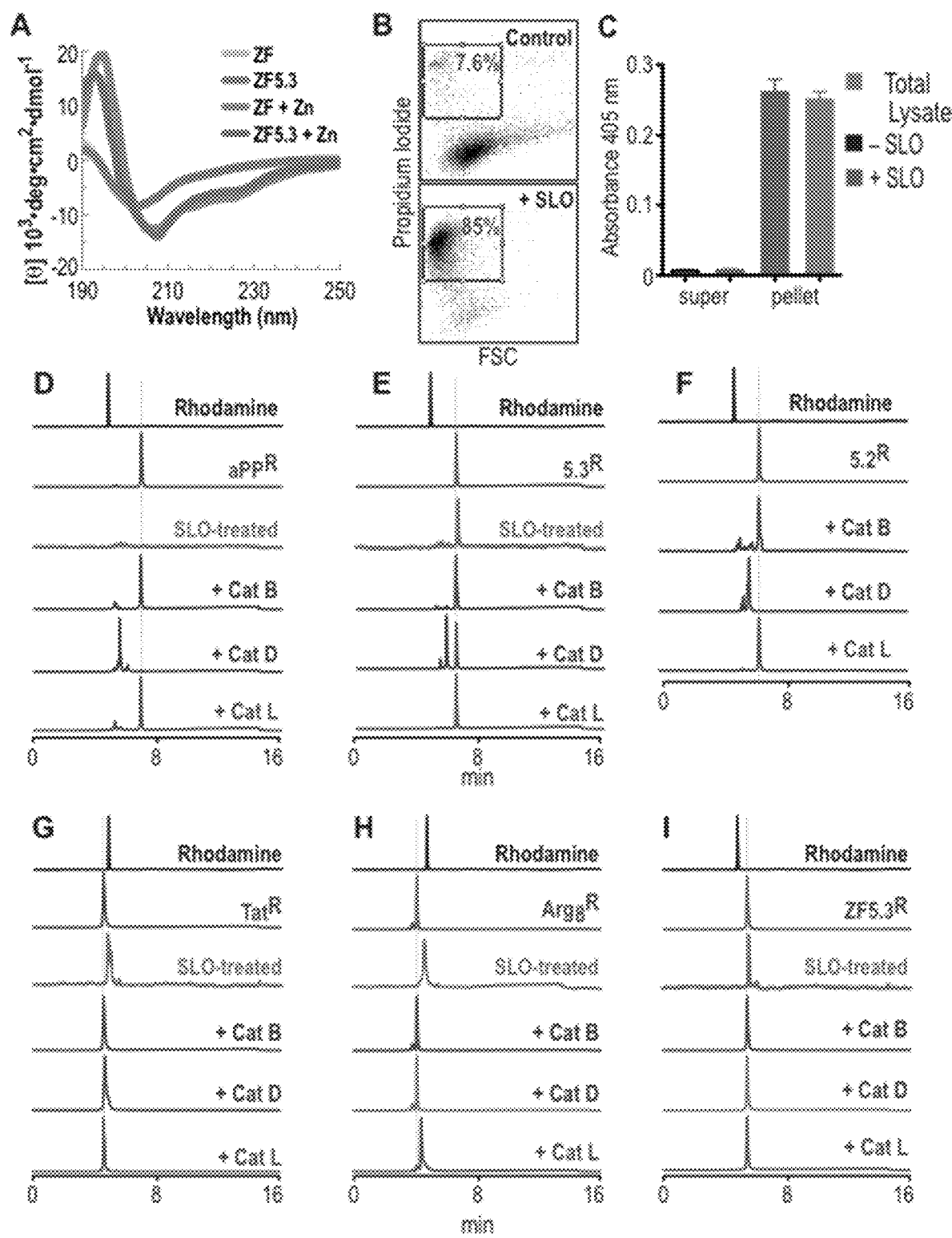
FIG. 13, comprising

Incubation of TatR (SEQ ID NO:67), Arg8R (SEQ ID NO:68), or ZF5.3R for 30 min at 37° C. with cathepsins B, D or L under these conditions led to little or no degradation: the HPLC traces consisted of single peaks with elution times identical to the parent peptides (FIG. 13D-13I). Incubation of 5.2R or 5.3R with Cathepsin L also led to traces identical to the parent peptide. Incubation of 5.2R or 5.3R with Cat B showed the appearance of several additional small peaks, while incubation with cathepsin D led to the complete disappearance of 5.2R and the disappearance of approximately 50% of 5.3R (FIGS. 13E and 13F). The additional peaks seen in these traces are presumably due to degradation products. Thus, if cathepsin D were to cleave 5.3R in cells, evidence of this degradation in the isolated detergent lysates or SLO extracts of HeLa cells treated with 5.3R would be expected (FIG. 13E). However, only unmodified 5.3R in cell lysates or recovered cytosolic extract was observed, so it is unlikely that cathepsin D is actively degrading 5.3R in cells. In addition, the findings that aPPR and 5.2R are also degraded, with equal or greater efficiency than 5.3R, but do not localize to the cytosol (FIG. 3), suggests that the activity seen in the nuclear translocation assay using 5.3Dex (SEQ ID NO:33) is not an artifact due solely to degradation. Finally, it is noted that only the intact peptide is recovered from the cytosol. It is possible that prior to escaping the endosome, 5.3R forms tight complexes with cellular proteins or lipids, and that these cellular components act as competitors for cathepsin D and cathepsin B degradation.

The results of this example are now described.

Miniature Protein Design

Figure 8:
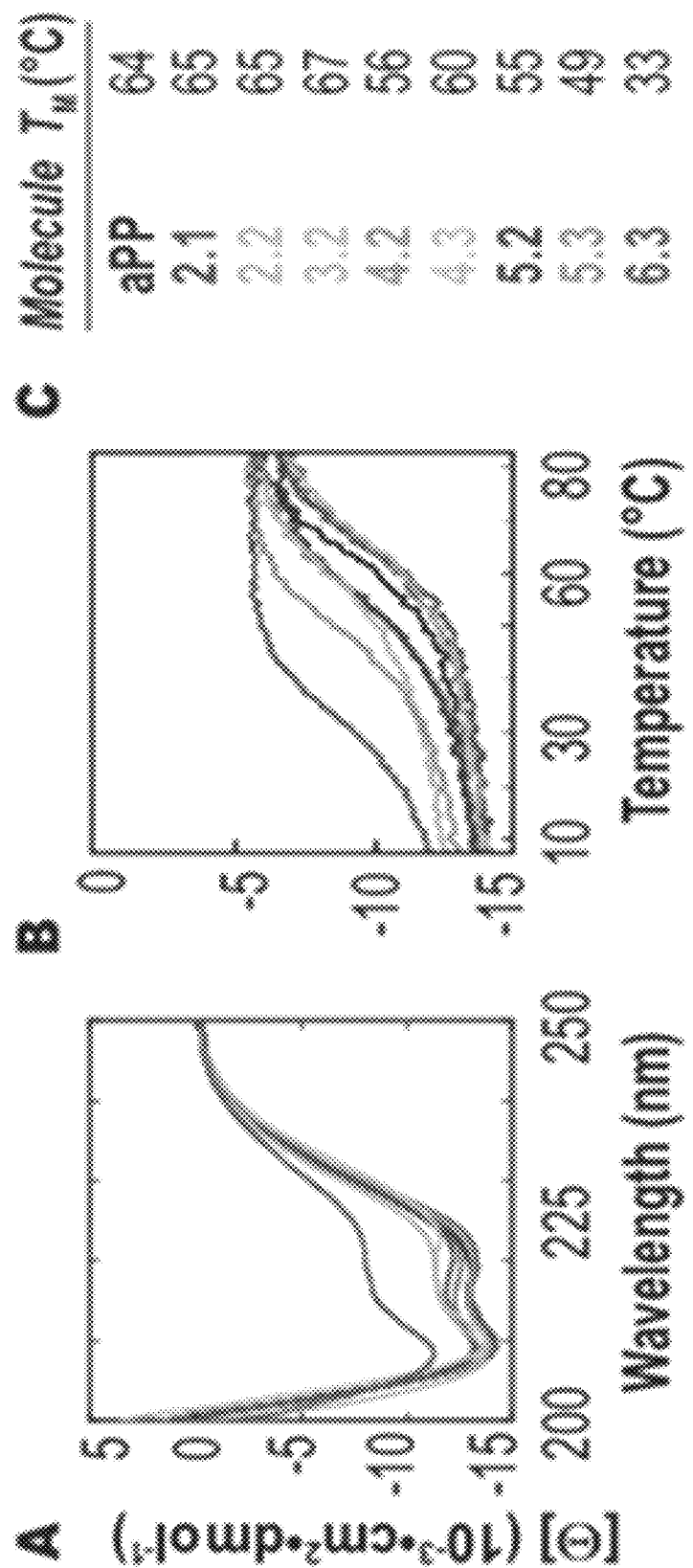
FIG. 8, comprising

To examine the effect of charge density and orientation on cell uptake, eight miniature proteins were prepared containing between one and six arginine residues at various positions on the solvent-exposed α-helical surface of the hairpin fold. These molecules also contained two arginines near the C-terminus (FIG. 1A). Seven of these cationic miniature proteins were characterized by circular dichroism (CD) spectra at 37° C. that were virtually indistinguishable from that of the parent molecule lacking additional arginines, aPP (FIG. 8A). The CD spectra of six were temperature-dependent with cooperative transitions between 49° C. and 67° C. (FIGS. 8B and 8C) suggesting that they each retained a stable and characteristic hairpin fold (Hodges and Schepartz, 2007, J Am Chem Soc. 129:11024-11025). Miniature protein 6.3, containing the greatest number of arginine substitutions (6), showed reduced ellipticity at 222 nm and 208 nm (FIG. 8A), along with a reduced Tm of 33° C. (FIGS. 8B and 8C); 6.3 was not studied further. For the remaining molecules, these CD data suggest that arginine substitution does not significantly alter miniature protein secondary structure, and that FIG. 1B accurately represents the arginine side chain arrangement in miniature proteins 2.1, 2.2, 3.2, 4.2, 4.3, 5.2, and 5.3.

Cell Uptake

Figure 2:
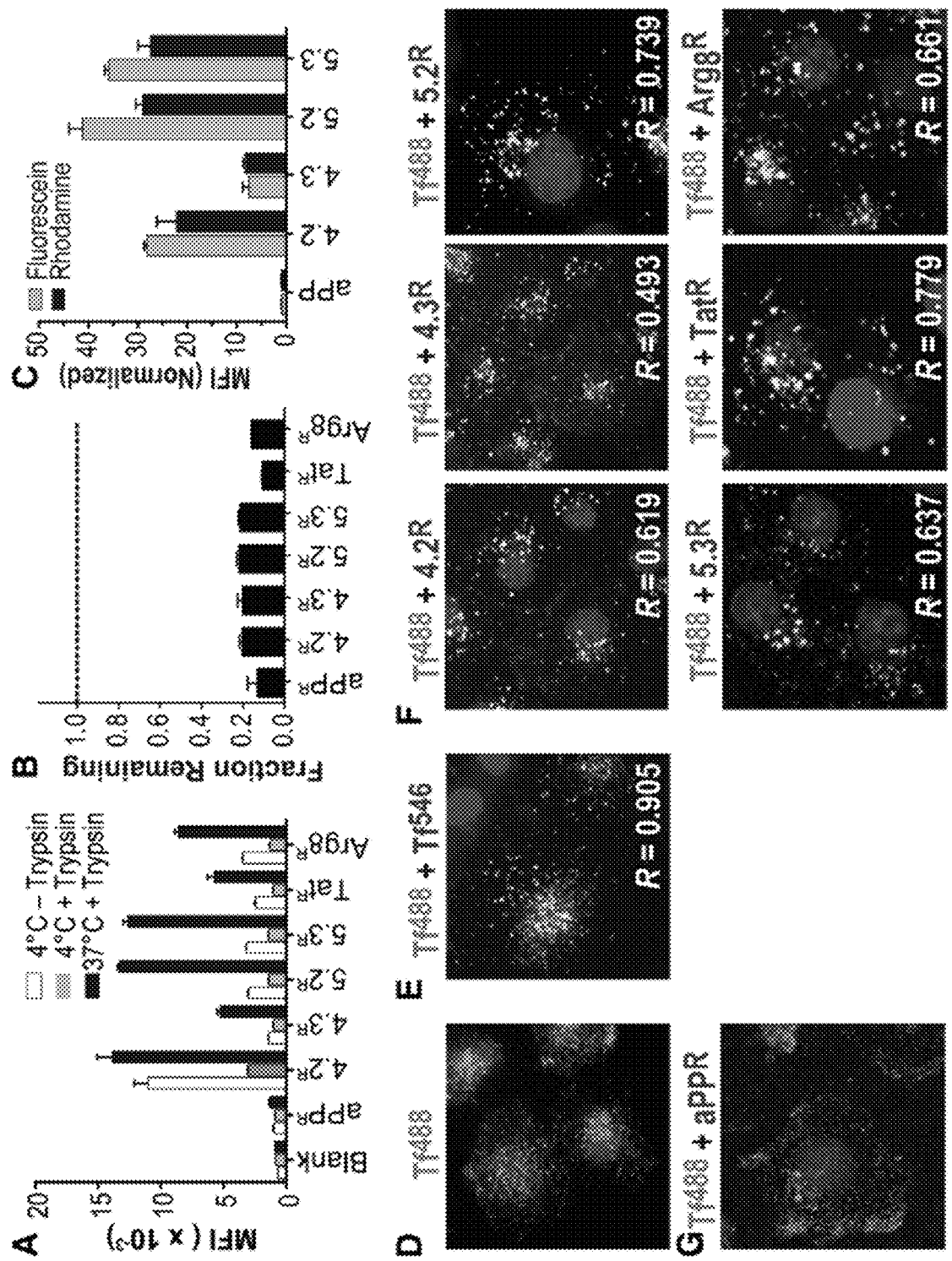
FIG. 2, comprising

Initially flow cytometry was used to assess the influence of arginine number and orientation on miniature protein uptake. In preliminary studies, molecules labeled with fluorescein on their C-termini (as denoted with superscript F) were evaluated. To ensure that the experiment measured miniature proteins that had entered cells, a trypsin wash was included just before analysis via flow cytometry. Treatment of HeLa cells with 5 μM aPPF, 2.1F, 2.2F, or 3.2F resulted in only small increases (<3 fold) in cell fluorescence, while treatment with 4.2F, 4.3F, 5.2F, or 5.3F resulted in increases in cell fluorescence between 7 and 40 fold (FIG. 1C). Therefore, miniature proteins showing significant uptake were studied, with results confirmed by synthesizing analogs labeled instead with tetraethyl rhodamine sulfate (denoted with superscript R), a dye with several desirable properties including resistance to photobleaching and an emission spectrum unaffected by pH changes and far from the auto-fluorescence spectrum of cells (Fernández-Suárez and Ting, 2008, Nat Rev Mol Cell Biol. 9:929-943). As found for miniature proteins labeled with fluorescein, rhodamine labeled miniature proteins containing four or five α-helical arginines were taken up efficiently, in some cases (5.2R and 5.3R) more efficiently than TatR (SEQ ID NO:67) or Arg8R (SEQ ID NO:68) (FIG. 2A).

Because previous studies have shown that cell-penetrating peptides, including Tat and Arg8, bind to cell surface proteoglycans (Payne et al., 2007, Traffic. 8:389-401), it was verified that trypsin treatment removed miniature proteins that were bound to the cell surface. Peptides and proteins that enter the cell are inaccessible to trypsin added to the culture media (Frankel and Pabo, 1988, Cell. 55:1189-1193). Therefore, membrane traffic was arrested by incubating cells at 4° C. (Hanover et al., 1984, Cell. 39:283-293; Vonderheit and Helenius, 2005, -Plos Biol. 3:e233) for 15 min prior to and during a 30 min treatment with 1 μM 4.2R, 4.3R, 5.2R, 5.3R, TatR (SEQ ID NO:67), Arg8R (SEQ ID NO:68) or aPPR. After incubation, cells were washed with PBS and incubated with 0.05% trypsin or PBS (as a control) before analysis by flow cytometry. These results were compared to those obtained when cells were incubated at 37° C. and treated with trypsin (FIG. 2A). Cationic miniature proteins 4.2R, 4.3R, 5.2R, and 5.3R bound to cells between 2.7-fold and 35-fold more than aPPR and in some cases (5.2R and 5.3R) to an extent comparable to TatR (SEQ ID NO:67) and Arg8R (SEQ ID NO:68). For cells incubated at 4° C., trypsin treatment decreased the fluorescent signal between 77-89% (FIG. 2B). These data confirm that at 4° C., incubation of cells with 1 μM cationic miniature protein leads to little if any cell uptake, and confirms that the vast majority of material bound to the cell surface is degraded and/or effectively removed by trypsin treatment. Comparison of the uptake of rhodamine and fluorescein labeled miniature proteins (FIG. 2C) shows that cell uptake depends on arginine density: miniature proteins containing four arginine residues clustered on two helical faces were taken up more efficiently than those containing four arginines on three helical faces (FIG. 2A,C and FIG. 1C). Molecules containing five α-helical arginines were taken up to a similar extent irrespective of density, revealing that among these molecules the impact of arginine arrangement was smaller. Consistent with previous work (Smith et al., 2008, J Am Chem Soc. 130:2948-2949), the cationic miniature proteins 5.2R and 5.3R are taken up with an efficiency ≥2 fold better than that of Tat (SEQ ID NO:67) or Arg8 (SEQ ID NO:68), despite the fact that they possess twice the mass and fewer (7 rather than 8) positive charges.

Cationic miniature proteins traffic first into endocytic vesicles

Figure 9:
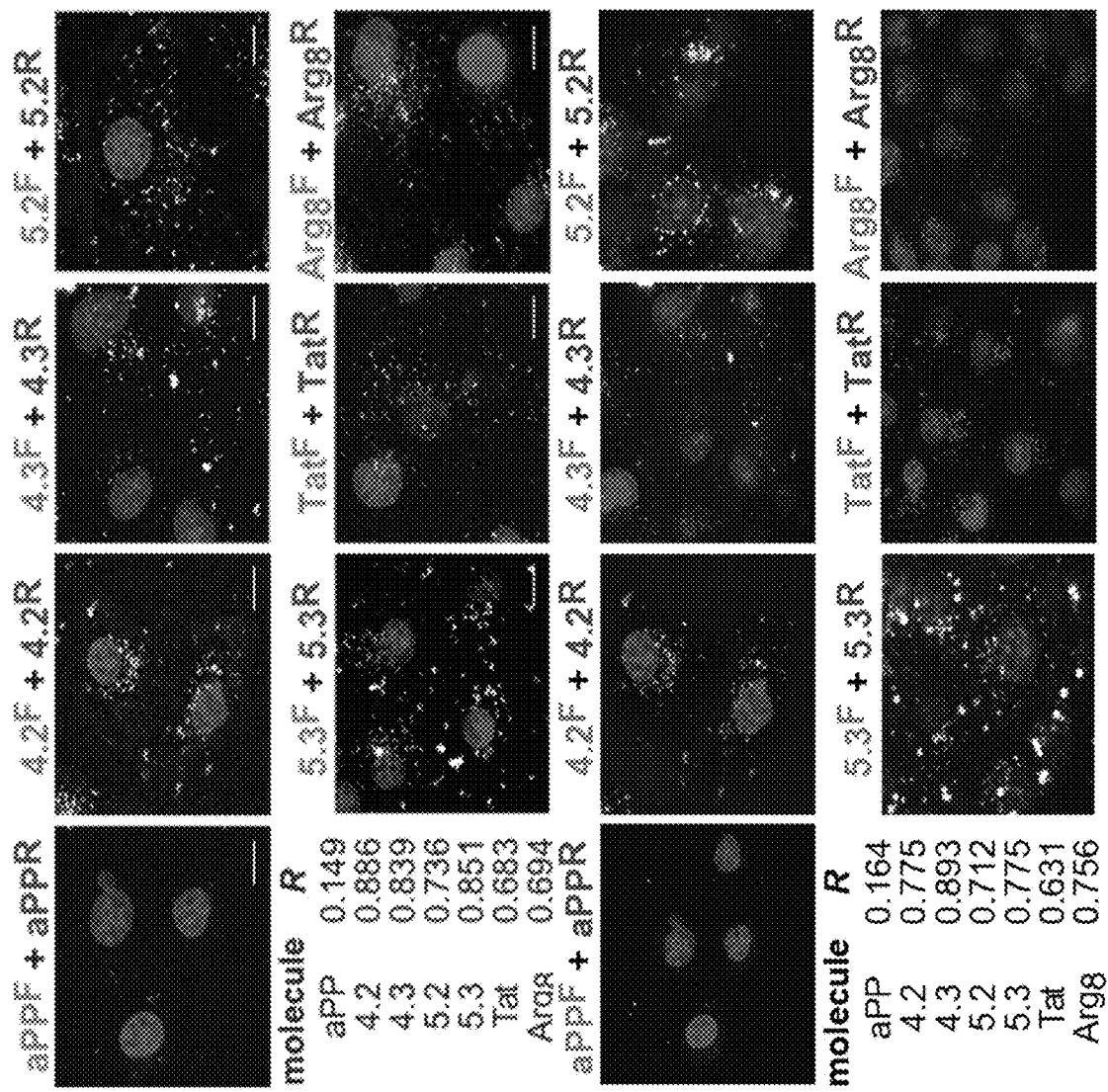
FIG. 9, depicts the results of experiments demonstrating the colocalization of rhodamine and fluorescein labeled cationic miniature proteins and peptides. HeLa cells were treated with a mixture of rhodamine—(indicated by the superscript R) and fluorescein—(indicated by the superscript F)—labeled miniature protein or peptide (1 μM each) for 30 min at 37° C., washed, and then imaged using confocal microscopy. HeLa cells treated with aPPR and aPPF show low fluorescence. The remaining molecules show high fluorescence, and molecules sharing the same sequence (but different labels) show high degrees of overlap, with R>0.68. The amino acid sequence of Arg8 is provided in SEQ ID NO:68.

To better understand the uptake pathway, HeLa cells were treated with rhodamine-labeled miniature proteins in the presence of transferrin labeled with AlexaFluor-488 (Tf488) and quantified fluorescence overlap using confocal microscopy. Transferrin is rapidly internalized from the plasma membrane into endocytic vesicles (Hanover et al., 1984, Cell. 39:283-293; Lakadamyali et al., 2006, Cell. 124:997-1009) and observing transferrin within rhodamine+ vesicles would suggest the vesicles were endocytic in nature, originating from the plasma membrane. HeLa cells were incubated for 30 min with Tf488 (25 nM) and 1 μM 4.2R, 4.3R, 5.2R, 5.3R, TatR (SEQ ID NO:67) or Arg8R (SEQ ID NO:68) before washing with media, staining with Hoescht (to visualize DNA), and imaging without fixation by confocal microscopy (FIG. 2D-F). Cells treated with Tf488 showed small, discrete areas of intense green fluorescent signal. Treatment with aPPR led to little or no red fluorescent signal (FIG. 2G) confirming earlier results that aPPR is not taken up efficiently. By contrast, HeLa cells treated with 1 μM 4.2R, 4.3R, 5.2R, 5.3R, TatR (SEQ ID NO:67) or Arg8R (SEQ ID NO:68) showed red fluorescent puncta throughout the cytosol in a distribution similar to that seen with Tf488 and at levels that qualitatively reproduce the trends detected by flow cytometry (FIG. 2F). The fluorescent signals from Tf488 and Tf546 were highly correlated (FIG. 2E), as were, with one exception, the fluorescent signals from Tf488 and rhodamine labeled miniature proteins/peptides (R488,rhodamine=0.619-0.779). Taken together, these data are consistent with the explanation that transferrin and cationic miniature proteins/peptides 4.2R, 5.2R, 5.3R, TatR (SEQ ID NO:67) and Arg8R (SEQ ID NO:68) are taken up into the same endocytic compartments. Miniature protein 4.3R is also taken up into a transferrin+ compartment, but the correlation (R488,rhodamine=0.493) is lower, possibly because the uptake is low (FIG. 2F). Additional experiments to assess whether peptide trafficking was affected by fluorophore identity confirmed that rhodamine and fluorescein labeled variants of cationic miniature proteins as well as Tat (SEQ ID NO:67) and Arg8 (SEQ ID NO:68) traffic together within cells, as indicated by highly correlated rhodamine and fluorescein intensities (R>0.6, p<1×10-10, FIG. 9).

Cationic Miniature Proteins Reach the Cytoplasm

Polypeptides and peptide mimetics showing cellular uptake by flow cytometry may remain trapped in endosomes and fail to reach the cytosol (Yu et al., 2011, ACS Nano 5:9246-9255; Maiolo et al., 2004, J Am Chem Soc. 126: 15376-15377). Previous assays for the cytosolic localization of peptide- or peptoid-dexamethasone (Dex) conjugates exploited the interaction of the Dex-labeled molecule with the ligand-binding domain of the cytosolic glucocorticoid receptor (GR), which led eventually to the transcription of luciferase and its detection in cell lysates 40-48 hours later (Yu et al., 2005, Nat Biotechnol. 23:746-751). Recognizing that treatment of cells with Dex leads to rapid (15 min) nuclear accumulation of a GR-green fluorescent protein fusion (GR-GFP) (Carey et al., 1996, J Cell Biol. 133:985-996), it was assessed whether microscopy could provide a rapid assay for cytosolic localization by revealing the nuclear accumulation of GR-GFP in the presence of peptide-Dex conjugates.

Figure 10:
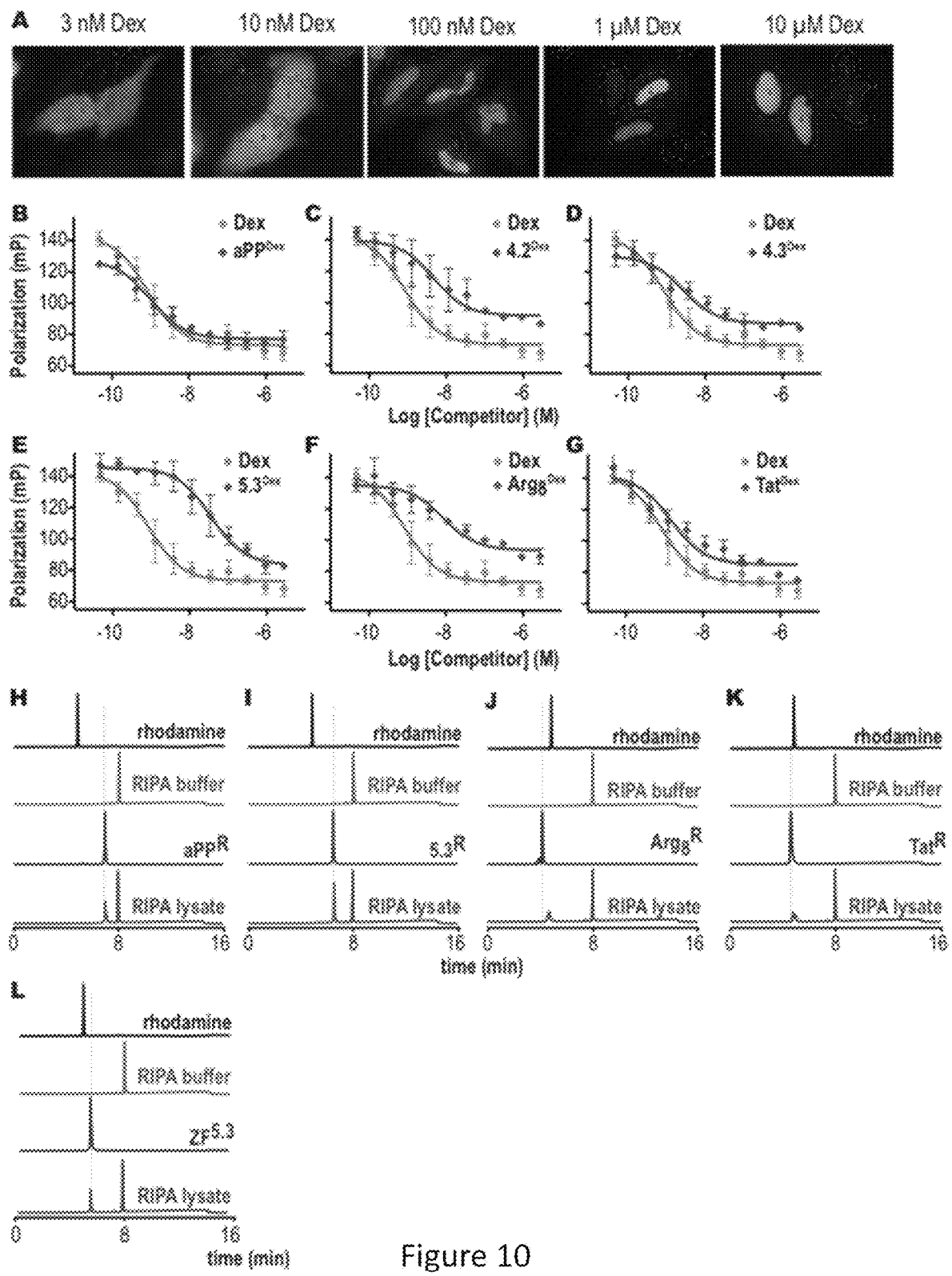
FIG. 10, comprising

HeLa cells transiently transfected with GR-GFP were incubated for 30 min with between 0 and 10 μM Dex (FIG. 3A and FIG. 10A). When Dex was absent from the incubation media, these cells exhibited GFP signal throughout the cytoplasm and the nucleus (FIG. 3A). Addition of between 3 nM and 10 μM Dex led to a dose-dependent decrease in the cytosolic GFP signal and a concomitant increase in the nuclear GFP signal (FIG. 10A). These changes were quantified using the automated image processing package CellProfiler (Carpenter et al., 2006, Genome Biol. 7:R100) to measure the ratio of the median GFP signal in the nucleus to the median signal within a 2 μm region surrounding region of cytosol (the 'translocation ratio', TR, FIG. 3B). TR values near 1 indicate equivalent intensity between the nucleus and the surrounding region. Treatment of HeLa cells with 1 μM Dex for 30 min resulted in an increase in the TR from 1.07±0.02 to 3.93±0.14 (p=1.92×10-22, vs. untreated cells, two-tailed t-test), roughly 90.5% of value achieved with a 10-fold higher concentration (FIG. 3C). Therefore, the lower concentration was chosen for subsequent studies. When cells transfected with GR-GFP were treated for 30 min with 1 μM aPPDex, virtually no change in GR-GFP localization or the TR was observed (1.41±0.09, vs. 1.25±0.04, p=0.1473, two-tailed t-test, FIG. 3A). These data are consistent with the observation that aPPR fails to enter cells, and with previous results (Yu et al., 2005, Nat Biotechnol. 23:746-751) that simply adding the Dex label does not confer upon an otherwise cell impermeable peptide the ability to reach the cytoplasm.

Next, the extent to which Dex-labeled miniature proteins, as well as Tat (SEQ ID NO:67) and Arg8 (SEQ ID NO:68), induce the nuclear translocation of GR-GFP (FIG. 3C and 3D) was evaluated. Treatment of HeLa cells expressing GR-GFP with 1 µM 5.3Dex (SEQ ID NO:33) for 30 min led to a large increase in TR (3.1±0.1) both compared to an untreated sample (−) (p=2.68×10-48, ANOVA with Bonferroni post-test) or one treated with aPPDex (p=1.96×10-16). Treatment of cells with 1 µM 4.2Dex (SEQ ID NO:30), 4.3Dex (SEQ ID NO:31), or 5.2Dex (SEQ ID NO:32) for 30 min led to a small or absent increase in nuclear GFP signal, and TRs (1.18±0.04, 1.92±0.10, 1.77±0.11 respectively) that were not significantly different from cells treated with aPPDex. The TR measured after treatment of cells with Arg8Dex (SEQ ID NO:37) (2.19±0.13) or TatDex (SEQ ID NO:36) (2.85±0.10) were increased over control samples treated with aPPDex (Arg8Dex (SEQ ID NO:37), p=0.0053; TatDex (SEQ ID NO:36), p=2.54×10-9), and comparable to cells treated with 5.3Dex (SEQ ID NO:33). Control experiments verified that the affinities of Dex labeled cationic miniature proteins and peptides for the human glucocorticoid receptor in vitro were similar to each other (between 1-36 nM), though slightly poorer than Dex itself (0.1 nM, see FIGS. 10B-10G).

Next, it was assessed whether degradation of miniature proteins could lead to GR-GFP activation through release of the Dex moiety. While aPPR, 5.2R, and 5.3R are cleaved by cathepsin D (and to a smaller extent cathepsin L) in vitro (FIGS. 13D-13F), HPLC analysis of whole cell lysates revealed minimal to no cleavage of the aPPR and 5.3R backbones in cells under the conditions of the translocation assay (FIGS. 10H and 10I). The stability of aPPR and 5.3R under these conditions minimizes the possibility that the increased TR observed in the presence of 5.3Dex (SEQ ID NO:33) results from increased degradation or protease susceptibility of this protein compared to aPPDex or 5.2Dex (SEQ ID NO:32). To further validate the results of the translocation assay, cytoplasmic extracts were generated from HeLa cells treated with rhodamine labeled miniature proteins using streptolysin O (SLO) (Androlewicz et al., 1993, Proc Natl Acad Sci USA 90:9130-9134). HPLC analysis of the SLO-extracts from HeLa cells treated with aPPR showed little to no fluorescent material, while analysis of cytoplasmic extracts from HeLa cells treated with 5.3R confirmed the presence of intact 5.3R (FIGS. 13B-13H). Analysis of cytoplasmic extracts from HeLa cells treated with TatR (SEQ ID NO:67) or Arg8R (SEQ ID NO:68) also showed fluorescent material, but with retention times distinct from the starting material (FIGS. 13G and 13H), consistent with previous observations (Palm et al., 2007, -Biochim Biophys Acta 1768:1769-1776) that unstructured cell penetrating peptides can be rapidly degraded.

Cytoplasmic Access Requires Active Endocytosis

Figure 4:
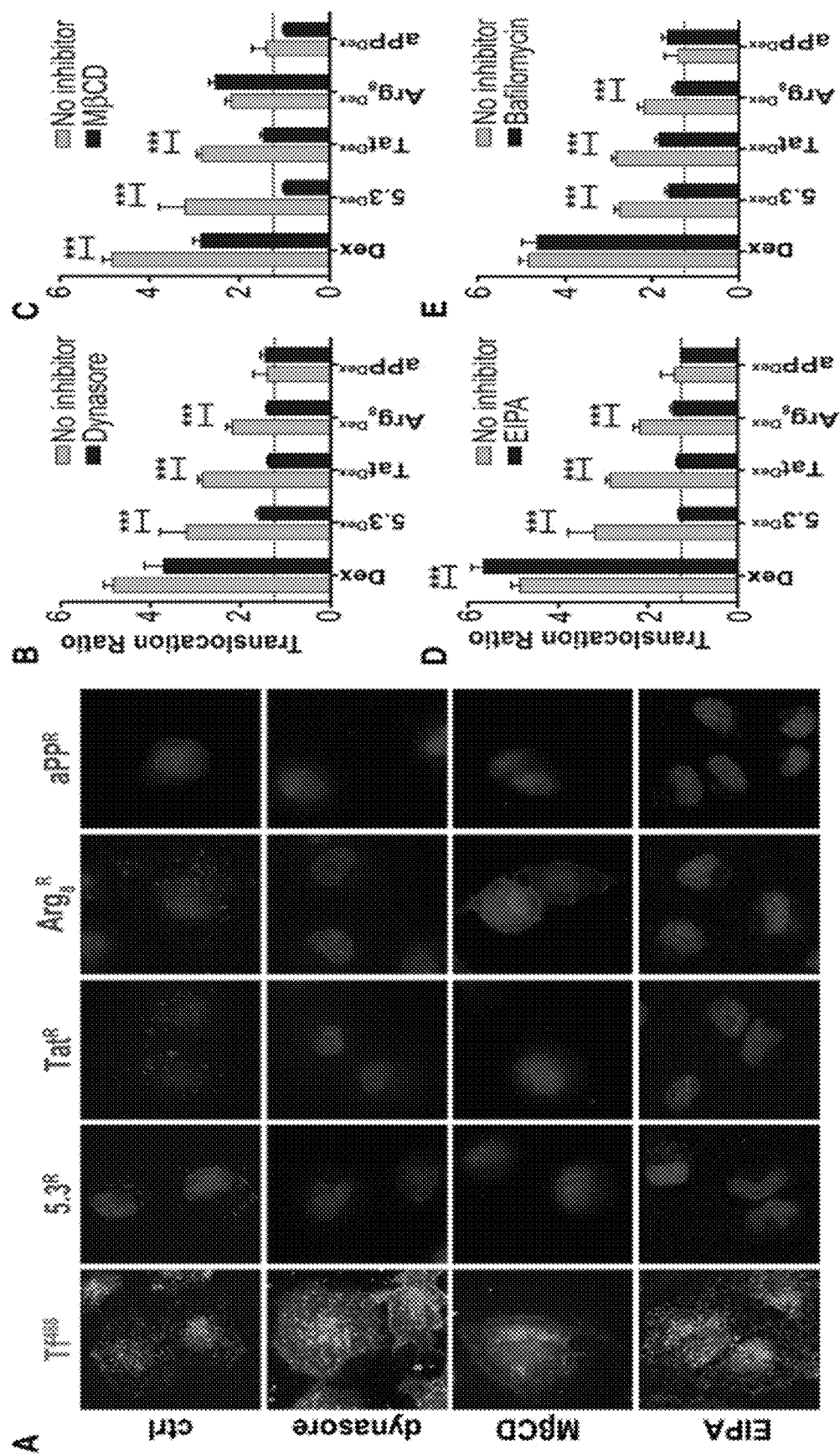
FIG. 4, comprising
Figure 11:
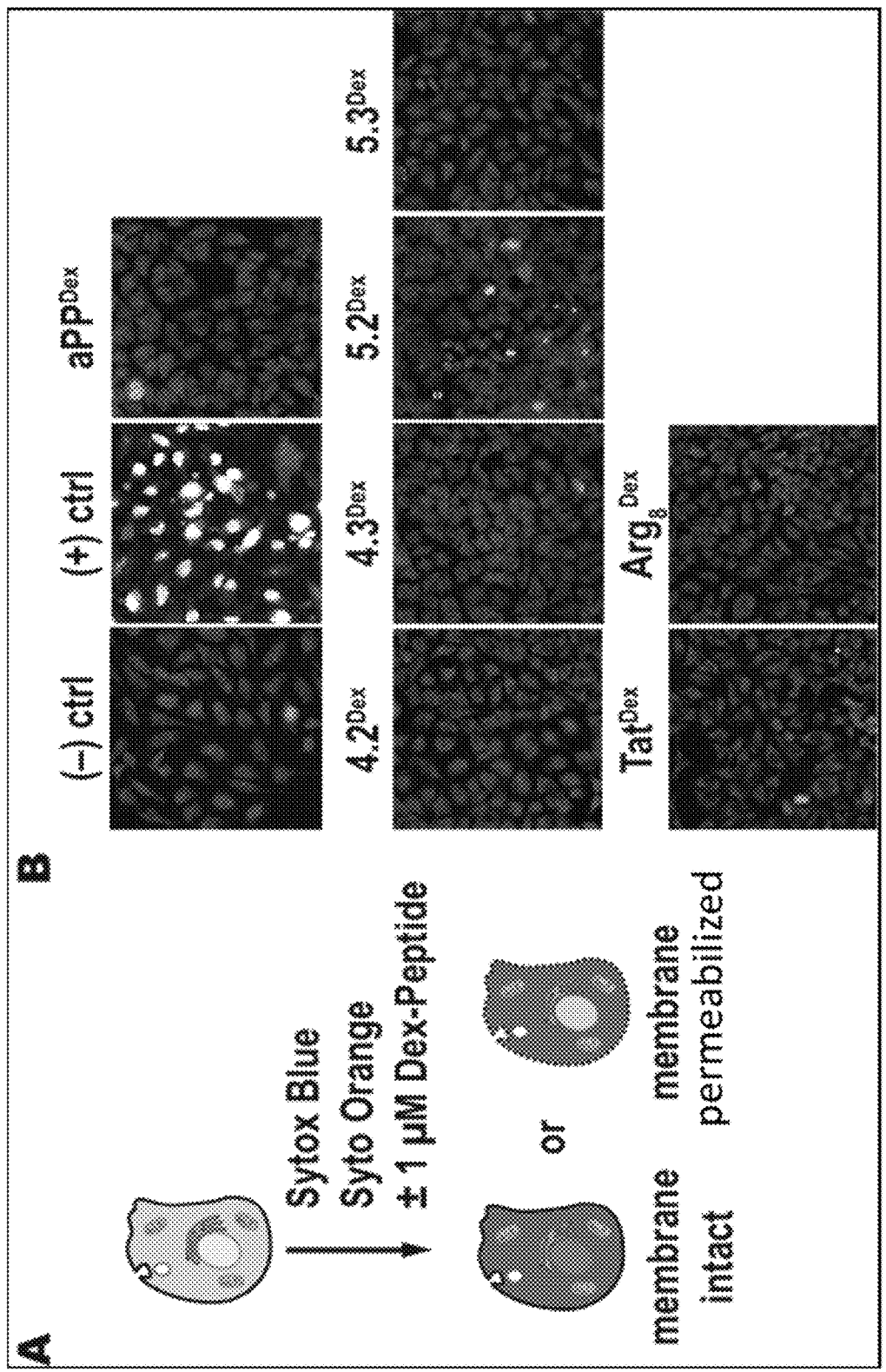
FIG. 11, comprising

Two limiting models have been invoked to explain the trafficking of cationic peptides and proteins across the plasma membrane and into the cytoplasm. One model invokes ion-pair guided passive membrane diffusion (Rothbard et al., 2005, Adv Drug Deliv Rev. 57:495-504); the other invokes endocytosis followed by endosomal release. Experiments were performed to distinguish between these models. First, it was assessed whether inhibitors of endocytosis block the uptake of cationic miniature proteins, their cytosolic localization, or both (FIG. 4). Second, it was confirmed that cell membrane integrity is not disrupted by the presence of 1 µM cationic miniature protein (FIG. 11).

To determine whether active endocytosis is required for 5.3Dex to reach the cytoplasm, HeLa cells expressing GR-GFP were treated with inhibitors of endocytosis before and during exposure to 1 µM 5.3Dex. Clathrin-mediated endocytosis (CME), pinocytosis, and caveolin-mediated endocytosis are dependent on dynamin (Doherty and McMahon, 2009, Annu. Rev. Biochem. 78:857-902), the activity of which is inhibited by the small molecule dynasore (Macia et al., 2006, Developmental Cell. 10:839-850). Depleting cellular cholesterol by treatment with methyl-β-cyclodextrin (MβCD) also inhibits these three processes (Rodal et al., 1999, Mol Biol Cell 10:961-974). Actin remodeling, a process inhibited by addition of N-ethyl-isopropyl amiloride (EIPA) (Koivusalo et al., 2010, J Cell Biol. 188:547-563) facilitates clathrin-coated pit formation (Doherty and McMahon, 2009, Annu. Rev. Biochem. 78:857-902) and is required for some dynamin and cholesterol-independent endocytic pathways. Notably, addition of EIPA does not block the uptake of some CME ligands such as transferrin (Koivusalo et al., 2010, J Cell Biol. 188:547-563).

To test the involvement of these pathways in the uptake of cationic miniature proteins and peptides, HeLa cells were pretreated for 30 min with 80 µM dynasore, 5 mM MβCD or 50 µM EIPA before adding 1 µM aPPR, 5.3R, TatR (SEQ ID NO:67), or Arg8R (SEQ ID NO:68) for 30 min at 37° C. in the presence of inhibitor. The cells were subsequently washed and visualized by confocal microscopy (FIG. 4A). The presence of dynasore completely blocked the uptake of 5.3R, as well as TatR (SEQ ID NO:67) and Arg8R (SEQ ID NO:68), suggesting that all three molecules are taken up in a dynamin-dependent fashion. The presence of EIPA also dramatically reduced the uptake of all three molecules, suggesting a role for actin metabolism in the internalization process. MβCD completely blocked the uptake of 5.3R, and TatR (SEQ ID NO:67), but not Arg8R (SEQ ID NO:68). Surprisingly cellular uptake of Arg8R (SEQ ID NO:68) was increased in the presence of MβCD, leading to diffuse fluorescence throughout the cytosol, a pattern not observed in the absence of the inhibitor.

Next, the effect of blocking endocytosis on the ability of 5.3Dex (SEQ ID NO:33), TatDex (SEQ ID NO:36), and Arg8Dex (SEQ ID NO:37) to reach the cytoplasm was measured. It was considered that exchanging the rhodamine label for Dex could alter the physical properties of the molecule, as well as the manner in which it trafficked in cells. HeLa cells transfected with GR-GFP were pre-treated for 30 min with the same inhibitors prior to the addition of either 1 µM Dex (positive control), aPPDex (negative control), 5.3Dex (SEQ ID NO:33), TatDex (SEQ ID NO:36), or Arg8Dex (SEQ ID NO:37) for 30 min at 37° C. (FIG. 4B-D). The cells were then washed and imaged to measure the TR. None of the endocytosis inhibitors altered the TR calculated for cells treated with aPPDex. However, all three inhibitors reduced, to background levels, the TR calculated after treatment with 5.3Dex (SEQ ID NO:33), TatDex (SEQ ID NO:36), and both dynasore and EIPA reduced the TR observed after treatment with Arg8Dex (SEQ ID NO:37). Consistent with microscopy results discussed above (FIG. 4), the cytoplasmic access of Arg8Dex (SEQ ID NO:37) was not decreased in the presence of MβCD. Neither EIPA nor dynasore blocked the increase in the TR calculated after treatment with Dex, but MβCD reduced this increase by 53%, presumably the result of direct complexation of free Dex by MβCD (Moya-Ortega et al., 2010, Carbohydrate Polymers. 80:900-907). The results with Arg8R (SEQ ID NO:68) notwithstanding, these data support the contribution of endocytic pathways to the uptake of cationic miniature proteins and peptides, and not a model based on passive diffusion.

The acidification of endosomes begins almost immediately upon scission from the plasma membrane, as their lumen no longer communicates with the surrounding media. Bafilomycin is a potent inhibitor of the vesicular ATPase (Yoshimori et al., 1991, J Biochem. 266:17707-17712), and its addition to culture media prevents endosomal acidification (Yoshimori et al., 1991, J Biochem. 266:17707-17712; Fischer et al., 2004, J Biol Chem. 279:12625-12635). To ask whether low vesicular pH was required for cytoplasmic escape, HeLa cells expressing GR-GFP were pretreated with 200 nM bafilomycin for 1 h before exposure to 1 μM Dex, 5.3Dex (SEQ ID NO:33), TatDex (SEQ ID NO:36), Arg8Dex (SEQ ID NO:37) or aPPDex (FIG. 4E). Treatment with bafilomycin did not alter the effect of Dex or aPPDex on the TR, but completely blocked the increase in TR seen after cells were exposed to 5.3Dex (SEQ ID NO:33) (p=1.4× 10-11), TatDex (SEQ ID NO:36) (p=5.3×10-11) or Arg8Dex (SEQ ID NO:37) (p=8.2×10-6). Thus, while 5.3Dex (SEQ ID NO:33), TatDex (SEQ ID NO:36), and Arg8Dex (SEQ ID NO:37) reach the cytoplasm, they fail to do so in the absence of endosome acidification. This finding is consistent with the model that these molecules do not penetrate the plasma membrane directly, but rather escape to the cytoplasm from acidified endocytic vesicles.

The acidification of endosomes begins almost immediately upon scission from the plasma membrane, as their lumen no longer communicates with the surrounding media. Bafilomycin is a potent inhibitor of the vesicular ATPase (Yoshimori et al., 1991, J Biochem. 266:17707-17712), and its addition to culture media prevents endosomal acidification (Yoshimori et al., 1991, J Biochem. 266:17707-17712; Fischer et al., 2004, J Biol Chem. 279:12625-12635). To ask whether low vesicular pH was required for cytoplasmic escape, HeLa cells expressing GR-GFP were pretreated with 200 nM bafilomycin for 1 h before exposure to 1 μM Dex, 5.3Dex (SEQ ID NO:33), TatDex (SEQ ID NO:36), Arg8Dex (SEQ ID NO:37) or aPPDex (FIG. 4E). Treatment with bafilomycin did not alter the effect of Dex or aPPDex on the TR, but completely blocked the increase in TR seen after cells were exposed to 5.3Dex (SEQ ID NO:33) (p=1.4× 10-11), TatDex (SEQ ID NO:36) (p=5.3×10-11) or Arg8Dex (SEQ ID NO:37) (p=8.2×10-6). Thus, while 5.3Dex (SEQ ID NO:33), TatDex (SEQ ID NO:36), and Arg8Dex (SEQ ID NO:37) reach the cytoplasm, they fail to do so in the absence of endosome acidification. This finding is consistent with the model that these molecules do not penetrate the plasma membrane directly, but rather escape to the cytoplasm from acidified endocytic vesicles.

Escape to the Cytoplasm from Early Endosomes

Phospholipids present in newly formed clathrin-coated vesicles and macropinosomes undergo rapid modification resulting in the recruitment of Rab5 (Lakadamyali et al., 2006, Cell. 124:997-1009; Zoncu et al., 2009, Cell. 136: 1110-1121). Rab5 is a master regulator of endosome biogenesis (Zeigerer et al., 2012, Nature 485:465-470) and recruits additional cellular factors required for vesicle maintenance, fusion and maturation, including the phosphotidyl inositol (PI) 3-OH kinase (PI3K), Vps34 (Christoforidis et al., 1999b, Nat Cell Biol. 1:249-252). The resulting early endocytic compartment mixes via homotypic fusion with other Rab5+ vesicles (Stenmark et al., 1994, EMBO J 13:1287-1296), and delivers cargo to other cellular locales through the budding off of transport vesicles (Puthenveedu et al., 2010, Cell. 143:761-773) or Rab conversion (Rink et al,. 2005, Cell. 122:735-749). While some cargo (such as transferrin) is recycled to the cell surface, other cargo, such as low density lipoprotein, epidermal growth factor (Cantalupo et al., 2001, EMBO J. 20:683-693) and several types of viruses (Vonderheit and Helenius, 2005, Plos Biol. 3:e233) are delivered to late endosomes, marked by Rab7, for degradation in lysosomes (Huotari and Helenius, 2011, EMBO J. 30:3481-3500). To characterize the intracellular route taken by 5.3R, TatR (SEQ ID NO:67) and Arg8R (SEQ ID NO:68), overlap of these molecules with markers of endocytic uptake and GFP tagged Rab proteins were searched for. Small molecule inhibitors and dominant negative Rab variants were also used to test the cellular activities required for 5.3Dex (SEQ ID NO:33), TatDex (SEQ ID NO:36) and Arg8Dex (SEQ ID NO:37) to enter the cytoplasm.

Figure 5:
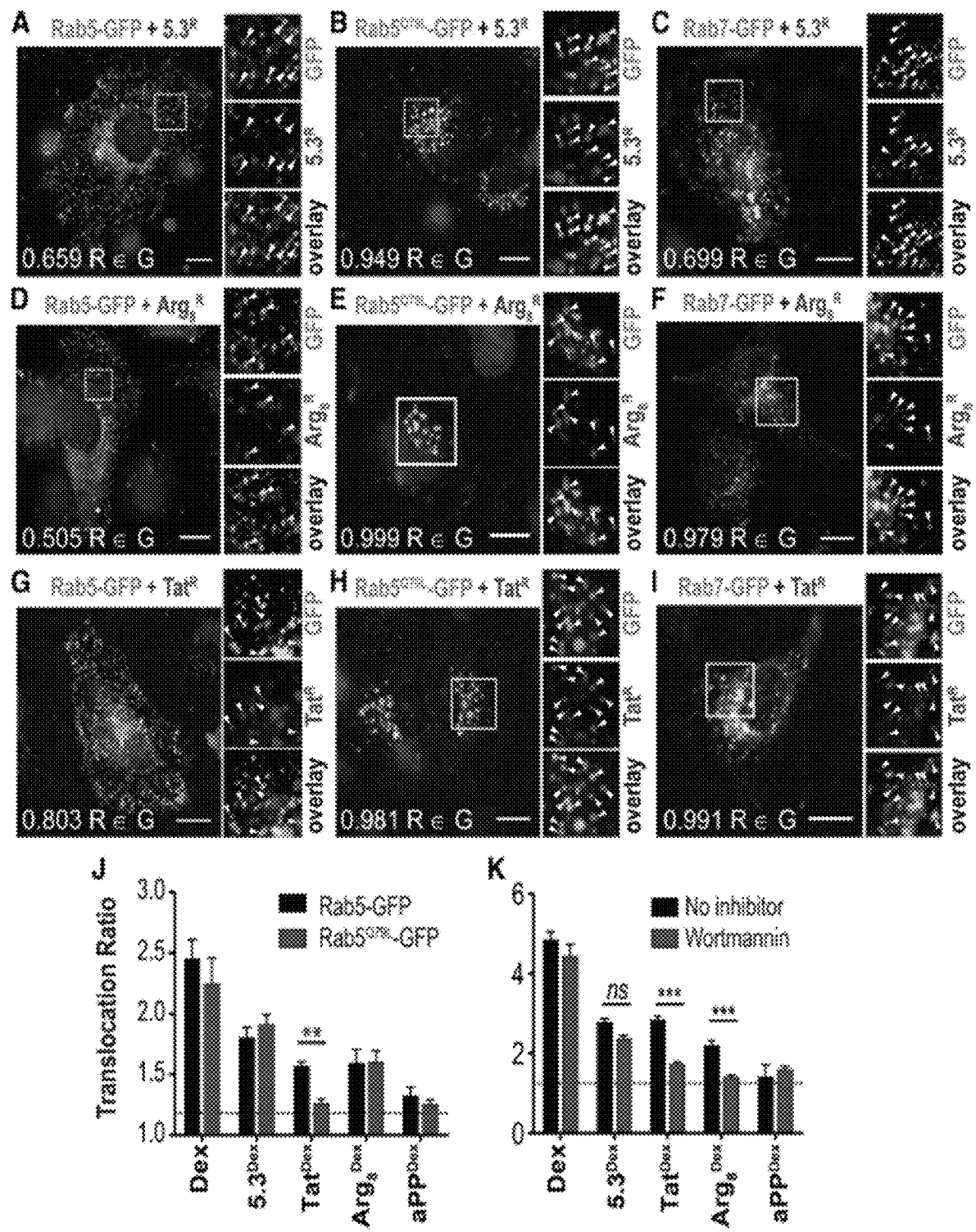
FIG. 5, comprising
Figure 12:
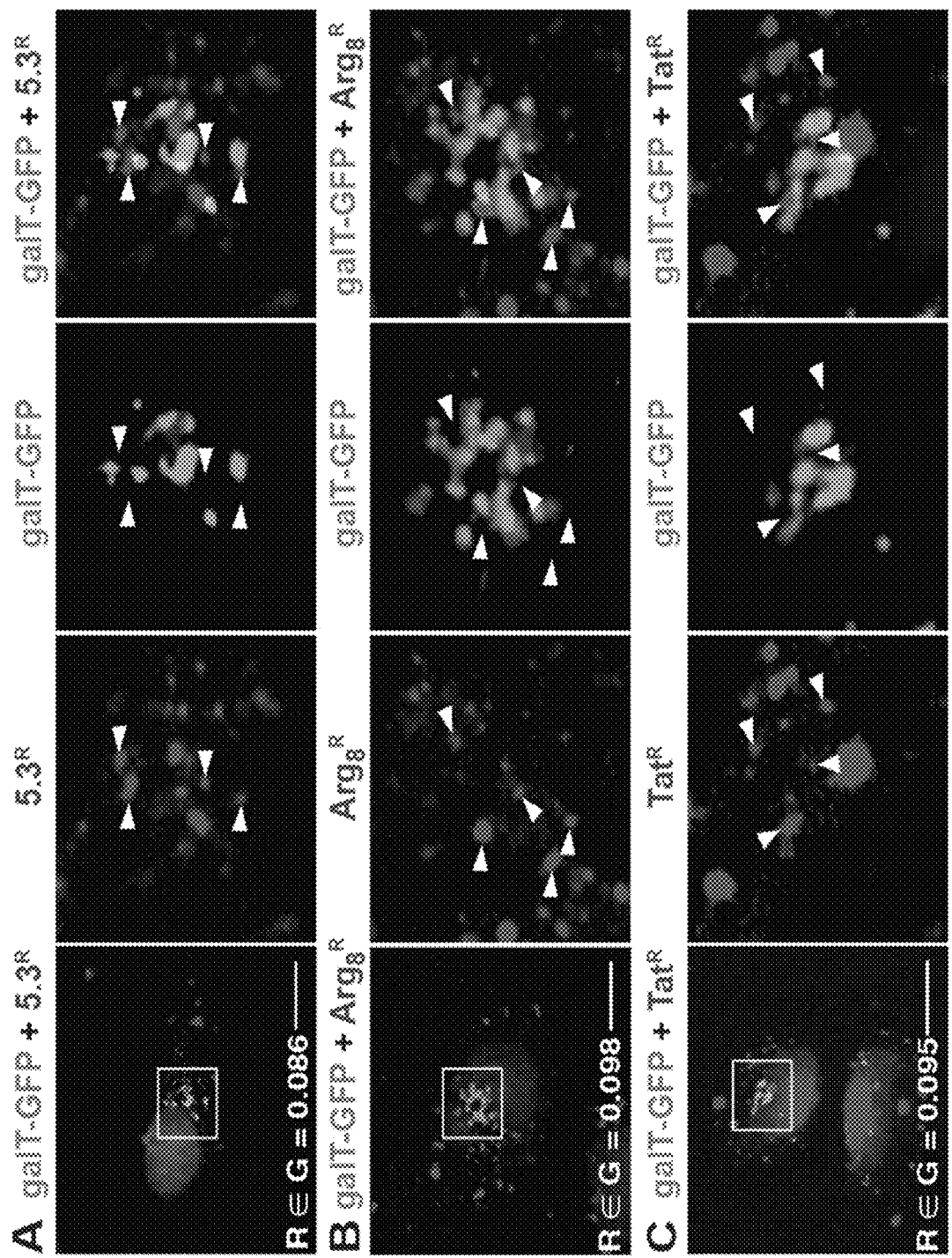
FIG. 12, comprising

Based on the observation that 5.3R colocalizes with transferrin (FIG. 3), a substrate known to internalize into Rab5+ vesicles (Lakadamyali et al., 2006, Cell. 124:997-1009), it was assessed whether 5.3R was also present in Rab5+ vesicles. HeLa cells were transfected with GFP-Rab5 and treated for 30 min with 1 μM 5.3R. When these cells were examined by confocal microscopy, 66% of the rhodamine signal overlapped with the signal from GFP-Rab5, confirming that 5.3R is present in Rab5+ vesicles (FIG. 5A). Because Rab5 vesicles rapidly deliver their cargo to downstream vesicles (Rink et al., 2005), it was also evaluated whether colocalization of 5.3R with Rab7-GFP (FIG. 5C). HeLa cells transfected with Rab7-GFP and treated with 5.3R as above, showed a large fraction (87%) of the rhodamine signal located in the Rab7-GFP compartment, confirming that 5.3R enters both early (Rab5+) and late (Rab7+) endosomes. No overlap between 5.3R, TatR (SEQ ID NO:67), or Arg8R (SEQ ID NO:68) and galT-GFP was found (Cole et al., 1996, Science. 273:797-801), a marker of the golgi (FIG. 12). To test whether trafficking of 5.3R could be arrested at the Rab5 stage, a GTPase-inactive Rab5 mutant, Rab5Q79L (Stenmark et al., 1994, EMBO J 13:1287-1296), which blocks delivery of cargo to late endosomes and arrests vesicle maturation (Rink et al,. 2005, Cell. 122:735-749), was overexpressed. Observation of HeLa cells transfected with Rab5Q79L-GFP and treated with 5.3R showed that nearly all (99%) of the miniature protein localized to enlarged GFP+ endosomes (FIG. 5D), consistent with the explanation that arresting early endosome maturation arrests trafficking of 5.3R at the Rab5+ stage. Similar results were seen with Arg8R (SEQ ID NO:68) and TatR (SEQ ID NO:67) (FIG. 5D-I). These data suggest that 5.3R, TatR (SEQ ID NO:67) and Arg8R (SEQ ID NO:68) follow a shared path through Rab5+ and then Rab7+ vesicles and provide a starting point to ask which, if any, of these trafficking events are required to reach the cytoplasm.

To identify the point or points along the endocytic pathway at which these three molecules escape to the cytosol, vesicle maturation was blocked through overexpression of Rab5Q79L-GFP and assayed for cytosolic localization using dual color microscopy and an orthogonally labeled GR-mCherry. The TR of untreated HeLa cells expressing Rab5Q79L-GFP or Rab5-GFP and GR-mCherry was near unity (TR=1.32±0.07), as expected, and remained unchanged after treatment for 30 min with 1 μM aPPDex (TR=1.25±0.04). As expected, the TR values of Rab5Q79L-GFP and Rab5-GFP expressing cells increased after treatment for 30 min with 1 μM of Dex (TR=2.24±0.15 and 2.45±0.21 for Rab5-GFP and Rab5Q79L-GFP expressing cells, respectively; FIG. 5J). Treatment with 1 µM 5.3Dex (SEQ ID NO:33) resulted in TR values that were similar regardless of whether cells were transfected with wild-type Rab5-GFP or Rab5Q79L-GFP (1.80±0.08 vs. 1.90±0.07, respectively); similar findings were observed when cells were treated with Arg8Dex (SEQ ID NO:37) (1.59±0.11 vs. 1.60±0.09). By contrast, treatment with TatDex (SEQ ID NO:36) resulted in TR values that differed depending on whether cells were transfected with wild type Rab5-GFP or Rab5Q79L-GFP (1.57±0.04 vs. 1.26±0.03, p=0.0057, respectively). Thus, arresting vesicle maturation with the GTPase-inactive Rab5 mutant Rab5Q79L blocked the ability of TatDex (SEQ ID NO:36) to reach the cytoplasm, but had no effect on 5.3Dex (SEQ ID NO:33) or Arg8Dex (SEQ ID NO:37). These findings are consistent with the explanation that 5.3 and Arg8 (SEQ ID NO:68) escape to the cytoplasm from Rab5+ vesicles, whereas Tat (SEQ ID NO:67) can only escape later along the endocytic pathway.

To arrest endocytic traffic at an earlier stage, cells were treated with 200 nM wortmannin, a pharmacologic inhibitor of PI3K that blocks the maturation of Rab5+ vesicles (Christoforidis et al., 1999a, Nature. 397:621-625) by decreasing the recruitment of Rab5 effectors that bind simultaneously to Rab5 and PI-3-phosphate containing membranes (Zoncu et al., 2009, Cell. 136:1110-1121). Wortmannin treatment blocked the increase in TR seen after treatment with TatDex (SEQ ID NO:36) and Arg8Dex (SEQ ID NO:37) by 72% and 77%, respectively (FIG. 5K). In contrast, the TR seen after treatment with 5.3Dex (SEQ ID NO:33) in the presence or absence of wortmannin was similar (2.36±0.08 vs. 2.76±0.10), confirming that 5.3Dex (SEQ ID NO:33) escapes at or before the earliest Rab5+ state. Taken together, these data are consistent with the explanation that arresting vesicle maturation inhibits the cytosolic access of both TatDex (SEQ ID NO:36) and Arg8Dex (SEQ ID NO:37), but that 5.3Dex (SEQ ID NO:33) is capable of leaving these earliest vesicles and reaching the cytoplasm.

Figure 3:
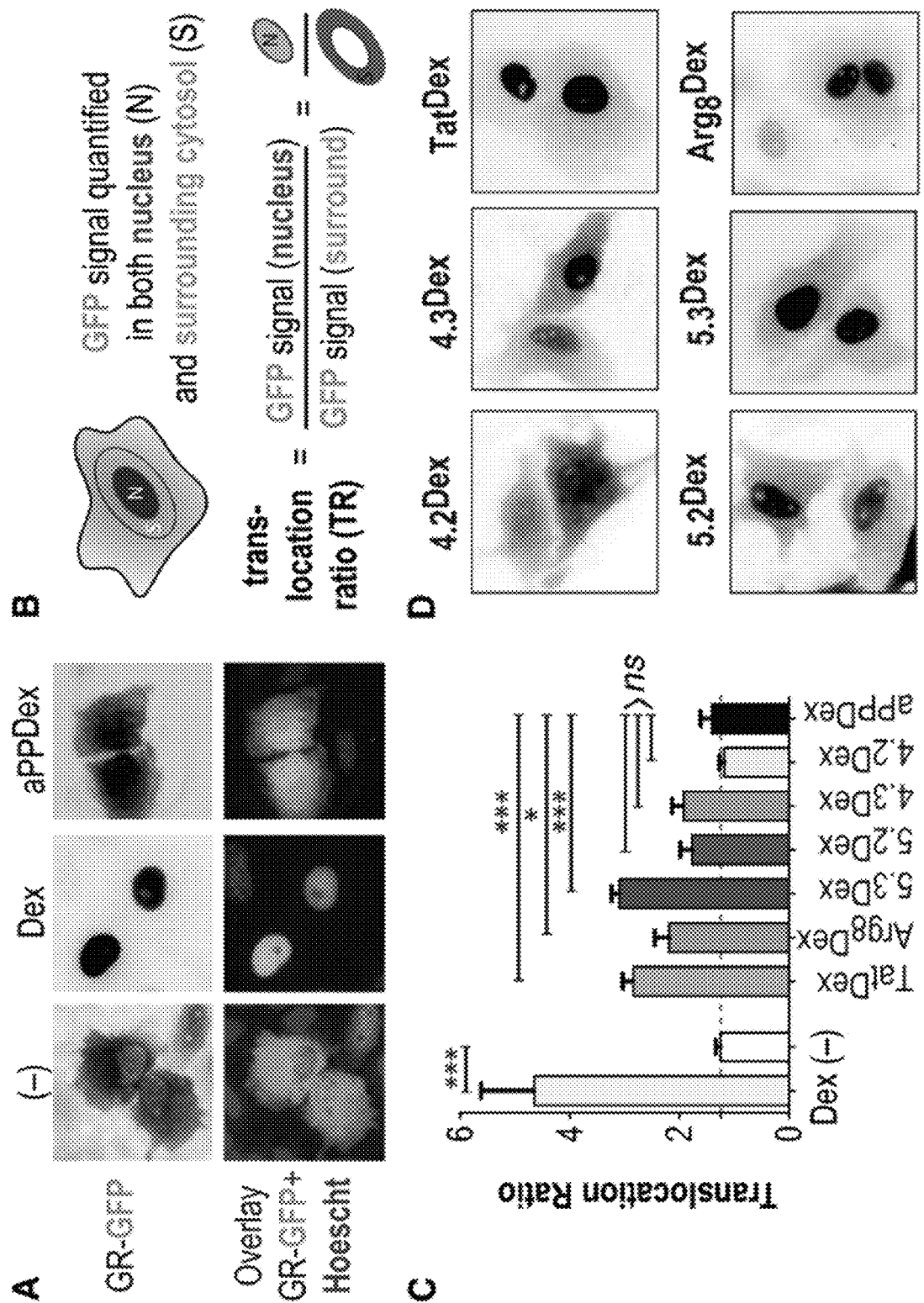
FIG. 3, comprising
Figure 6:
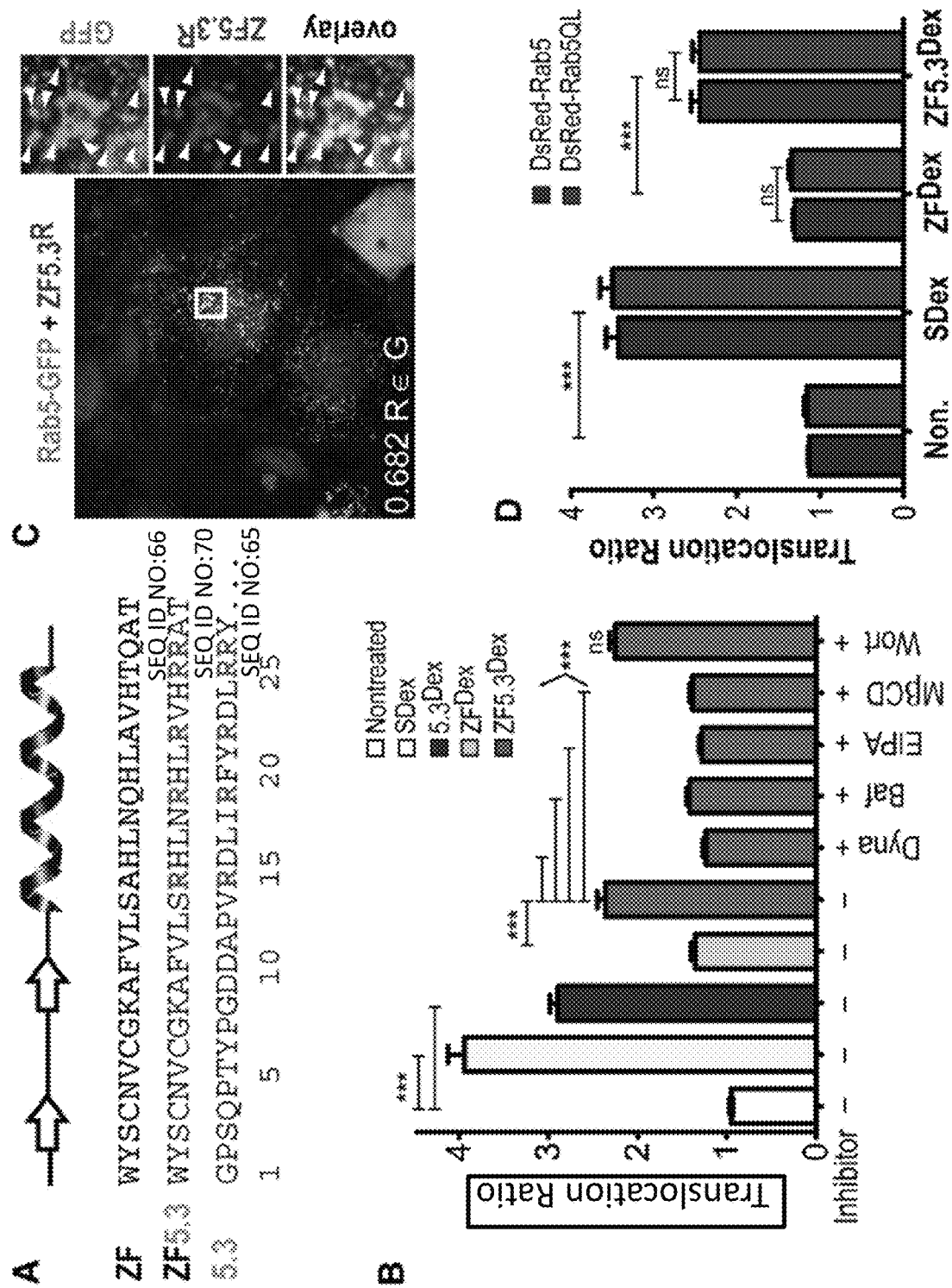
FIG. 6, comprising

Increased Cytosolic Localization of Zinc Finger Proteins Modified with 5.3 Arg Motif The results described above are consistent with the explanation that the arginine motif present in the aPP variant 5.3 facilitates the release of this molecule from Rab5+ endosomes into the cytosol. Notably, the regioisomer 5.2, although also decorated with five arginine side chains on the external α-helix face, is not released (FIG. 3). To determine whether the arginine motif present on the 5.3 α-helix is transportable, that is, whether it can promote the cytosolic localization of other α-helix containing proteins, zinc finger proteins were utilized, as their therapeutic potential is well known (Sera, 2009, Adv Drug Deliv Rev. 61:513-526; Urnov et al., 2010, Nat Rev Genet. 11:636-46). Beginning with the sequence of CP1, a single zinc finger possessing high zinc ion affinity (Krizek et al., 1991, J Am Chem Soc. 113:4518-4523), a dexamethasone-labeled variant (ZF5.3Dex) was prepared whose α-helix was substituted with the arginine motif in 5.3 (FIG. 6A), a change that neither prevented zinc binding nor significantly changed the secondary structure as measured by CD (FIG. 13A). The extent to which ZF5.3Dex induced the nuclear translocation of GR-GFP was evaluated, when compared with a variant lacking the arginine motif (ZFDex) (FIG. 6B). Treatment of HeLa cells expressing GR-GFP with 1 µM ZF5.3Dex for 30 min led to a large increase in TR (2.4±0.09) compared to both an untreated sample (0.9±0.05) and one treated with ZFDex (1.4±0.05) (p<0.0001, ANOVA with Bonferroni post-test). Control experiments confirmed that ZF5.3R can be recovered from cytosolic extracts of HeLa cells treated with ZF5.3R (FIG. 10L), and that the peptide backbone of ZF5.3 is not degraded under the conditions in this assay (FIG. 13I). As was observed with 5.3, inhibition of early endocytic events with dynasore, bafilomycin, EIPA or methyl-β-cyclodextrin reduced to background levels the increase in translocation ratios observed in the presence of ZF5.3Dex (FIG. 6B). Furthermore, as observed with 5.3, when cells expressing GFP-Rab5 were treated with ZF5.3R and examined by confocal microscopy, 68% of the rhodamine channel overlapped with the signal from GFP-Rab5, confirming that ZF5.3R is present in Rab5+ vesicles (FIG. 6C). Finally, as observed with 5.3, the TR of cells treated with ZF5.3R was unaffected when endocytic traffic was arrested by treatment with wortmannin or overexpression of dominant negative Rab5Q79L-GFP (FIG. 6D). Together, these data are consistent with the explanation that the arginine motif in ZF5.3, like the arginine motif in 5.3, functions to promote endocytic uptake and release from early Rab5+ endosomes, and emphasizes the potential of helical-arginine display for modulating the escape of cationic miniature proteins and peptidomimetics from early endosomes into the cytoplasm. The results described herein provide a structural and mechanistic framework for efficiently increasing the cell permeabilities of therapeutic peptides and proteins.

Mass Spectral Characterization of Miniature Proteins and Peptides Studied Herein

TABLE 1

Mass spectral characterization of miniature proteins and peptides.

| Name | SEQ ID NO: | Sequence | Formula | Calc (+m/z) | Meas |
|---|---|---|---|---|---|
| aPP | 3 | GPSQPTYPGDDAPVEDLIRFYNDLQQYLNVVTRHRYC$^{acetyl}$-$_{NH2}$ | $C_{195}H_{289}N_{54}O_{61}S_1$ | 4399 | 4400 |
| 2.1 | 4 | GPSQPTYPGDDAPVEDLIRFYNDLQRYLNVVTRHRYC$^{acetyl}$-$_{NH2}$ | $C_{196}H_{293}N_{56}O_{60}S_1$ | 4427 | 4430 |
| 2.2 | 5 | GPSQPTYPGDDAPVEDLIRFYRDLQQYLNVVTRHRYC$^{acetyl}$-$_{NH2}$ | $C_{197}H_{295}N_{57}O_{60}S_1$ | 4441 | 4445 |
| 3.2 | 6 | GPSQPTYPGDDAPVEDLIRFYRDLQRYLNVVTRHRYC$^{acetyl}$-$_{NH2}$ | $C_{198}H_{299}N_{58}O_{59}S_1$ | 4469 | 4475 |
| 4.2 | 7 | GPSQPTYPGDDAPVRDLIRFYRDLQRYLNVVTRHRYC$^{acetyl}$-$_{NH2}$ | $C_{199}H_{304}N_{61}O_{57}S_1$ | 4496 | 4502 |
| 4.3 | 8 | GPSQPTYPGDDAPVEDLIRFYRDLRRYLNVVTRHRYC$^{acetyl}$-$_{NH2}$ | $C_{199}H_{303}N_{60}O_{58}S_1$ | 4497 | 4504 |
| 5.2 | 9 | GPSQPTYPGDDAPVRDLIRFYRDLQRYLRVVTRHRYC$^{acetyl}$-$_{NH2}$ | $C_{201}H_{311}N_{63}O_{56}S_1$ | 4538 | 4545 |

TABLE 1-continued

Mass spectral characterization of miniature proteins and peptides.

| Name | SEQ ID NO: | Sequence | Formula | Calc (+m/z) | Meas |
|---|---|---|---|---|---|
| 5.3 | 10 | GPSQPTYPGDDAPVRDLIRFYRDLRRYLNVVTRHRYC$^{acetyl}$-NH2 | $C_{200}H_{308}N_{63}O_{56}S_1$ | 4524 | 4531 |
| 6.3 | 11 | GPSQPTYPGDDAPVRDLRRFYRDLRRYLNVVTRHRYC$^{acetyl}$-NH2 | $C_{200}H_{309}N_{67}O_{57}S_1$ | 4567 | 4573 |

| Name | SEQ ID NO: | Fluorescein Labeled Sequences | Formula | Calc (+m/z) | Meas |
|---|---|---|---|---|---|
| aPP$^F$ | 12 | GPSQPTYPGDDAPVEDLIRFYNDLQQYLNVVTRHRYC$^{FLU}$-NH2 | $C_{215}H_{302}N_{55}O_{65}S_1$ | 4729 | 4735 |
| 2.1$^F$ | 13 | GPSQPTYPGDDAPVEDLIRFYNDLQRYLNVVTRHRYC$^{FLU}$-NH2 | $C_{216}H_{306}N_{57}O_{64}S_1$ | 4758 | 4763 |
| 2.2$^F$ | 14 | GPSQPTYPGDDAPVEDLIRFYRDLQQYLNVVTRHRYC$^{FLU}$-NH2 | $C_{217}H_{308}N_{58}O_{64}S_1$ | 4777 | 4778 |
| 3.2$^F$ | 15 | GPSQPTYPGDDAPVEDLIRFYRDLQRYLNVVTRHRYC$^{FLU}$-NH2 | $C_{218}H_{312}N_{59}O_{63}S_1$ | 4800 | 4806 |
| 4.2$^F$ | 16 | GPSQPTYPGDDAPVRDLIRFYRDLQRYLNVVTRHRYC$^{FLU}$-NH2 | $C_{219}H_{317}N_{63}O_{61}S_1$ | 4827 | 4834 |
| 4.3$^F$ | 17 | GPSQPTYPGDDAPVEDLIRFYRDLRRYLNVVTRHRYC$^{FLU}$-NH2 | $C_{219}H_{316}N_{62}O_{62}S_1$ | 4828 | 4828 |
| 5.2$^F$ | 18 | GPSQPTYPGDDAPVRDLIRFYRDLQRYLRVVTRHRYC$^{FLU}$-NH2 | $C_{221}H_{323}N_{64}O_{60}S_1$ | 4870 | 4871 |
| 5.3$^F$ | 19 | GPSQPTYPGDDAPVRDLIRFYRDLRRYLNVVTRHRYC$^{FLU}$-NH2 | $C_{220}H_{321}N_{64}O_{60}S_1$ | 4855 | 4855 |
| 6.3$^F$ | 20 | GPSQPTYPGDDAPVRDLRRFYRDLRRYLNVVTRHRYC$^{FLU}$-NH2 | $C_{220}H_{322}N_{68}O_{60}S_1$ | 4989 | 4903 |

| Name | SEQ ID NO: | Rhodamine Labeled Sequences | Formula | Calc (+m/z) | Meas |
|---|---|---|---|---|---|
| aPP$^R$ | 21 | K$^{Rhod}$GPSQPTYPGDDAPVEDLIRFYNDLQQYLNVVTRHRY-NH2 | $C_{223}H_{323}N_{57}O_{66}S_2$ | 4907 | 4906 |
| 4.2$^R$ | 22 | K$^{Rhod}$GPSQPTYPGDDAPVRDLIRFYRDLQRYLNVVTRHRY-NH2 | $C_{227}H_{338}N_{64}O_{61}S_2$ | 5008 | 5007 |
| 4.3$^R$ | 23 | K$^{Rhod}$GPSQPTYPGDDAPVEDLIRFYRDLRRYLNVVTRHRY-NH2 | $C_{227}H_{337}N_{63}O_{62}S_2$ | 5005 | 5004 |
| 5.2$^R$ | 24 | K$^{Rhod}$GPSQPTYPGDDAPVRDLIRFYRDLQRYLRVVTRHRY-NH2 | $C_{229}H_{344}N_{66}O_{60}S_2$ | 5046 | 5045 |
| 5.3$^R$ | 25 | K$^{Rhod}$GPSQPTYPGDDAPVRDLIRFYRDLRRYLNVVTRHRY-NH2 | $C_{228}H_{342}N_{66}O_{60}S_2$ | 5032 | 5031 |
| ZF 5.3$^R$ | 26 | K$^{Rhod}$WYSCNVCGKAFVLSRHLNRHLRVHRRAT-NH2 | $C_{181}H_{276}N_{58}O_{41}S_4$ | 4047 | 4049 |
| Tat$^R$ | 27 | K$^{Rhod}$GRKKRRQRRRPPQY-NH2 | $C_{112}H_{181}N_{41}O_{24}S_2$ | 2550 | 2549 |
| Arg$_8^R$ | 28 | K$^{Rhod}$RRRRRRRR-NH2 | $C_{81}H_{138}N_{37}O_{15}S_2$ | 1934 | 1935 |

| Name | SEQ ID NO: | Dexamethasone Labeled Sequences | Formula | Calc (+m/z) | Meas |
|---|---|---|---|---|---|
| aPP$^{Dex}$ | 29 | K$^{Dex}$GPSQPTYPGDDAPVEDLIRFYNDLQQYLNVVTRHRY-NH2 | $C_{231}H_{326}F_1N_{55}O_{64}S_1$ | 4828 | 4826 |
| 4.2$^{Dex}$ | 30 | K$^{Dex}$GPSQPTYPGDDAPVRDLIRFYRDLQRYLNVVTRHRY-NH2 | $C_{225}H_{341}F_1N_{62}O_{60}S_1$ | 4926 | 4925 |
| 4.3$^{Dex}$ | 31 | K$^{Dex}$GPSQPTYPGDDAPVEDLIRFYRDLRRYLNVVTRHRY-NH2 | $C_{225}H_{340}F_1N_{61}O_{61}S_1$ | 4927 | 4926 |
| 5.2$^{Dex}$ | 32 | K$^{Dex}$GPSQPTYPGDDAPVRDLIRFYRDLQRYLRVVTRHRY-NH2 | $C_{227}H_{347}F_1N_{64}O_{59}S_1$ | 4968 | 4968 |
| 5.3$^{Dex}$ | 33 | K$^{Dex}$GPSQPTYPGDDAPVRDLIRFYRDLRRYLNVVTRHRY-NH2 | $C_{226}H_{345}F_1N_{64}O_{59}S_1$ | 4954 | 4951 |
| ZF$^{Dex}$ | 34 | K$^{Dex}$WYSCNVCGKAFVLSAHLNQHLAVHTQAT-NH2 | $C_{169}H_{252}F_1N_{43}O_{43}S_3$ | 3 687 | 3688 |
| ZF 5.3$^{Dex}$ | 35 | K$^{Dex}$WYSCNVCGKAFVLSRHLNRHLRVHRRAT-NH2 | $C_{179}H_{279}F_1N_{56}O_{40}S_3$ | 3968 | 3968 |
| Tat$^{Dex}$ | 36 | K$^{Dex}$GRKKRRQRRRPPQY-NH2 | $C_{110}H_{182}F_1N_{39}O_{23}S_1$ | 2472 | 2472 |
| Arg$_8^{Dex}$ | 37 | K$^{Dex}$RRRRRRRR-NH2 | $C_{79}H_{141}F_1N_{35}O_{14}S_1$ | 1856 | 1857 |

| Name | SEQ ID NO: | Sequence |
|---|---|---|
| SAH-p53-4 | 38 | LSQETFDLWKLLEN |
| SAH-p53-4-5.3 | 39 | RSQERFRLWRRLEN |
| SAH-p53-8 | 40 | QSQQTFNLWRLLQN |

TABLE 1-continued

Mass spectral characterization of miniature proteins and peptides.

| Name | SEQ ID NO: | Sequence |
|---|---|---|
| SAH-p53-8-5.3 | 41 | RSQQRFRLWRRLQN |

| Name | SEQ ID NO: | Sequence |
|---|---|---|
| aPP | 58 | GPSQPTYPGDDAPVEDLIRFYNDLQQYLNVVTRHRY |
| 2.1 | 59 | GPSQPTYPGDDAPVEDLIRFYNDLQRYLNVVTRHRY |
| 2.2 | 60 | GPSQPTYPGDDAPVEDLIRFYRDLQQYLNVVTRHRY |
| 3.2 | 61 | GPSQPTYPGDDAPVEDLIRFYRDLQRYLNVVTRHRY |
| 4.2 | 62 | GPSQPTYPGDDAPVRDLIRFYRDLQRYLNVVTRHRY |
| 4.3 | 63 | GPSQPTYPGDDAPVEDLIRFYRDLRRYLNVVTRHRY |
| 5.2 | 64 | GPSQPTYPGDDAPVRDLIRFYRDLQRYLRVVTRHRY |
| 5.3 | 65 | GPSQPTYPGDDAPVRDLIRFYRDLRRYLNVVTRHRY |
| 6.3 | 66 | GPSQPTYPGDDAPVRDLRRFYRDLRRYLNVVTRHRY |
| TatR | 67 | GRKKRRQRRRPPQY |
| Arg8R | 68 | RRRRRRRR |
| ZF | 69 | WYSCNVCGKAFVLSAHLNQHLAVHTQAT |
| ZF5.3 | 70 | WYSCNVCGKAFVLSRHLNRHLRVHRRAT |
| ZFN1 | 71 | FQCRICMRNFSDRSNLSRHIRTHTP |
| ZFN2 | 72 | FACDICGRKFAISSNLNSHTKIHTP |
| ZFN3 | 73 | FQCRICMRNFSRSDNLARHIRTHTP |
| ZFN4 |  | FACDICGRKFATSGNLTRHTKIHLR |

Figure 19:
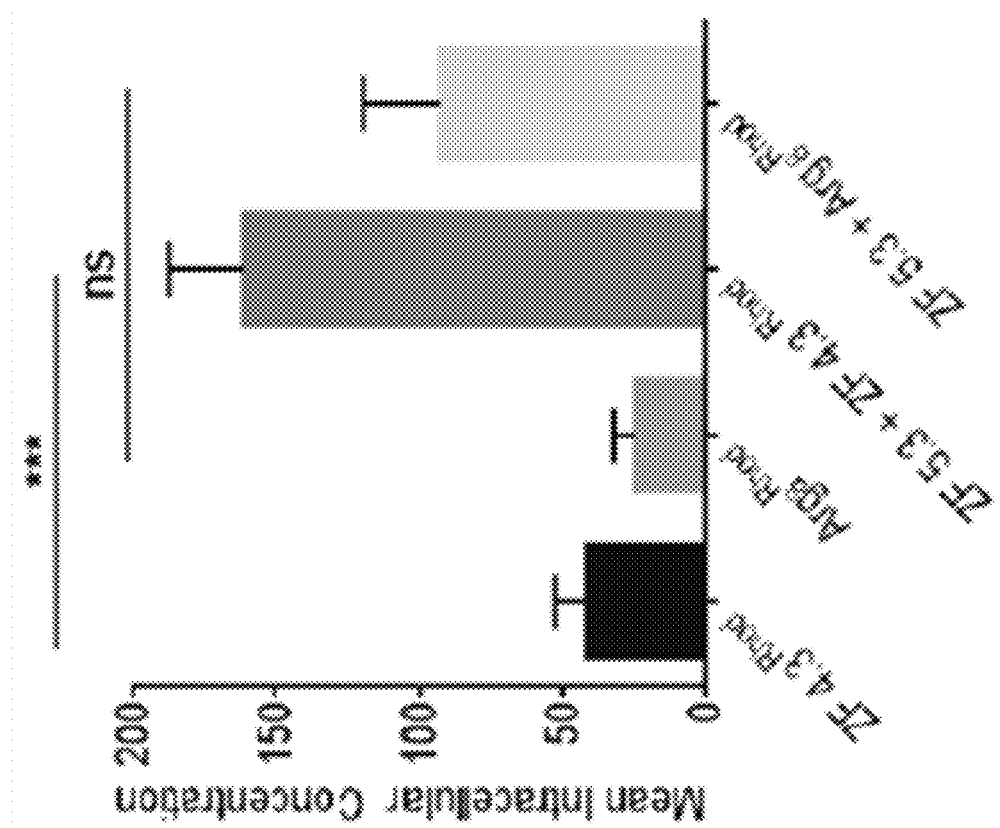
FIG. 19 depicts the results of experiments demonstrating that the cytosolic concentration of ZF 4.3 is significantly elevated in the presence of ZF 5.3, while the cytosolic concentration of Arg8 does not significantly change. The amino acid sequence of Arg8 is provided in SEQ ID NO:68.

Example 2: Co-Administration of ZF 5.3 and Non-Covalently Linked Cargo Delivers Cargo to the Cytosol HeLa cervical cancer cells were incubated in the presence of either 500 nM ZF 4.3-Rhodamine or 500 nM ZF 4.3-Rhodamine with 1 µM ZF 5.3 for 30 minutes. After incubation, external peptide was removed and internal peptide concentration was measured using a microscope with advanced correlation and detection hardware. In the absence of ZF 5.3, only a small amount of ZF 4.3 enters the cell interior, corresponding to ~8% of the ZF 4.3 concentration added (FIG. 19). In the presence of ZF 5.3, the amount of ZF 4.3 that enters the cell interior quadrupled, raising to ~35% of the concentration added (FIG. 19). In contrast, co-incubation of HeLa cells with ZF 5.3 and the canonical peptide octaarginine (Arg8; SEQ ID NO:68) did not significantly increase intracellular Arg8 (SEQ ID NO:68) concentrations.

Figure 20:
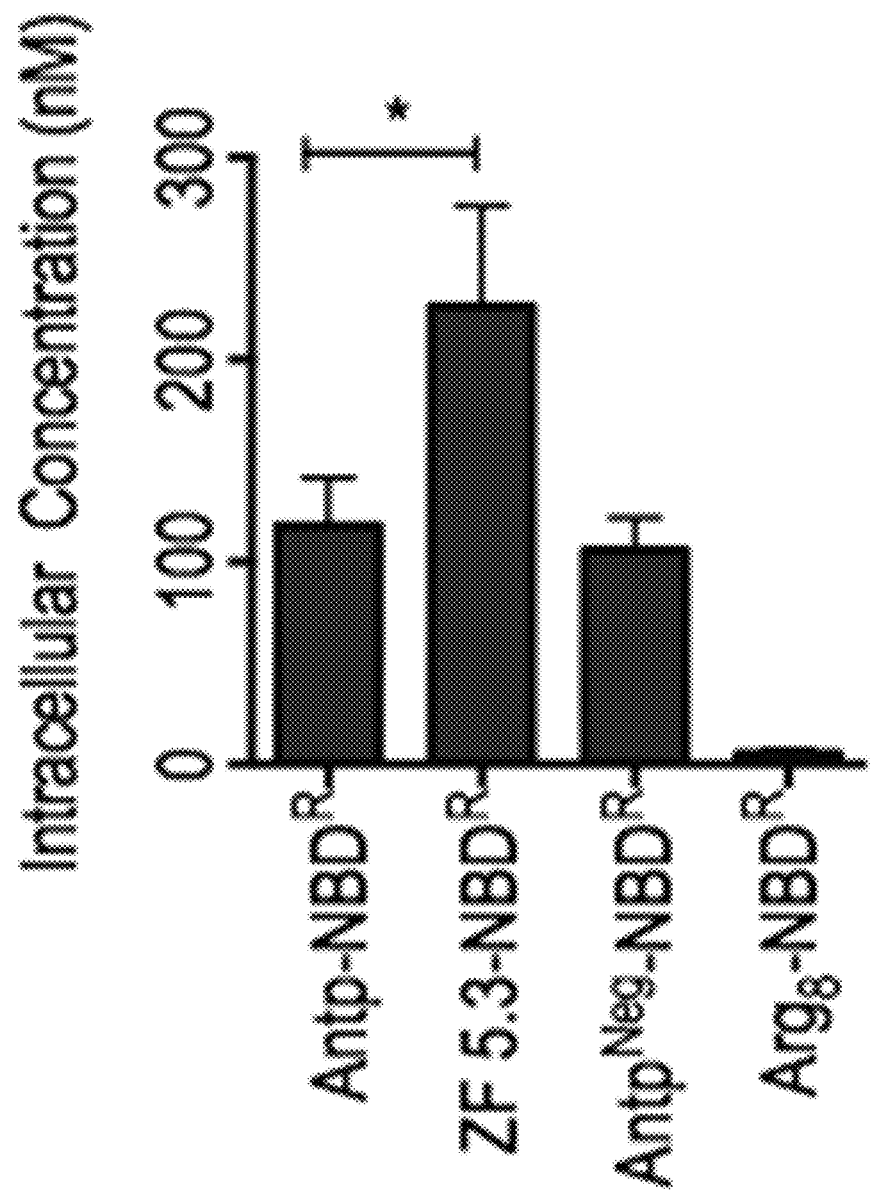
FIG. 20 depicts the results of an experiment demonstrating that ZF5.3 is superior to both Antp and R8 for trafficking a biologically active peptide into the cytosol. The amino acid sequence of Arg8 is provided in SEQ ID NO:68.
Figure 21:
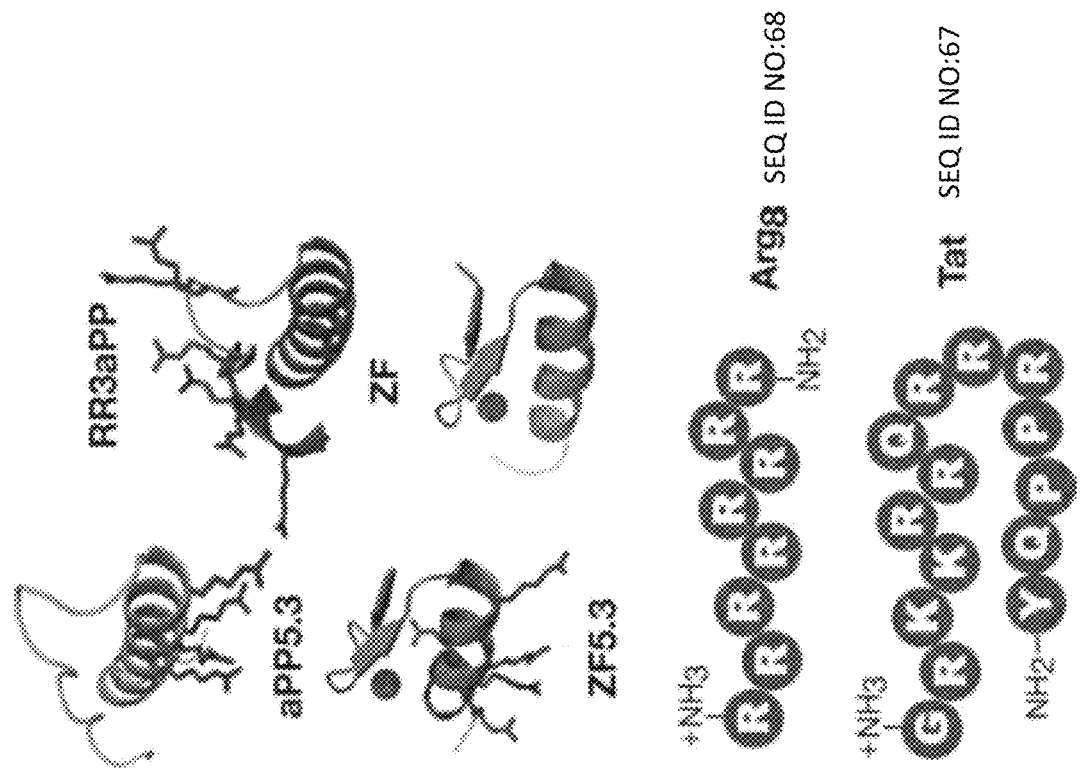
FIG. 21 depicts examples of the peptides and protein domains evaluated in this work. Arginine side chains are shown explicitly in those molecules drawn as ribbons (Daniels and Schepartz, 2007, J. Am. Chem. Soc. 129:14578-14579; Smith et al., 2008, J. Am. Chem. Soc. 130:2948-2949).

Example 3: ZF5.3 is superior to both Antp and Arg8 (SEQ ID NO:68) for trafficking a biologically active peptide into the cytosol Cells were incubated in the presence of either 500 nM ZF 5.3-NBD or Antp-NBD or Arg8-NBD (FIG. 20). After incubation, internal peptide concentration was measured.

Example 4: Improved Assays for Determining the Cytosolic Access of Peptides, Proteins, and their Mimetics Proteins and other macromolecules that cross biological membranes have great potential as tools for research and next-generation therapeutics. Described herein are two assays that effectively quantify the cytosolic localization of a number of peptides and protein domains. One assay, called GIGI (glucocorticoidinduced eGFP induction), is an amplified assay that informs on relative cytosolic access without the need for sophisticated imaging equipment or adherent cells. The second, called GIGT (glucocorticoid-induced eGFP translocation), is a nonamplified assay that informs on relative cytosolic access and exploits sophisticated imaging equipment to facilitate high-content screens in live cells. Each assay was employed to quantify the cytosolic delivery of several canonical "cell permeable peptides," as well as minimally cationic miniature proteins and zinc finger nuclease domains. The results described herein show definitively that both overall charge as well as charge distribution influence cytosolic access and that small protein domains containing a discrete, helical, penta-Arg motif can dramatically improve the cytosolic delivery of small folded proteins such as zinc finger domains. The assays described herein will prove useful to explore and discover the fundamental physicochemical and genetic properties that influence both the uptake and endosomal release of peptidic molecules and their mimetics.

In the studies described herein, significant improvements of two assays used that evaluate the intramembrane trafficking and cytosolic delivery of peptides and protein conjugates are described. The improvements increase assay speed, sensitivity, and versatility, and decrease assay cost-per-well. One assay (GIGI) is based on an amplified read-out that informs on cytosolic delivery without the need for sophisticated imaging equipment or adherent cells. The second assay (GIGT) is based on a nonamplified read-out and informs on relative cytosolic delivery in a way that exploits the unique capabilities of sophisticated imaging equipment. With these assays, it is shown that both overall charge and charge distribution influence the efficiency of endosomal release into the cytosol and that inclusion of a helical, penta-Arg motif can dramatically increase the cytosolic delivery of small proteins and zinc finger domains.

One non-limiting example of the use of this assay includes an application that combines the GIGT assay with an image-based, genome-wide interference screen to identify those gene products whose knockdown increase endosomal release and in this way identify those elements of the trafficking machinery that engage the penta-Arg motif. These studies will be useful for discovering fundamentally new elements of cellular machinery and/or new molecular targets whose modulation by small molecules could further improve peptide/peptide mimetic function. Another non-limiting example of the use of this assay includes a complementary application that exploits the GIGI assay to sort large molecular libraries whose members contain variations on the penta-Arg motif to further improve cytosolic trafficking.

The methods and materials used in the Example are now described.

Reagents

All Fmoc-protected amino acids required for peptide synthesis were purchased from Novabiochem. PAL-Rink Amide resin was obtained from PE Biosystems. Amino acid coupling reagents were purchased from Peptides International. N,N-diisopropylethylamine (DIEA) and piperidine were purchased from Sigma Aldrich. N,N-dimethylformamide (DMF) was purchased from J. T. Baker. Trifluoroacetic acid (TFA) was obtained from Acros organics. Unless otherwise stated, all other reagents were obtained from commercial sources and used without further purification. SDex was synthesized as previously described (Kwon and Kodadek, 2007, Chem Biol 14:671-677; Liu et al., 2005, J Am Chem Soc 127:8254-8255).

Peptide Synthesis

All peptides evaluated in this work were synthesized on a 50 mmol scale using PAL-Rink Amide resin (0.34 mmol/g) and standard solid phase methods (Appelbaum et al., 2012, Chem Biol 19:819-830; Kritzer et al., 2006, ChemBioChem 7:29-31). The resin was washed thoroughly between each coupling and deprotection step using DMF and DCM. All amino acid couplings and deprotection reactions were performed using an automated peptide synthesizer (Liberty, CEM) or a microwave-accelerated reaction system (MARSS System, CEM). Amide bond formation was achieved using 5 equivalents of amino acid, 5 equivalents of HCTU and 10 equivalents of DIEA in DMF. Fmoc groups were removed upon treatment with 20% piperidine in DMF containing 0.1 M HOBt to minimize aspartimide formation.

Tagging Peptides with SDex

Resin-bound peptides were tagged with SDex using procedures described previously (Appelbaum et al., 2012, Chem Biol 19:819-830). Briefly, Na(Boc)-Ne(Fmoc)-lysine-OH was coupled onto the N-terminus of a resin-bound peptide using the amide bond forming conditions described above. Deprotection of the Ne(Fmoc) lysine sidechain was achieved upon incubation with 20% piperidine in DMF containing 0.1 M HOBt. Following Ne(Fmoc) deprotection, 2.5 equivalents SDex, 2.5 equivalents HOAt, 2.5 equivalents HATU, 10 equivalents DIEA and 7 equivalents 2,6 lutidine in 3 mL DMF were added to the resin and the reaction was shaken for 18 h at room temperature on an orbital shaker. The resin was then thoroughly washed with DMF, DCM and methanol and dried under nitrogen overnight.

Cleavage and Purification of SDex-Labeled Peptides

SDex-labeled peptides were fully deprotected and cleaved from resin using 5 mL of a cleavage cocktail containing 92.5% TFA, 2.5% water, 2.5% triisopropylsilane and 2.5% 3,6-dioxa-1,8-octanedithiol and incubating at 38° C. for 30 min in a microwave reactor (MARSS System, CEM). The peptide was precipitated using cold diethyl ether (40 mL), pelleted by centrifugation, resuspended in 20 mL 10% acetonitrile in water, frozen and lyophylized to dryness. Peptides were purified across a reverse-phase C8 column (YMCbasic, 150 mm×10 mm ID) or a C18 column (VYDAC, 250 mm×10 mm ID) with a Varian ProStar HPLC system and eluted over 55 minutes with a linear gradient of 15% to 70% Solvent B (0.1% TFA in acetonitrile) over Solvent A (0.1% TFA in water). Purified fractions were collected, combined, frozen and lyophilized to dryness. Peptide powders were then reconstituted in water to a final concentration of 1 mM and stored at 4° C. protected from light. Peptide concentrations were quantified using an SDex extinction coefficient of 12,000 M-1 cm-1 at 242 nm in water as described previously.3, 5 Identity and purity of all peptides were confirmed by mass spectrometry (see Table 5) and analytical RP-HPLC. All peptides were purified to >95% purity as analyzed by product peak integration of representative analytical RP-HPLC chromatograms. Mass data was obtained from a Waters QTOF LC-MS.

Plasmids

To generate pG5-eGFP, pG5-Luc (Promega, Fitchburg, Wis.) was first treated with BglII and FseI to remove the luciferase-coding region, and purified the digested plasmid (Qiagen, #28704). Next, PCR was used to amplify the eGFP coding region (amino acids 1-241) from pEGFPN3 (Addgene, Cambridge, Mass.) using primers (5'-GCGCTAG-GATCCATCGCCACCATGGTGAGCAAG-3' (SEQ ID NO:42) and 5'-CCATGGCCGGCCGCGGCCGCTT-TACTTGTACAG-3'(SEQ ID NO:43)) containing BamHI and FseI restriction sites. The resulting PCR product was purified (Qiagen, #28106), digested with BamHI and FseI, and ligated to the digested plasmid derived from pG5-Luc using T4 DNA ligase (New England Biolabs, #M02025). The final sequence of pG5-eGFP was confirmed by sequencing using a forward primer complementary to the coding region upstream of the Gal4 binding site: 5'-GGAGGACAGTACTCCGTCTAGAAACTC-3' (SEQ ID NO:44). pGal4-GRH-VP16 was generated, beginning with pEGal4DBD-GRLBD-VP165 (Tom Kodadek, Scripps Research Institute) and installing the C to G substitution at position 291 of Gal4-GR-VP16 using site-directed mutagenesis (Stratagene, #200521) and primers 5'-GAGAATGACTCTACCCGGCATGTACGACCAATG-3' (SEQ ID NO:45) and 5'-CTCTTACT-GAGATGGGCCGTACATGCTGGTTAC-3' (SEQ ID NO:46). Plasmid pK7-GRH-GFP was constructed by modifying the GR LBD of pk7-GR-GFP6 (Addgene Plasmid 15534, Cambridge, Mass.) with a C to G mutation at position 638 via site-directed mutagenesis (Stratagene, #200521). The C to G mutation was installed using forward primer 5'-GAGAATGACTCTACCCGGCATGTACGACC- 3' (SEQ ID NO:47) and reverse primer 5'-GGTCGTA-CATGCCGGGTAGAGTCATTCTC-3' (SEQ ID NO:48). Successful mutagenesis of pK7-GRH-GFP was confirmed via sequencing using forward primer 5'-GGTGGAGAT-CATATAGACAATCAAGTGC-3' (SEQ ID NO:49) complementary to the coding region upstream of the desired mutation site. To generate plasmids for stable Saos2 transfection, the glucocorticoid receptor open reading frame was amplified from pk7-GRH-GFP using forward primer 5'-GCCTT-GAGCTCGACTCCAAAGAATCAT-TAACTCCTGGTAGAGAAG-3' (SEQ ID NO:50) and reverse primer 5'-GGTCCGGATCCTCACTTTTGAT-GAAACAGAAGTTTTTTGATATTTC-3' (SEQ ID NO:51) and ligated into the pEGFP-C3 vector between BamH1 and SacI restriction sites. Insertion was confirmed via restriction digestion and the plasmid was named pGRH-eGFP.

Cell Culture

HEK293T (ATCC, Manassas, Va., #CRL-11268) and HeLa (ATCC, #CCL-2) cells were grown on 10 cm plates (BD, #353003) and maintained at 37° C. under 5% CO2 in Dulbecco's modified Eagle's medium (Life Technologies, #11995-073) supplemented with 10% fetal bovine serum (FBS), 100 U/mL penicillin and 100 mg/mL streptomycin (pen/strep). This media is referred to as 'full DMEM'. U2OS cells (ATCC, HTB-96) were grown on 10 cm plates (BD, #353003) and maintained at 37° C. in an atmosphere containing 5% CO2 in McCoy's 5A medium (HyClone, #SH30200.01) supplemented with 10% FBS and pen/strep. This media is referred to as 'full McCoy's 5A'. Stable U2OS(GIGI) cells were grown on 10 cm plates (BD, #353003) and maintained at 37° C. under 5% CO2 in full McCoy's 5A medium (HyClone, #SH30200.01) supplemented with 500 mg/mL Geneticin (American Bioanalytical, #AB05058-00020). Saos2(GIGT) cells were grown in full McCoy's 5A medium supplemented with 200 mg/mL Geneticin. Cells were allowed to grow to approximately 80% confluence before subculture.

Transfection of GIGI Component Plasmids

Cells were plated (4,000 cells/well) on black, 384-well plates (Corning, #3571) in full DMEM (HeLa or HEK293T) or full McCoy's 5A (U2O5) and allowed to adhere overnight. The full volume of media was then removed and the cells were overlaid with Opti-MEM reduced serum media (Life Technologies, #31985-070) containing 0.33 mg/ml pGal4-GR-VP16 or pGal4-GRH-VP16, 1.33 mg/ml pG5-eGFP and 0.01 mg/ml pmCherry (pmCherry-N1, Clonetech) complexed with Lipofectamine 2000 (Life Technologies, #11668-091). Cells were allowed to transfect for 8 h at 37° C. under 5% CO2 before treatments.

Development of Stable Saos2(GIGT) Cells

Low passage Saos-2 (ATCC #HTB-85) bone osteosarcoma cells were transfected with GRH-GFP plasmid DNA using standard Lipofectamine 2000 methods (Invitrogen). Stable transfectants were selected with McCoy's 5A supplemented with 10% FBS, pen/strep and 700 mg/mL G418 for 14 days, replenishing media every three days. Isolated viable colonies were collected using sterile 3 mm cloning disks (Scienceware, #Z374431) soaked in 0.25% trypsin-EDTA. Green colonies were identified by epifluorescence microscopy, isolated from the population and sorted multiple times on a FACS Vantage cell sorter (Yale Cell Sorting Facility) to enrich the brightest cells.

Transfection of GIGT Component Plasmids

Cells were plated (10,000 cells/well) onto 96-well glass bottom plates (Matrical Bioscience, #MGB096-1-2-LG-L) in full DMEM (HeLa) or full McCoy's 5A (U205) media and allowed to adhere overnight. After adherence, growth media was removed and the cells were overlaid with Opti-MEM reduced serum media (Life Technologies, #31985-070) supplemented with 1.333 mg/mL pk7-GR-GFP or pk7-GRH-GFP complexed with Lipofectamine 2000 (Life Technologies, #11668-091). Cells were allowed to transfect for 6 h at 37° C. under 5% CO2 before removing transfection media and replenishing growth media. Image analysis of GIGT using Cell Profiler. Cell image files were loaded into a customizable CellProfiler7 'pipeline' as individual GFP (green) and Hoechst (blue) channels, and converted to grayscale. Nuclei were identified and segmented from the gray Hoechst channel based on Otsu three-class thresholding, with pixels in the middle intensity class assigned to background. Clumped objects were individually distinguished using 'Laplacian of Gaussian' modeling and separated by 'shape'. The diameters of the nuclei were expanded by 2 mm and the nuclear region was subtracted from the enlarged area to generate a 'cytosolic' region. The ratio of mean intensities of the nuclear region divided by the cytosolic region of the GFP image was measured for every cell examined, and 40-80 transfected cells from 15-25 images were acquired for each treatment.

Quantifying GIGI in Cell Lysates

Cells were transfected with GIGI component plasmids and transferred immediately to either full DMEM (for HeLa or HEK293T cells) or full McCoy's 5A (for U2OS cells) media that in certain cases was supplemented with the indicated Dexconjugate. Cells were incubated with ligand for 24 h at 37° C. under 5% CO2 before analysis. To reduce background, stable U2OS(GIGI) cells were switched to McCoy's 5A media supplemented with 5% charcoal-stripped FBS and penicillin/streptomycin (CS-5A) 24 h before the addition of ligand. Following incubation, the treatment medium was removed, and the cells were lysed in 1×RIPA buffer (0.5 M Tris-HCl, pH 7.4, 1.5 M NaCl, 2.5% deoxycholic acid, 10% NP-40, and 10 mM EDTA) (Millipore, #20-188) containing 1×EDTA-free protease inhibitor (Roche, #11836170001) at room temperature for 15 min in the dark. Fluorescence intensities of each volume of the cell lysate were quantified using a fluorescence plate reader (Analyst AD, LJL Biosystems). To measure eGFP fluorescence intensity, excitation and emission wavelengths were set to 485 and 530 nm, respectively. To measure RFP fluorescence intensity, excitation and emission wavelengths were set to 530 and 580 nm, respectively. Relative fluorescence units (RFUs) were calculated as shown in Equation 1, and dose-response curves are represented by the best fit of the data to Equation 2. RFUs are expressed±standard deviation (Excel). The maximum induction level is defined as RFUmax. Data were processed using Kaleidagraph and GraphPad Prism software.

$$RFU = ([I_{530}]/[I_{580}]) - ([I'_{530}]/[I'_{580}]) \qquad (1)$$

$[I_{530}]$=fluorescence intensity at 530 nm in treated cells, $[I_{580}]$=fluorescence intensity at 580 nm in treated cells, $[I'_{530}]$=fluorescence intensity at 530 nm in untreated cells, and $[I'_{580}]$=fluorescence intensity at 580 nm in untreated cells.

$$Y = Y_{min} + (Y_{max} - Y_{min})/(1 + 10^{logEC50 - X}) \qquad (2)$$

Y is relative fluorescence units (RFU) or translocation ratio (TR), $Y_{max}$ and $Y_{min}$ are the maximal and minimal values at each concentration of ligand, X is the [ligand], and EC50 is the ligand concentration that corresponds to $Y_{max}/2$.

Epifluorescence Microscopy (GIGI)

Cells were plated at a density of 10,000 cells/well in full DMEM (HeLa or HEK293T) or full McCoy's 5A (U2OS or U2OS(GIGI)) on 96-well glass bottom plates (Matrical Bioscience, #MGB096-1-2-LG-L) and allowed to adhere overnight. For transient GIGI assays, the cells were transfected as described elsewhere herein. Following transfection, the cells were immediately switched to full DMEM (HeLa and HEK293T) or full McCoy's 5A (U2OS) supplemented with or without ligand as indicated and were allowed to incubate for 24 h at 37° C. under 5% CO2. To reduce background, stable U2OS(GIGI) cells were switched to CS-5A media 24 h before the addition of the ligand. Following treatment, the cells were washed with PBS (Life Technologies, #14190-144), and the nuclei were stained by treating the cells with 1 µg/mL Hoechst 33342 (Molecular Probes, #H3570) in full media for 10 min at 37° C. under 5% CO2. The cells were then washed with PBS and overlaid with HEPES-Krebs-Ringer's (HKR) buffer (140 mM NaCl, 2 mM KCl, 1 mM CaCl2, 1 mM MgCl2, and 10 mM HEPES at pH 7.4) and imaged using a Zeiss Axiovert 200 M epifluorescence microscope outfitted with a Ziess Axiocam MRm camera. Fluorescence illumination was initiated using an EXFO X-cite Series 120 Hg arc lamp. Hoechst 33342 images were acquired using the Zeiss Filter Set #49 (excitation G 365 nm, FT 395, emission BP 445/50), and GFP images were acquired using Zeiss Filter Set #44 (excitation BP 475/50 nm, FT 500, emission BP 530/50 nm). Images were processed using AxioVision 4.8 and ImageJ software.

FACS Analysis (GIGI)

Cells were plated at 50,000 cells/well in full DMEM (HeLa or HEK293T) or full McCoy's 5A (U2OS or U2OS (GIGI)) on 12-well plates (Corning, #3043) and allowed to adhere overnight at 37° C. under 5% CO2. For transient GIGI assays, cells were transfected as described elsewhere herein. Following transfection, the cells were immediately switched to full DMEM (HeLa and HEK293T) or full McCoy's 5A (U2OS) supplemented with or without ligand as indicated and were allowed to incubate for 24 h at 37° C. under 5% CO2. To reduce background, stable U2OS(GIGI) cells were switched to CS-5A media 24 h before the addition of the ligand. Once treatments were complete, the cells were washed with PBS and lifted off the plate with 0.25% trypsin in 1 mM EDTA (Life Technologies, #25200-056). The cells were then resuspended in full DMEM (HEK293T or HeLa), full McCoy's 5A (U2OS) or CS-5A (U2OS(GIGI)), transferred to fresh microfuge tubes (USA Scientific, #1415-2600), and pelleted by centrifugation. After the media were aspirated, the cells were washed with ice cold PBS and pelleted again by centrifugation. The wash solution was aspirated, and the cells were resuspended in ice cold PBS. Cells were then counted using flow cytometetry (Accuri C6, BD, San Jose, Calif.) recording 20,000 events for each experiment. Excitation and emission wavelengths were set to 488 and 533 nm, respectively. Data were gated to include cell populations of viable cells using forward scatter and side scatter filters. Gating was also performed to exclude background fluorescence as determined from untreated cells. Relative emission levels were quantified from histograms plotting count vs fluorescence intensity. Data were processed using FlowJo, Kaleidagraph, and GraphPad Prism software.

Quantifying GIGT in Live Cells

Following transfection, cells were transferred immediately to clear DMEM (Life Technologies, #21063-029) supplemented with or without Dex ligand and 300 nM Hoechst 33342. Cells were allowed to incubate in the presence of ligand for 30 min at 37° C. under 5% CO2. Once the incubation was complete, the media were replaced with HKR imaging buffer, and the cells were imaged using a Zeiss Axiovert 200 M epifluorescence microscope outfitted with a Ziess Axiocam MRm camera. Fluorescence illumination was initiated using an EXFO X-cite Series 120 Hg arc lamp. Hoechst 33342 images were acquired using the Zeiss Filter Set #49 (excitation G 365 nm, FT 395, emission BP 445/50), and GFP images were acquired using Zeiss Filter Set #44 (excitation BP 475/50 nm, FT 500, emission BP 530/50 nm). Fluorescence intensities of individual cells were quantified using the image analysis algorithm CellProfiler.

High-Content Imaging of GIGT in Saos2(GIGT) Cells

Saos2(GIGT) cells were plated onto 384-well plates (2,500 cells/well) in 40 µL of full McCoy's 5A and allowed to adhere overnight. To reduce background translocation, the plating media were removed, and cells were overlaid with clear DMEM (Life Technologies, #21063-029) for 16 h before treatment. Clear DMEM supplemented with ligand (5× concentration, 10 µL) was then added directly to the wells, and the cells were allowed to incubate for 30 min. Following treatment, cells were fixed with 4% paraformaldehyde for 20 min at room temperature and washed with PBS. For imaging, the cells were counter-stained with Hoechst 33342 for 30 min at room temperature and imaged on an Opera high content screening system (PerkinElmer Life and Analytical Sciences) using a 20×0.45 NA lens. GR★-eGFP fluorescence was detected using a solid state 488 nm laser and a 540/75 bandpass filter, while Hoechst 33342 was detected using a 405 nm laser and a 450/50 bandpass filter. Translocation ratios were determined using Acapella high content imaging and analysis software, with a script that processed the images in a manner similar to the CellProfiler pipeline described in the Supporting Information. Each data point represents 30-60 images containing over 100 cells.

Z'-Factor Determination

The Z'-factor (Zhang et al., 1999, J. Biomol. Screening 4:67-73) is a statistical parameter that is used to quantify the suitability of an assay for use in high-throughput screening. The Z'-factor measures the statistical separation of the means and standard deviations between treated and untreated cell populations. A negative Z'-factor value results from substantial overlap between positive and negative control samples and is indicative of a weak assay. More robust separation between the sample populations gives positive Z'-factor values, approaching 1 as separation increases toward infinity. Values were calculated using Equation 3 and were determined for GIGI and GIGT experiments with sample sizes ranging from n=60 to 150.

$$Z\text{-factor} = 1 - (3(\sigma_1 + \sigma_2 / |\mu_1 - \mu_2|)) \quad (3)$$

In Equation 3, σ1 is the standard deviation of the treated sample, σ2 is the standard deviation of the untreated sample (control), µ1 is the mean of the treated sample, and µ2 is the mean of the untreated sample (control). (Zhang et al., 1999, J. Biomol. Screening 4:67-73).

The results of this Example are now described.

Developing Methodology: GIGI Design and Rationale

The design of GIGI (FIG. 22A) began with an assay reported almost a decade ago by Kodadek and co-workers (Yu et al., 2005, Nat. Biotechnol. 23:746-751). In this assay, cells are transfected with a plasmid encoding an artificial transcription factor composed of a glucocorticoid receptor ligand-binding domain (GR), a Gal4 DNA binding domain (Gal4), and a VP16 transactivation domain (VP16). Cells are also transfected with plasmids encoding a Gal4-driven firefly luciferase reporter gene and a constitutively active *Renilla reniformis* luciferase gene as an internal control (Yu et al., 2005, Nat. Biotechnol. 23:746-751). In the absence of a glucocorticoid ligand (such as Dex or a Dex-tagged peptide or peptide mimetic), the Gal4-GR-VP16 fusion protein remains trapped in the cytosol by tight interactions between the GR and Hsp90 and other chaperones (Galigniana et al., 2010, Nucleus 1:299-308; Grad and Picard, 2007, Mol. Cell. Endocrinol. 275:2-12.). Appearance of glucocorticoid in the cytosol releases these chaperones and reveals nuclear localization sequences within the GR LBD (Picard and Yamamoto, 1987, EMBO J. 6:3333-3340; Beato, 1989, Cell 56:335-344). The subsequent nuclear translocation of the Gal4-GR-VP16 fusion protein activates the expression of a Gal4-driven luciferase reporter gene (Yu et al., 2005, Nat. Biotechnol. 23:746-751; Kwon and Kodadek, 2007, J. Am. Chem. Soc. 129:1508-1509). Because the Gal4-GR-VP16 fusion protein traffics to the nucleus and directs luciferase expression only after direct binding to a Dex-tagged molecule in the cytosol, this technique can be, and has been, used to detect the cytosolic delivery of Dex-tagged peptides and peptide mimetics (Yu et al., 2005, Nat. Biotechnol. 23:746-751; Kwon and Kodadek, 2007, J. Am. Chem. Soc. 129:1508-1509). However, this assay alone does not provide information about the pathway by which a molecule finds its way into the cytosol; additional experimentation is required to differentiate between molecules that diffuse directly across the plasma membrane and those that hijack the endocytic machinery. Although useful and convenient for evaluating compound libraries of modest size, the assay described by Yu et al. does not adapt easily to genomic libraries or live cell visualization. First, the readout is slow. Up to 40 h is required to accumulate measurable levels of luciferase, which hinders its application to small molecule or RNA interference (RNAi) screens that operate on shorter time scales. Second, the assay is costly. The luciferase substrate is expensive, and the reagents needed to perform the assay in 384-well format cost in excess of $100 per plate. This high cost further discourages application of this assay to screen tens of thousands of samples in highthroughput. Finally, it is now well-known that assays based on luciferase activity can be confounded by false positive signals that result from the stabilization of luciferase by allosteric inhibitors. Described herein are a number of simple but effective modifications to the assay described by Yu et al. that overcome all three of these limitations in the context of two complementary assays. The first modification replaces the wild-type GR in the Gal4-GR-VP16 fusion protein with a variant, termed GR★, which possesses significantly improved affinity for Dex and Dex-tagged materials (Chakraborti et al., 1991, J. Biol. Chem. 266:22075-22078; Chakrabortiet al., 1992, J. Biol. Chem. 267, 11366-11373). The second modification replaces the Gal4-driven luciferase reporter gene with one encoding eGFP. These changes reduce the measurement time from 40 h to 6-24 h, eliminate the need for costly luciferase substrates, abolish concerns about false activation by allosteric inhibitors, and allows the assay to be performed in living cells. The third change, embodied in the assay we refer to as GIGT, increases speed even more, to 30 min, by dispensing entirely with transcription and translation and instead directly quantifies the translocation of a GR★ fusion from the cytosol to the nucleus of living cells (FIG. 22B).

Development of GIGI

Figure 23B:
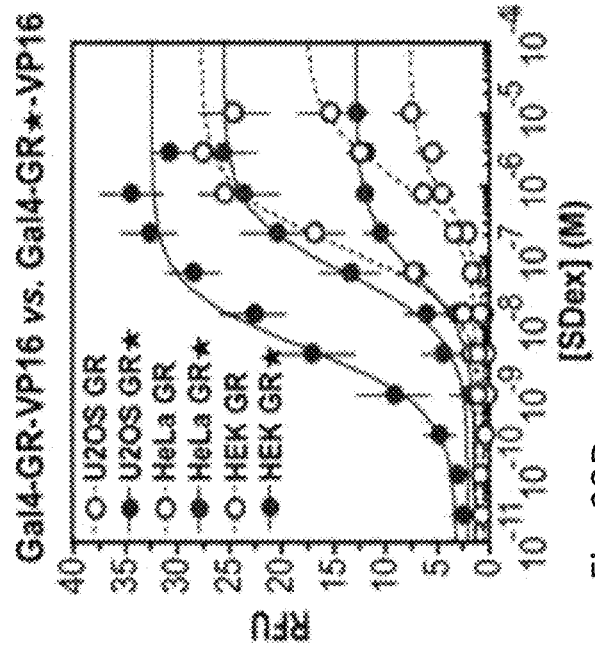
FIGS. 23A-23D, depicts data developed for GIGI validation.
Figure 23A:
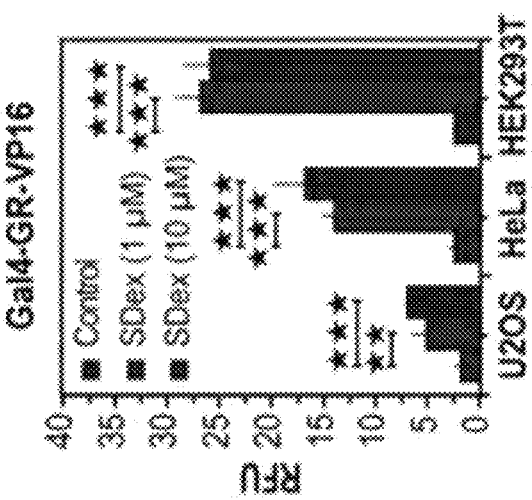
Figure 28:
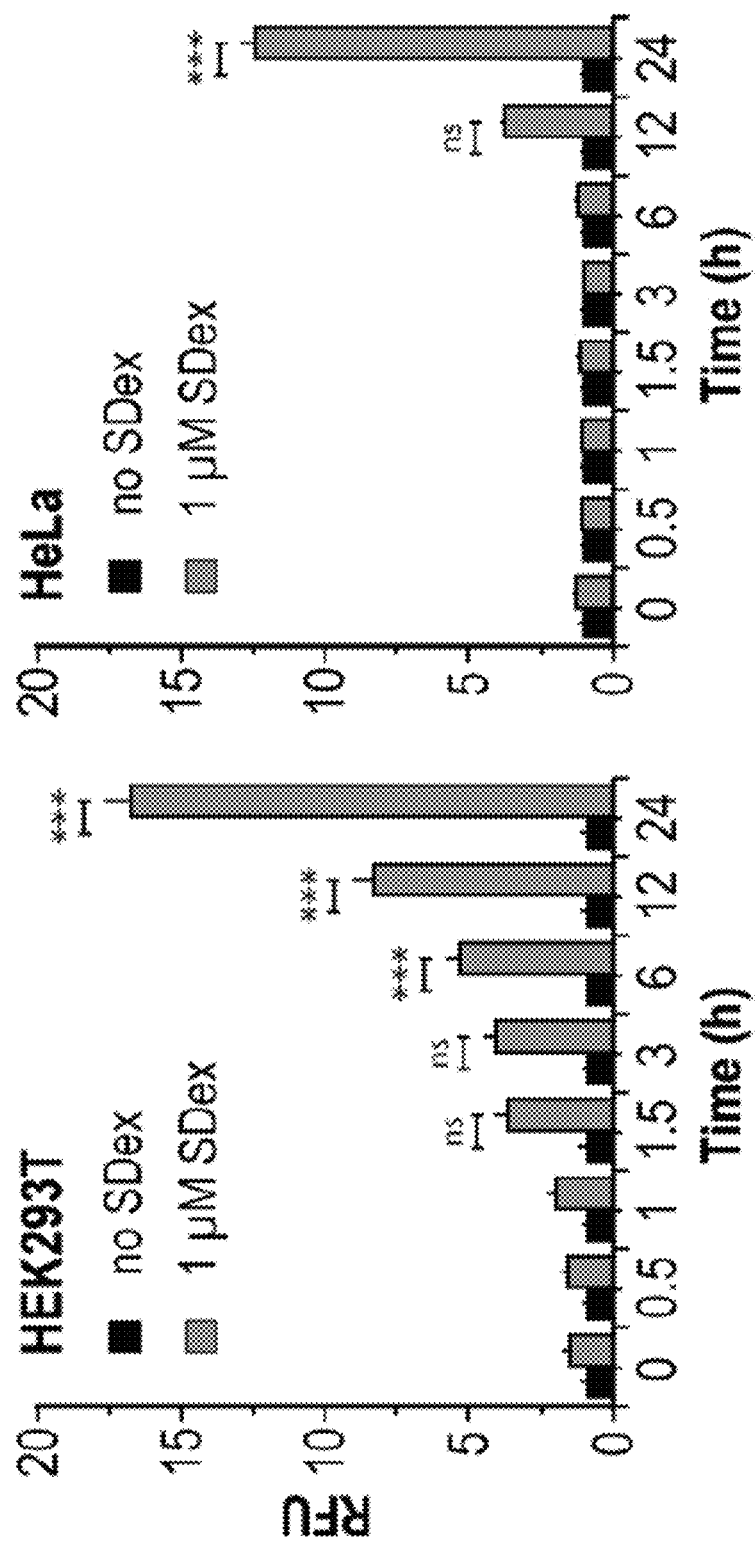
FIG. 28 depicts time-dependent profiles of eGFP expression in SDex-treated cells. HeLa or HEK293T cells were transfected with GIGI component plasmids as described. Following transfection, the cells were switched to full DMEM (10% FBS, pen/strep) supplemented with 1 mM SDex and allowed to incubate for 0-24 h. Following treatment, the cells were lysed and the fluorescence intensity of the lysates was quantified as described. Statistical analyses were performed using a two-tailed Student's t-test. *** p<0.001; ns, not significant.

First, cell lines expressing the Gal4-GR-VP16 fusion protein were assessed for eGFP expression upon treatment with a GR ligand. Three widely used cell lines, U2OS, HeLa, and HEK293T, were transiently transfected with pGal4-GR-VP16 (Yu et al., 2005, Nat. Biotechnol. 23:746-751; Kwon and Kodadek, 2007, J. Am. Chem. Soc. 129:1508-1509) as well as with plasmids encoding the Gal4-driven eGFP reporter plasmid (pG5-eGFP) and a constitutively active mCherry (pmCherry-N1) to provide a measurable control for transfection efficiency and cell viability. Following transfection, cells were treated for 24 h with 1 or 10 µM of the glucocorticoid dexamethasone-21-thiopropionic acid (SDex). The cells were then lysed, and relative eGFP expression levels, conveyed as relative fluorescence units (RFUs), were determined (FIG. 23A). Treatment of HeLa and HEK293T cells expressing the GIGI system with 1 or 10 µM SDex45 led to moderate to strong eGFP expression, whereas lower expression was observed in U2OS cells. Despite these variations, all cells expressed significant levels of eGFP upon treatment with SDex, suggesting that the GIGI assay could be performed in multiple commonly utilized cell lines. To determine whether eGFP could be detected in transiently transfected cells at treatment times less than 24 h, HeLa or HEK293T cells were treated with 1 µM SDex for various times between 30 min to 24 h. Following treatment, the cells were lysed, and relative eGFP expression levels were determined as described above (FIG. 28). Significant eGFP levels were measured in HEK293T cells after 6 h, whereas 24 h were required in HeLa cells.

Improving Sensitivity with a Super GR Variant

Figure 29:
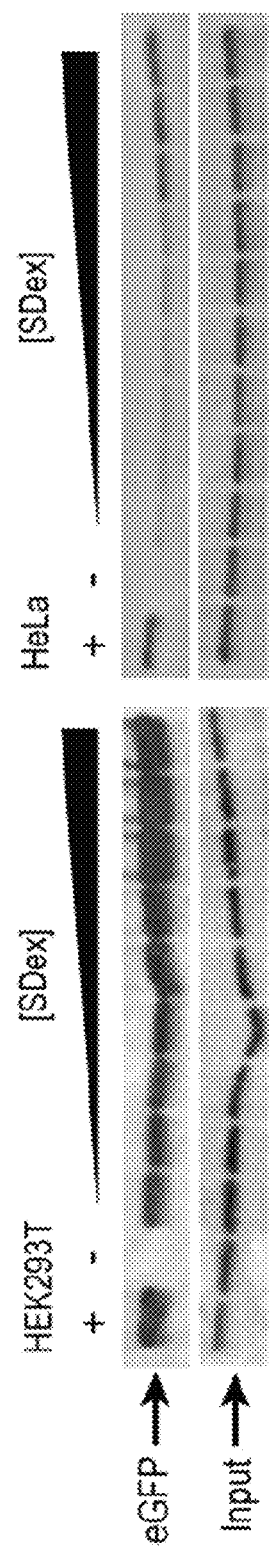
FIG. 29 depicts concentration-dependent eGFP expression in SDex treated cells. HeLa or HEK293T ($1 \times 10^6$ cells) were transiently transfected with GIGI component plasmids as described. As respective positive and negative controls, a subpopulation of cells ($1 \times 10^6$) were transfected with plasmids containing a constitutively active GFP (pGFP-N1, Addgene) or empty vector (pBSKS, Addgene). Following transfection, the cells were overlaid with full DMEM (10% FBS, pen/strep) supplemented with between $10^{-13}$ to $10^{-5}$ M SDex in 10-fold increments and allowed to incubate for 24 h. Following treatment, the cells were lysed in SKL lysis buffer (50 mM HEPES pH 7.6, 150 mM NaCl, 1 mM EDTA pH 8.0, 1 mM EGTA pH 8.0, 1 mM NaF, 1% Triton X-100, 10% glycerol, 1 mM Na3VO4) containing 1×EDTA-free protease inhibitor (Roche) on ice for 45 min. Following lysis, crude lysates were cleared by centrifugation. Total protein concentration of the lysates was quantified using a standard Bradford assay (Bio-Rad). 25 mg protein aliquots were then loaded onto pre-cast 15% polyacrylamide gels (Bio-Rad) and separated by SDS-PAGE. Proteins were detected using chemiluminescence reagent (GE) and antibodies specific for eGFP (Thermo Scientific, clone GFP01) or phosphotyrosine (Millipore, clone 4G10) as a loading control (input). +, pGFP-N1; –, pBSKS.

Many glucocorticoid receptor (GR) variants have been prepared to study the contributions of individual amino acids to steroid affinity, ligand selectivity, and transcriptional activity. One widely studied variant contains a single cysteine to glycine substitution within the ligand-binding domain, at position 656 of the rat GR. The C656 side chain is located near the entrance to the steroid binding pocket and clashes with the steroid C-20 carbonyl oxygen (Chakraborti et al., 1991, J. Biol. Chem. 266:22075-22078; Chakraborti et al., 1992, J. Biol. Chem. 267, 11366-11373). Previous work has shown that, in vitro, rat C656G GR binds Dex with an equilibrium dissociation constant (Kd) of 0.55 nM, about 10-fold more tightly than the wild-type GR ligand-binding domain (Chakraborti et al., 1991, J. Biol. Chem. 266:22075-22078). In cultured H4IIE cells, a similarly mutated full-length GR activated target gene transcription at a 500-fold lower Dex concentration than did the wild-type receptor. On the basis of these results, it was hypothesized that installing the C656G substitution within the Gal4-GR-VP16 fusion protein, to generate Gal4-GR★-VP16, would increase the sensitivity with which Dex-tagged molecules could be detected in the cytosol. To test this hypothesis, HeLa, U2OS, and HEK293T cells were transiently transfected with plasmids encoding either Gal4-GR-VP16 or Gal4-GR★-VP16, along with pG5-eGFP and pmCherry-N1, and treated with between $10^{-11}$ and $10^{-5}$ M SDex. After 24 h, the cells were lysed and relative eGFP expression levels, conveyed as relative fluorescence units (RFU), were quantified. As shown in FIG. 23B, in all cases eGFP production increased with ligand concentration, and the midpoint of the response curve (EC50) was significantly lower when eGFP production was driven by Gal4-GR★-VP16. The effect of the GR★ mutation was most dramatic in HEK293T and HeLa cells, with as much as a 30-fold decrease in EC50; lower fold changes and overall expression levels were observed in U2OS cells (Table 2). HeLa cells transfected with Gal4-GR-VP16 or Gal4-GR★-VP16 were characterized by EC50 values of 771 nM and 30 nM, respectively; the corresponding values for U2OS cells were 577 nM and 44 nM, and 256 nM and 3 nM for HEK293T cells. Western blot experiments in HEK293T and HeLa cells confirmed that the observed fluorescence signals resulted from SDex-induced eGFP expression (FIG. 29).

TABLE 2

Relative EC50, RFUmax and transfection efficiency values for various cell lines as determined by GIGI.

| Cell Line | Gal4-GR-VP16 | | Gal4-GR★-VP16 | | Transfection efficiency* |
|---|---|---|---|---|---|
| | $EC_{50}$ (µM) | $RFU_{max}$ | $EC_{50}$ (µM) | $RFU_{max}$ | |
| U2OS | 0.577 | 7.7 | 0.044 | 13.0 | 19.1% |
| HeLa | 0.771 | 15.5 | 0.030 | 24.6 | 24.1% |
| HEK293T | 0.256 | 27.7 | 0.003 | 34.6 | 18.7% |
| U2OS(GIGI) | N/A | N/A | 0.006 | 13.3 | 85.9% |

Figure 31:
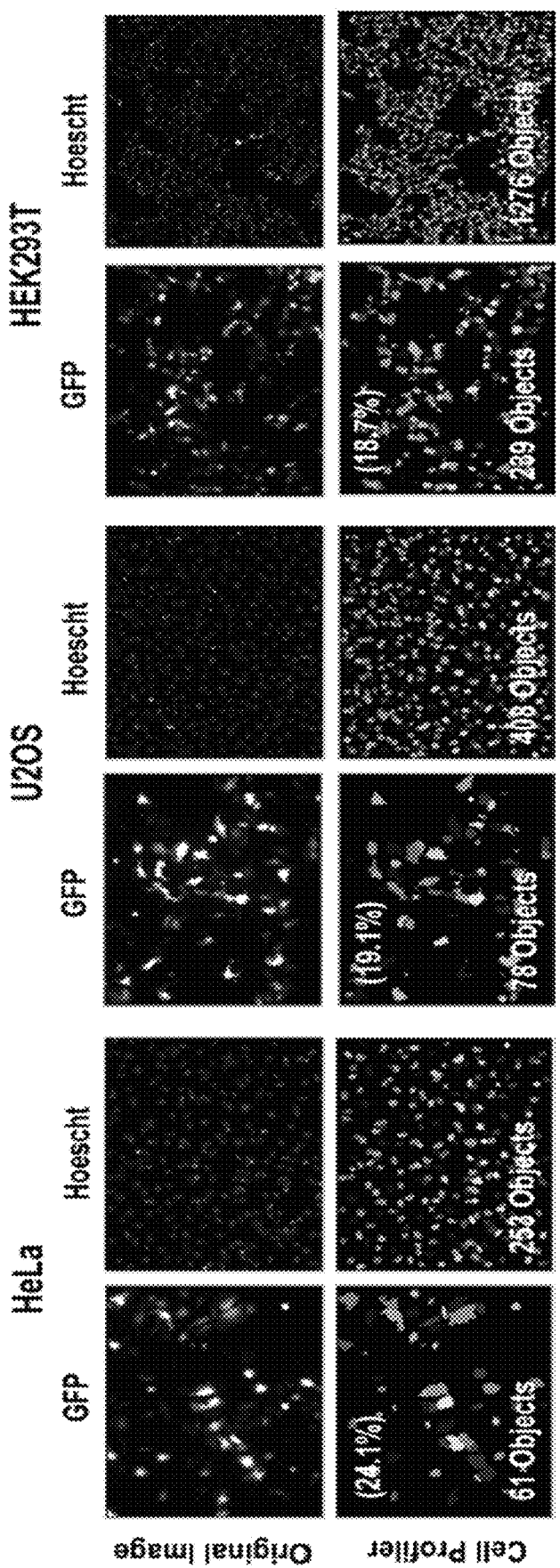
FIG. 31 depicts the results of experiments showing that transfection efficiency can be quantified using GIGI. HeLa, U2OS or HEK293T cells were transiently transfected with GIGI component plasmids. Following transfection, the cells were treated with 1 mM SDex for 24 h and imaged by epifluorescence microscopy. Raw images were processed using CellProfiler imaging software. Top row shows original images in greyscale of fluorescing cells (GFP channel) and nuclei stained with Hoechst 33342 (Hoechst channel). Bottom row shows 'object' images generated by CellProfiler software from the images from the top row. Hoechst images were acquired using the Zeiss Filter Set #49 (excitation G 365 nm, FT 395, emission BP 445/50) and GFP images were acquired using Zeiss Filter Set #44 (excitation BP 475/50 nm, FT 500, emission BP 530/50 nm) respectively. Transfection efficiencies (shown as percentages, Table 2) were calculated by dividing the number of objects counted in the GFP channel by the number of objects counted in the Hoechst channel.

*Values were determined from data shown in FIGS. 31 and 34.

GIGI Quantified by Live Cell Imaging

Figure 23D:
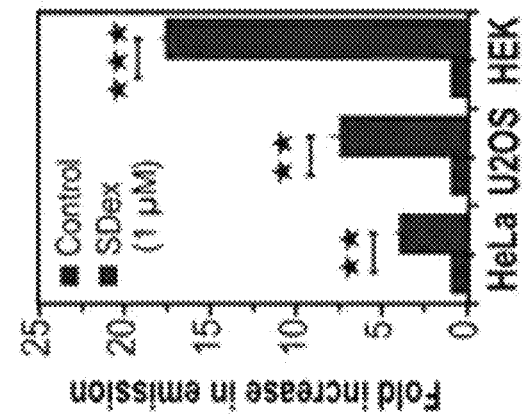
Figure 23C:
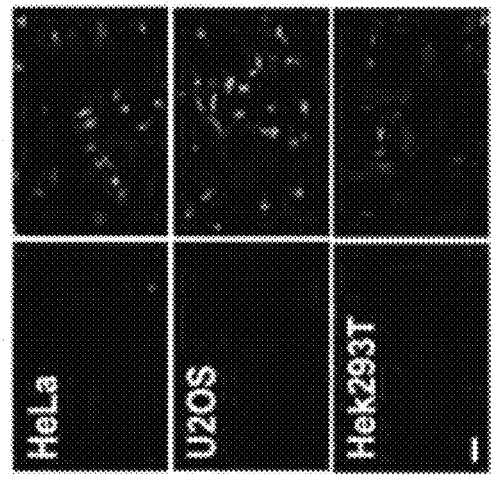
Figure 30:
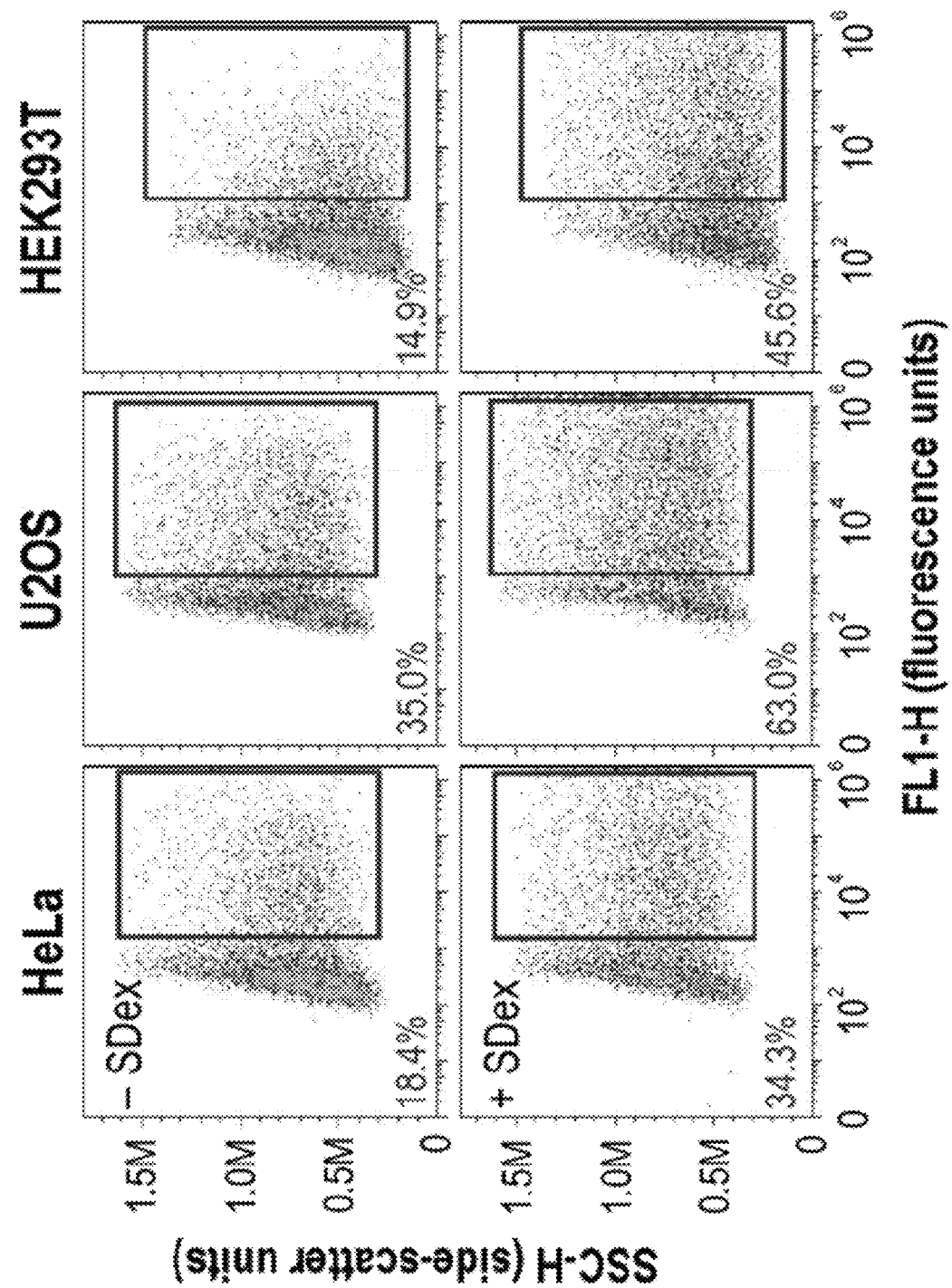
FIG. 30 depicts representative FACS scatter plots of treated (+SDex) and untreated (–SDex) cells. HeLa, U2OS or HEK293T cells transiently transfected with GIGI component plasmids as described. Following transfection, the cells were treated with 1 mM SDex for 24 h and subjected to FACS analysis as described. Gating (rectangles) shows that a higher percentage of cells fluoresce in the FL1-H channel when treated with SDex compared to untreated populations. Percentages were calculated by dividing the number of events within each gated region by the total number of events (20,000). Excitation and emission wavelengths for measuring eGFP fluorescence intensity were set at 488 nm and 533 nm respectively.

Next, it was assessed whether GIGI is useful to evaluate the cytosolic access of Dex-tagged molecules without the need for cell lysis, that is, in living cells. HeLa, U2OS, and HEK293T cells were each transiently transfected with pGal4-GR★-VP16, pG5-eGFP, and pmCherry-N1, treated with or without 1 µM SDex, and examined using epifluorescence microscopy or flow cytometry. All cell lines tested showed significant SDex-dependent increases in eGFP fluorescence, whether viewed by microscopy (FIG. 23C) or analyzed by flow cytometry (FIGS. 23D and 30). Using flow cytometry, the fold increase in eGFP expression was greatest in HEK293T cells (18-fold), followed by U2OS cells (8-fold), and then by HeLa cells (4-fold). This order is slightly different than that observed when eGFP expression was analyzed after cell lysis (see FIG. 23B). In both cases, HEK293T cells show the greatest increase in eGFP production in the presence of SDex, while the relative increases in eGFP expression in HeLa and U2OS cells differ, perhaps because of the higher inherent auto-fluorescence of HeLa cells53 or the larger cell size of U2OS cells. Control experiments verified that the observed difference in fold induction did not result from differences in transfection efficiency (FIG. 31 and Table 2).

Establishing a Stable GIGI Reporter System in U2OS Cells

Figure 24A:
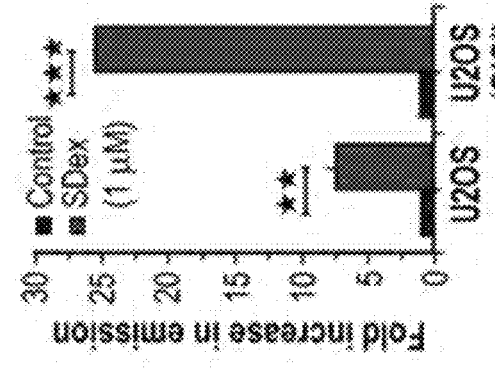
FIGS. 24A-24F, depicts the results of GIGI assays performed in stably transfected U2OS(GIGI) cells. In all cases, RFUs were calculated using Equation 1 (see Experimental Examples) and are expressed±standard deviation (Excel). Curves shown represent the best fit of the data to Equation 2 (see Experimental Examples). Statistical analysis was performed using a two-tailed Student's t test with each cell line treated as a separate population;  p≤0.005, * p≤0.001.
Figure 24B:
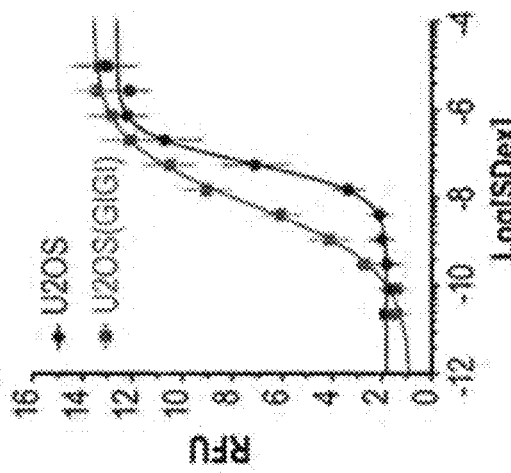
Figure 24C:
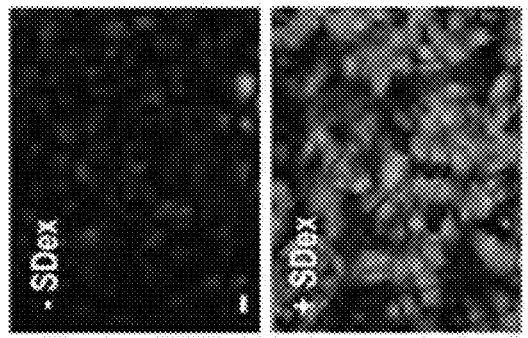

The working time frame of assays that utilize transiently transfected cells is limited, as transfected plasmids and expressed proteins can be rapidly degraded. Indeed, the GIGI assay was time-sensitive in transiently transfected HEK293T cells, with signal levels reduced to near background levels after 72 h (FIG. 32). It was hypothesized that a cell line stably transfected with GIGI components would eliminate this time dependence and facilitate the application of this system to high-throughput screening, which is most robust in stably transfected cells. To test this hypothesis, standard antibiotic resistance methods were first used to select for U2OS cells that were stably transfected with GIGI components derived from pG5-eGFP, pGal4-GR★-VP16, and pmCherry-N1 (FIG. 33) and dubbed this new cell line U2OS(GIGI). No difference in the viability or morphology of U2OS and U2OS(GIGI) cells were observed over several weeks of growth, suggesting that the cells can tolerate long-term expression of Gal4-GR★-VP16. To ensure that the GIGI assay would perform in U2OS(GIGI) cells, the cells were treated for 24 h with or without 1 µM SDex and the levels of eGFP produced was compared using epifluorescence microscopy (FIG. 24A). Addition of 1 µM SDex to U2OS(GIGI) cells led to significant eGFP expression in greater than 85% of cells examined, a value much greater than the 19% efficiency observed in transiently transfected U2OS cells (compare FIGS. 23C and 24A, and FIG. 34 and Table 2). Furthermore, examination of the relative fluorescence of the two cell populations treated with between $10^{-11}$ to $10^{-5}$ M SDex after lysis indicated a significant improvement in EC50 from 58 nM for the transiently transfected U2OS cells to 6 nM for U2OS(GIGI) cells (FIG. 24B and Table 2). Finally, FACS analysis of transiently transfected U2OS or U2OS(GIGI) cells treated with 1 µM SDex showed the stably transfected cells to be roughly 3-fold brighter than the transient transfectants (FIG. 24C). Taken together, these data indicate that U2OS(GIGI) cells represent a significant improvement in sensitivity and temporal control of the GIGI assay over transiently transfected U2OS cells.

Applying Methodology: Using GIGI to Evaluate Cytosolic Delivery

Next, U2OS(GIGI) cells were used to compare the relative cytosolic delivery of Dex-tagged versions of the canonical cell-penetrating peptides Tat[56-58] (SEQ ID NO:67) and octaarginine (Arg$_8$; SEQ ID NO:68)[59-61] as well as a series of previously examined minimally cationic pancreatic fold proteins (Table 3) (FIG. 24D) (Smith et al., 2008, J. Am. Chem. Soc. 130:2948-2949; Appelbaum et al., 2012, Chem. Biol. 19:819-830).

TABLE 3

Relative EC50 values for various Dex-labeled peptides as determined by GIGI in stably transfected U2OS(GIGI) cells.

| Peptide | $EC_{50}$ (nM) |
|---|---|
| aPP$^{Dex}$ | 438.3 |
| 4.3$^{Dex}$ | 482.1 |
| 5.2$^{Dex}$ | 703.2 |
| 5.3$^{Dex}$ | 52.9 |
| wtZF$^{Dex}$ | 102.7 |
| ZF5.3$^{Dex}$ | 1.4 |
| ZFN1$^{Dex}$ | 73.5 |
| ZPN2$^{Dex}$ | 76.7 |
| ZFN3$^{Dex}$ | 85.6 |
| ZFN4$^{Dex}$ | 71.3 |

Values are determined from data shown in FIGS. 23 and 26.

Examined after treatment and cell lysis, significant eGFP expression was observed in U2OS(GIGI) cells treated with 1 µM TatDex (SEQ ID NO:36), Arg8Dex (SEQ ID NO:37), 5.3Dex (SEQ ID NO:33), 5.2Dex (SEQ ID NO:32), and 4.3Dex (SEQ ID NO:31), with the highest levels produced in the presence of 5.3Dex (SEQ ID NO:33). The superiority of 5.3Dex (SEQ ID NO:33) was also observed using a previously reported translocation assay using GR-GFP34 (the predecessor of GIGT). Notably, two peptides that did not induce eGFP expression in transiently transfected HeLa cells, 5.2Dex (SEQ ID NO:32) and 4.3Dex (SEQ ID NO:31) (FIG. 35), led to significant expression across a wide concentration range in U2OS(GIGI) cells (FIG. 24E), highlighting the increased sensitivity in U2OS(GIGI) cells for evaluating the cytosolic delivery of Dex-labeled material. The EC50 for cells treated with 5.3Dex (SEQ ID NO:33) is 52.9 nM, a value approximately 10-fold lower than that of the next most potent peptide, 4.3Dex (SEQ ID NO:31) (EC50=482.1 nM). EC50 values for all peptides described herein are shown in Table 4.

TABLE 4

Relative EC50 and RFUmax max values for various cell lines as determined by GIGT.

| Cell Line | GR-GFP | | GR★-GFP | |
|---|---|---|---|---|
| | EC$_{50}$ (µM) | TR$_{max}$ | EC$_{50}$ (µM) | TR$_{max}$ |
| U2OS | 0.639 | 5.58 | 0.162 | 5.62 |
| Hela | 0.171 | 4.68 | 0.022 | 5.50 |
| Saos2(GIGT) | N/A | N/A | 0.262 | 5.11 |

EC50 values were determined from data shown in FIGS. 24B and 25B.

Figure 24D:
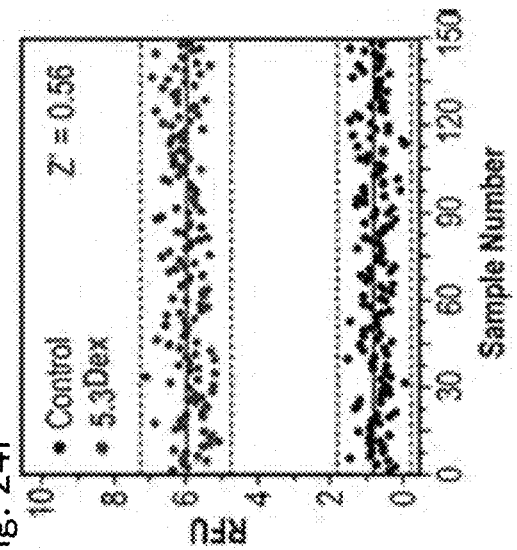
Figure 24E:
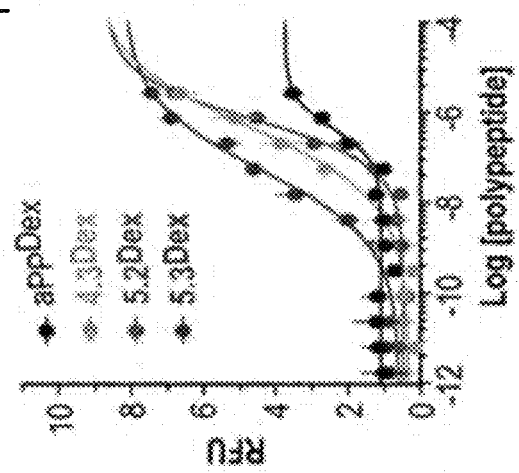
Figure 24F:
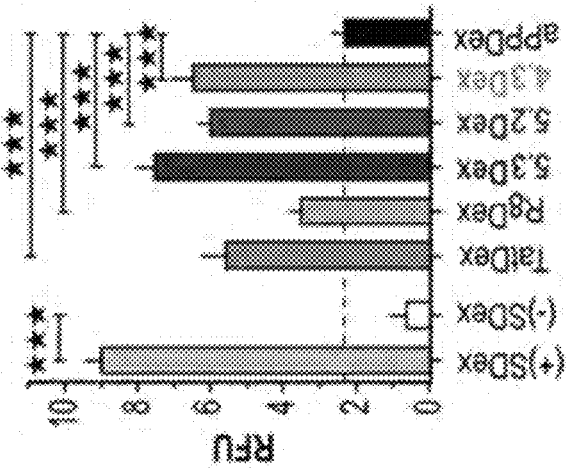

Finally, to test the well-to-well variability of an assay performed in U2OS(GIGI) cells, we treated a large sample population (n=150) with or without 1 µM 5.3Dex for 24 h and quantified eGFP expression from cell lysates (FIG. 24F). The Z'-factor is a statistical parameter that is used to quantify the suitability of an assay for use in high-throughput screening and provides a measure of the amount of separation between two sample populations (see Equation 3). A negative Z'-factor results from substantial overlap between positive and negative control samples, while the Z'-factor approaches 1 as separation increases toward infinity. The Z'-factor measured for the GIGI assay in the presence of 5.3Dex was 0.56 across 150 wells, a value that indicates that GIGI is robust enough to be used for high-throughput screening of cell populations treated with 5.3Dex.

Developing Methodology: GIGT Design and Rationale

While GIGI eliminates many disadvantages of the assay reported by Yu et al., it is still limited by the time delay between the entry of Dex-tagged molecules into the cytosol and eGFP expression. Previously, an assay was used that minimized this delay by monitoring the nuclear translocation of a GR-GFP fusion protein, as opposed to its expression, and applied this assay to evaluate the relative cytosolic levels of Dex-tagged peptides and proteins (Appelbaum et al., 2012, Chem. Biol. 19:819-830). It was hypothesized that the sensitivity of this nuclear translocation assay would also be improved by introduction of the C to G mutation within the GR ligand-binding domain, generating GR★-GFP. To test this hypothesis, either GR-GFP or GR★-GFP was expressed in HeLa and U2OS cells, and the nuclear translocation of each construct in the presence and absence of 100 nM SDex (FIG. 25A) was monitored by epifluorescence microscopy. Nuclear translocation was quantified by measuring the ratio of the mean GFP signal in the nucleus to the mean signal within the surrounding cytosol using CellProfiler. In both cell lines, replacing GR-GFP with GR★-GFP led to a significant decrease in the SDex concentration required to achieve the half maximal translocation ratio (TR). This concentration decreased from 171 nM to 22 nM in HeLa cells and from 639 nM to 162 nM in U2OS cells, representing 8- and 4-fold improvements in sensitivity, respectively (FIG. 25B and Table 5).

TABLE 5

Mass spectral characterization of Dex-labeled miniature proteins

| Peptide | Sequence | SEQ ID NO: | Calc (+m/z) | Obs (+m/z) |
|---|---|---|---|---|
| aPP$^{Dex}$ | K$^{Dex}$GPSQPTYPGDDAPVEDLIRFYNDLQQYLNVVTRHRY | 29 | 4826.37 | 4826.18 |
| 4.2$^{Dex}$ | K$^{Dex}$GPSQPTYPGDDAPVRDLIRFYRDLQRYLNVVTRHRY | 30 | 4923.53 | 4923.40 |
| 4.3$^{Dex}$ | K$^{Dex}$GPSQPTYPGDDAPVEDLIRFYRDLRRYLNVVTRHRY | 31 | 4924.51 | 4924.28 |
| 5.2$^{Dex}$ | K$^{Dex}$GPSQPTYPGDDAPVRDLIRFYRDLQRYLRVVTRHRY | 32 | 4965.58 | 4965.42 |
| 5.3$^{Dex}$ | K$^{Dex}$GPSQPTYPGDDAPVRDLIRFYRDLRRYLNVVTRHRY | 33 | 4951.57 | 4951.41 |
| 5.2-P2$^{Dex}$ | K$^{Dex}$GPSQPTYPGDDAPVRDLIRPYRDLQRPLRVVTRHRY | 52 | 4849.56 | 4849.46 |
| 5.3-P2$^{Dex}$ | K$^{Dex}$GPSQPTYPGDDAPVRDLIRPYRDLRRPLNVVTRHRY | 53 | 4835.54 | 4835.16 |
| wtZF$^{Dex}$ | K$^{Dex}$WYSCNVCGKAFVLSAHLNQHLAVHTQAT | 34 | 3687.80 | 3685.66 |
| ZF5.3$^{Dex}$ | K$^{Dex}$WYSCNVCGKAFVLSRHLNRHLRVHRRAT | 35 | 3969.07 | 3968.11 |
| ZFN1$^{Dex}$ | K$^{Dex}$FQCRICMRNFSDRSNLSRHIRTHTP | 54 | 3664.80 | 3664.65 |
| ZFN2$^{Dex}$ | K$^{Dex}$FACDICGRKFAISSNLNSHTKIHTP | 55 | 3349.66 | 3349.55 |
| ZFN3$^{Dex}$ | K$^{Dex}$FQCRICMRNFSRSDNLARHIRTHTP | 56 | 3648.80 | 3648.65 |
| ZFN4$^{Dex}$ | K$^{Dex}$FACDICGRKFATSGNLTRHTKIHLR | 57 | 3706.89 | 3706.78 |
| Tat$^{Dex}$ | K$^{Dex}$GRKKRRQRRRPPQY$_{-NH2}$ | 36 | 2471.42 | 2471.37 |
| Arg8$^{Dex}$ | K$^{Dex}$RRRRRRRR$_{-NH2}$ | 37 | 1857.12 | 1857.07 |

Finally, cells expressing GR★-GFP were exposed to a series of Dex-tagged miniature proteins (Appelbaum et al., 2012, Chem. Biol. 19:819-830) as well as TatDex (SEQ ID NO:36) and Arg8Dex (SEQ ID NO:37), (Mitchell et al., 2000, J. Peptide Res. 56:318-325) which have been evaluated previously on the basis of GR-GFP translocation (Appelbaum et al., 2012, Chem. Biol. 19:819-830) (FIG. 24C and 24D). At 500 nM, which is one-half the ligand concentration previously tested (Appelbaum et al., 2012, Chem. Biol. 19:819-830) the TRs measured in HeLa cells expressing GR★-GFP are similar to the those observed in HeLa cells expressing GR-GFP. In both cases among the miniature proteins, the highest TR values (2.79) were observed for cells treated with 5.3Dex (SEQ ID NO:33). Structural variants of 5.3Dex (SEQ ID NO:33) and 5.2Dex (SEQ ID NO:32) containing proline substitutions at two positions within the α-helix (at positions F24 and Y31) (Luedtke et al., 2007, Nat. Chem. Biol. 3, 779-784) were also examined using GIGT. Treatment of cells expressing GR★-GFP with 5.3-P2Dex led to a significant decrease in TR when compared to that of its structured counterpart, from 2.79±0.39 to 1.64±0.27, as did treatment with 5.2-P2Dex (from 1.86±0.36 to 1.35±0.11) (FIGS. 24C and 24D). These changes provide additional evidence that efficient cytosolic entry of cationic miniature proteins requires a precise α-helical display of arginine residues.

Establishing a Stable GIGT Reporter System in Saos2 Cells

Figure 26B:
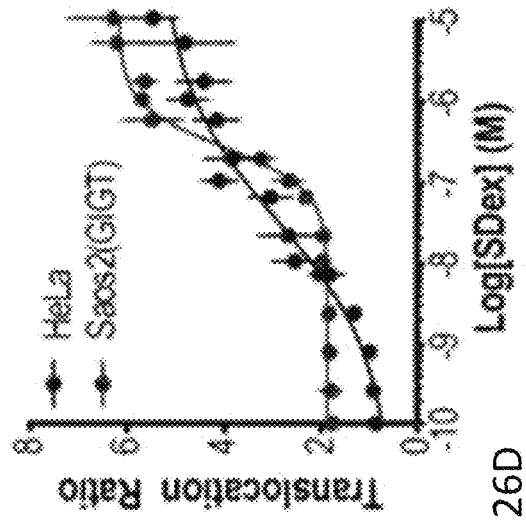
FIGS. 26A-26D, depicts the results of experiments performed for GIGT validation in stably transfected Saos-2(GIGT) cells.
Figure 26D:
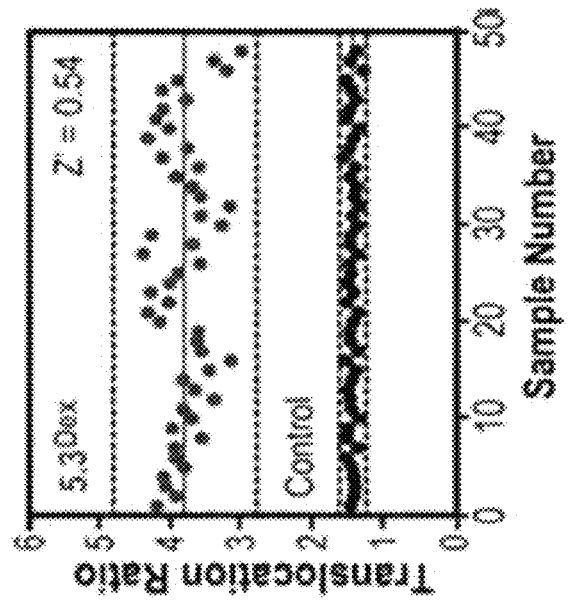
Figure 26A:
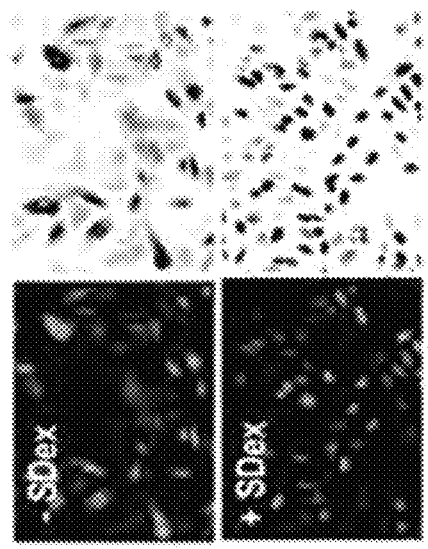
Figure 26C:
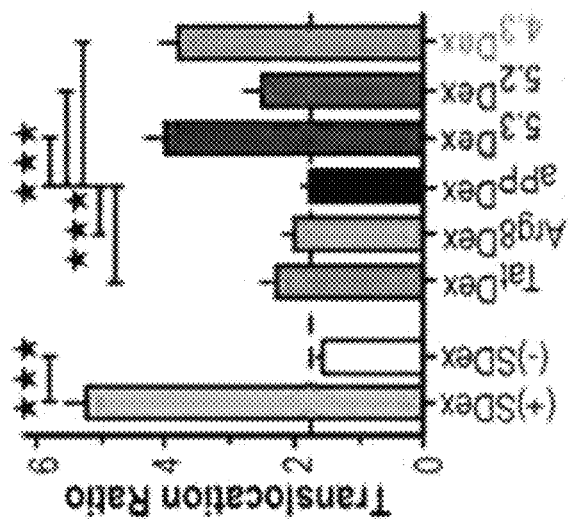

It was hypothesized that a cell line stably transfected with GR★-GFP would allow the GIGT assay to be bridged with high-content imaging. Human osteosarcoma Saos-2 cells (ATCC, HTB-85) were chosen because their amenability to stable genetic modulation makes them ideal for constructing cell-based reporter systems. Antibiotic selection followed by cell sorting was used to select for Saos-2 cells stably transfected with GR★-GFP and this new cell line was dubbed Soas-2(GIGT). To ensure that the GIGT assay could be performed in Saos-2(GIGT) cells, cells were treated for 30 min with or without 1 µM SDex and translocation ratios (TR) were quantified using an Opera high-content imaging system and Acapella High Content Imaging and Analysis software (Perkin-Elmer). In the absence of SDex, GR★-GFP distributes nearly uniformly throughout the cytosol and nucleus (FIG. 26A), resulting in an average TR of 1.48±0.06. In the presence of 1 µM SDex, GR★-GFP translocates almost exclusively to the nucleus, with a resultant ratio of 5.11±0.34. The TR calculated for Saos-2(GIGT) cells treated with 1 µM SDex (5.68±0.13) are higher and less variable than those for equivalently treated, transiently transfected HeLa cells (4.74±0.42) (FIG. 26B). This improvement in signal and reduction in variability supports the use of Saos-2(GIGT) cells over transiently transfected HeLa cells for high-content GIGT analysis. Next, Saos-2 (GIGT) cells were used to compare the relative cytosolic delivery of Dex-tagged peptides such as Tat (SEQ ID NO:67) and Arg8 (SEQ ID NO:68) and a panel of previously examined, minimally cationic polypeptides (see Appelbaum et al., 2012, Chem. Biol. 19:819-830) (FIG. 26C). Significant GR★-GFP nuclear translocation was observed when Saos-2(GIGT) cells were treated with 1 µM 5.3Dex (SEQ ID NO:33), 4.3Dex (SEQ ID NO:31), and 5.2Dex (SEQ ID NO:32), with the highest TRs observed in the presence of 5.3Dex (SEQ ID NO:33). In contrast to GIGT performance in transiently transfected HeLa cells, where significant TRs were measured only for 5.3Dex (SEQ ID NO:33, FIG. 25C), in Saos-2(GIGT) cells significant TRs were measured for both 5.3Dex (SEQ ID NO:33, 4.01±0.30) and 4.3Dex (SEQ ID NO:31, 3.79±0.29). Low TRs are observed for both TatDex (SEQ ID NO:36, 2.28±0.24) and Arg8Dex (SEQ ID NO:37, 2.00±0.16). The discrepancies in miniature protein TR values may result from the differential modes of endocytic uptake between the two cell lines, as the endocytic regulatory network is cell-type dependent (Doherty and McMahon, 2009, Annu. Rev. Biochem. 78:857-902; Mercer and Helenius, 2009, Nat. Cell Biol. 11:510-520). Finally, to identify the applicability of Saos-2(GIGT) cells to high-throughput microscopy, the Z'-factor was calculated across 50 experimental populations of over 200 cells. The Z'-factor between Saos-2(GIGT) cells treated in the presence and absence of 1 µM 5.3Dex (SEQ ID NO:33) was 0.54 (FIG. 26D), which indicates that GIGT is a robust platform for high-throughput screening of Dex-peptide conjugates.

Evaluating Cytosolic Delivery of Zinc-Finger Domains

Zinc-finger nucleases (ZFNs) are fusion proteins composed of restriction endonucleases and Cys2-His2 zinc-finger domains that have displayed potential as agents for targeted gene therapy. The modular zinc-finger components can be customized to target specific gene sequences, enabling ZFNs to induce site-specific double-strand DNA breaks that knock out gene function upon non-homologous recombination. There is little doubt that the utility of ZFNs would be enhanced if they could be delivered directly into the interior of living cells without the use of retroviral insertion. Although attempts to enhance ZFN uptake by appending highly cationic peptide sequences, such as Tat (SEQ ID NO:67) or Arg8 (SEQ ID NO:68), have met with only modest success (Gaj et al., 2012, Nat. Methods 9:805-807), it has been reported that certain ZFNs reach the cell interior without further modification, perhaps because their DNA binding domains carry a net positive charge. Notably, the assay used to detect the ZFN in this case is exceedingly sensitive, requiring in the limiting case only a single ZFN-catalyzed non-homologous recombination event to generate a positive signal. Both GIGI and GIGT were used to compare the relative cytosolic localization of an unmodified zinc-finger domain (wtZF) to that of ZF5.3 and the four ZFNs reported recently to enter the interior of mammalian cells, ZFN1, ZFN2, ZFN3, and ZFN-4 (Gaj et al., 2012, Nat. Methods 9:805-807). Variants of ZFN1-4 carrying a C-terminal Dex tag were prepared by solid phase synthesis (see Gaj et al., 2012, Nat. Methods 9:805-807) (FIGS. 27A and 27B). All zinc-finger domains showed evidence of α-helical structure at a concentration of 25 µM (10 mM, Tris at pH 7.4) in the presence of 50 µM ZnC12 when measured by circular dichroism spectroscopy; wtZF, ZF5.3, ZFN4, and ZFN2 showed the highest levels of helical structure (FIG. 36). GIGI (FIG. 27C) and GIGT (FIG. 27D) were used to compare the cytosolic localization of all six zinc finger domains in stably transfected U2OS(GIGI) and Saos2 (GIGT) cells. ZF5.3Dex induced significantly higher levels of eGFP expression (GIGI) and GR★-GFP translocation (GIGT) than wtZF and all four ZFN domains tested. When analyzed after cell lysis, ZF5.3Dex induced eGFP expression in U2OS(GIGI) cells with an EC50 a full 100-fold lower than that of wtZFDex (1.4 nM vs 102.7 nM) (FIG. 27C and Table 4) and 70-80-fold lower than that of ZF domains ZFN1-4Dex. Similar trends are observed when cytosolic entry was evaluated using GIGT (FIG. 27D). Significant differences were also observed when the ZF domains were compared across cell populations: the most active ZFN reported induced eGFP expression in only 12% of the cells treated, whereas ZF5.3Dex led to significant translocation ratios in greater than 99% of cells expressing GR★-GFP. These results indicate that the penta-Arg containing ZF5.3 traffics to the cytosol more efficiently than ZF domains that lack a penta-Arg motif and that introduction of a penta-Arg motif significantly improves the cytosolic delivery of zinc finger nuclease domains. To test the robustness of GIGI and GIGT assays for analyzing the relative trafficking of zinc-finger proteins, the Z'-factor was measured between U2OS(GIGI) and Saos-2(GIGT) cells treated in the presence and absence of 1 µM ZF5.3Dex (FIG. 27E and 27F). Notably, the Z'-factor was determined to be 0.42 for the GIGI assay and 0.56 for the GIGT assay, which indicates that both GIGI and GIGT are robust enough to be used for high-throughput screening of cell populations treated with ZF5.3Dex.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising a nucleic acid molecule encoding a modified protein comprising an amino acid sequence selected from the group consisting of SEQ ID NOS: 10, 19, 25, 33, 35, 39, 41 and 70.

2. The composition of claim 1 wherein the modified protein is a modified protein fusion molecule comprising a modified protein domain (MPD) and a cargo domain, wherein the MPD comprises an amino acid sequence selected from the group consisting of SEQ ID NOS: 10, 19, 25, 33, 35, 39, 41 and 70.

3. The composition of claim 2, wherein the modified protein fusion molecule further comprises a linker.

4. The composition of claim 2, wherein the modified protein fusion molecule further comprises a label.

5. A method of treating a disease or disorder in a subject in need thereof, the method comprising administering to the subject a therapeutically effective amount of the composition of claim 1.

6. The method of claim 5, wherein the subject is human.

7. A method of transporting a cargo molecule to the cytosol or nucleus of a cell, the method comprising contacting a cell with a modified protein, wherein the modified protein comprises an amino acid sequence selected from the group consisting of SEQ ID NOS: 10, 19, 25, 33, 35, 39, 41 and 70.

8. The method of claim 7, wherein the modified protein is a fusion molecule comprising a modified protein domain (MPD) and a cargo domain, wherein the MPD comprises an amino acid sequence selected from the group consisting of SEQ ID NOS: 10, 19, 25, 33, 35, 39, 41 and 70.

9. The method of claim 8, wherein the cargo domain comprises at least one selected from the group consisting of a small molecule, a nucleic acid and a polypeptide.

10. A composition comprising a nucleic acid molecule encoding a modified protein comprising the amino acid sequence of SEQ ID NO:53.

11. The composition of claim 10 wherein the modified protein is a modified protein fusion molecule comprising a modified protein domain (MPD) and a cargo domain, wherein the MPD comprises an amino acid of SEQ ID NO:53.

12. The composition of claim 11, wherein the modified protein fusion molecule further comprises a linker.

13. The composition of claim 11, wherein the modified protein fusion molecule further comprises a label.

14. A method of treating a disease or disorder in a subject in need thereof, the method comprising administering to the subject a therapeutically effective amount of the composition of claim 10.

15. The method of claim 14, wherein the subject is human.

16. A method of transporting a cargo molecule to the cytosol or nucleus of a cell, the method comprising contacting a cell with a modified protein, wherein the modified protein comprises an amino acid sequence of SEQ ID NO: 53.

17. The method of claim 16, wherein the modified protein is a fusion molecule comprising a modified protein domain (MPD) and a cargo domain, wherein the MPD comprises an amino acid sequence of SEQ ID NO: 53.

18. The method of claim 17, wherein the cargo domain comprises at least one selected from the group consisting of a small molecule, a nucleic acid and a polypeptide.

19. The method of claim 16, wherein the cargo molecule is not covalently bound to the modified protein.

* * * * *

```
                        SEQUENCE LISTING

<160> NUMBER OF SEQ ID NOS: 74

<210> SEQ ID NO 1
<211> LENGTH: 81
<212> TYPE: DNA
<213> ORGANISM: Artificial Sequence
<220> FEATURE:
<223> OTHER INFORMATION: synthesized

<400> SEQUENCE: 1
ccggactcag atctcgagct caagcttcga attcgccatg gactccaaag aatcattaac      60
tcctggtaga gaagaaaacc c                                                81

<210> SEQ ID NO 2
<211> LENGTH: 74
<212> TYPE: DNA
<213> ORGANISM: Artificial Sequence
<220> FEATURE:
<223> OTHER INFORMATION: synthesized

<400> SEQUENCE: 2
gcgcggatcc cgcggctttt gatgaaacag aagtttttg atatttccat ttgaatattt       60
tggtatctga ttgg                                                        74

<210> SEQ ID NO 3
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (37)..(37)
<223> OTHER INFORMATION: acetyl-NH2

<400> SEQUENCE: 3

Gly Pro Ser Gln Pro Thr Tyr Pro Gly Asp Asp Ala Pro Val Glu Asp
1               5                   10                  15

Leu Ile Arg Phe Tyr Asn Asp Leu Gln Gln Tyr Leu Asn Val Val Thr
            20                  25                  30

Arg His Arg Tyr Cys
        35

<210> SEQ ID NO 4
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (37)..(37)
<223> OTHER INFORMATION: acetyl-NH2

<400> SEQUENCE: 4

Gly Pro Ser Gln Pro Thr Tyr Pro Gly Asp Asp Ala Pro Val Glu Asp
1               5                   10                  15

Leu Ile Arg Phe Tyr Asn Asp Leu Gln Arg Tyr Leu Asn Val Val Thr
            20                  25                  30
```

Arg His Arg Tyr Cys
        35

<210> SEQ ID NO 5
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (37)..(37)
<223> OTHER INFORMATION: acetyl-NH2

<400> SEQUENCE: 5

Gly Pro Ser Gln Pro Thr Tyr Pro Gly Asp Asp Ala Pro Val Glu Asp
1               5                   10                  15

Leu Ile Arg Phe Tyr Arg Asp Leu Gln Gln Tyr Leu Asn Val Val Thr
            20                  25                  30

Arg His Arg Tyr Cys
        35

<210> SEQ ID NO 6
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (37)..(37)
<223> OTHER INFORMATION: acetyl-NH2

<400> SEQUENCE: 6

Gly Pro Ser Gln Pro Thr Tyr Pro Gly Asp Asp Ala Pro Val Glu Asp
1               5                   10                  15

Leu Ile Arg Phe Tyr Arg Asp Leu Gln Arg Tyr Leu Asn Val Val Thr
            20                  25                  30

Arg His Arg Tyr Cys
        35

<210> SEQ ID NO 7
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (37)..(37)
<223> OTHER INFORMATION: acetyl-NH2

<400> SEQUENCE: 7

Gly Pro Ser Gln Pro Thr Tyr Pro Gly Asp Asp Ala Pro Val Arg Asp
1               5                   10                  15

Leu Ile Arg Phe Tyr Arg Asp Leu Gln Arg Tyr Leu Asn Val Val Thr
            20                  25                  30

Arg His Arg Tyr Cys
        35

<210> SEQ ID NO 8
<211> LENGTH: 37
<212> TYPE: PRT
<213> ORGANISM: Artificial Sequence
<220> FEATURE:

<223> OTHER INFORMATION: synthesized
<220> FEATURE:
<221> NAME/KEY: MISC_FEATURE
<222> LOCATION: (37)..(37)
<223> OTHER INFORMATION: acetyl-NH2

<400> SEQUENCE: 8

Gly Pro Ser Gln Pro Thr Tyr Pro Gly Asp Asp Ala Pro Val Glu Asp
1               5                   10                  15

Leu Ile Arg Phe Tyr Arg Asp Leu Arg Arg Tyr Leu Asn Val Val Thr
            20                  25                  30

Arg His Arg Tyr Cys
        35

<210> SEQ ID NO 9
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (37)..(37)
<223> OTHER INFORMATION: acetyl-NH2

<400> SEQUENCE: 9

Gly Pro Ser Gln Pro Thr Tyr Pro Gly Asp Asp Ala Pro Val Arg Asp
1               5                   10                  15

Leu Ile Arg Phe Tyr Arg Asp Leu Gln Arg Tyr Leu Arg Val Val Thr
            20                  25                  30

Arg His Arg Tyr Cys
        35

<210> SEQ ID NO 10
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (37)..(37)
<223> OTHER INFORMATION: acetyl-NH2

<400> SEQUENCE: 10

Gly Pro Ser Gln Pro Thr Tyr Pro Gly Asp Asp Ala Pro Val Arg Asp
1               5                   10                  15

Leu Ile Arg Phe Tyr Arg Asp Leu Arg Arg Tyr Leu Asn Val Val Thr
            20                  25                  30

Arg His Arg Tyr Cys
        35

<210> SEQ ID NO 11
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (37)..(37)
<223> OTHER INFORMATION: acetyl-NH2

<400> SEQUENCE: 11

Gly Pro Ser Gln Pro Thr Tyr Pro Gly Asp Asp Ala Pro Val Arg Asp
1               5                   10                  15

Leu Arg Arg Phe Tyr Arg Asp Leu Arg Arg Tyr Leu Asn Val Val Thr
            20                  25                  30

Arg His Arg Tyr Cys
        35

<210> SEQ ID NO 12
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (37)..(37)
<223> OTHER INFORMATION: fluorescein

<400> SEQUENCE: 12

Gly Pro Ser Gln Pro Thr Tyr Pro Gly Asp Asp Ala Pro Val Glu Asp
1               5                   10                  15

Leu Ile Arg Phe Tyr Asn Asp Leu Gln Gln Tyr Leu Asn Val Val Thr
            20                  25                  30

Arg His Arg Tyr Cys
        35

<210> SEQ ID NO 13
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (37)..(37)
<223> OTHER INFORMATION: fluorescein

<400> SEQUENCE: 13

Gly Pro Ser Gln Pro Thr Tyr Pro Gly Asp Asp Ala Pro Val Glu Asp
1               5                   10                  15

Leu Ile Arg Phe Tyr Asn Asp Leu Gln Arg Tyr Leu Asn Val Val Thr
            20                  25                  30

Arg His Arg Tyr Cys
        35

<210> SEQ ID NO 14
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (37)..(37)
<223> OTHER INFORMATION: fluorescein

<400> SEQUENCE: 14

Gly Pro Ser Gln Pro Thr Tyr Pro Gly Asp Asp Ala Pro Val Glu Asp
1               5                   10                  15

Leu Ile Arg Phe Tyr Arg Asp Leu Gln Gln Tyr Leu Asn Val Val Thr
            20                  25                  30

Arg His Arg Tyr Cys
        35

<210> SEQ ID NO 15
<211> LENGTH: 37

```
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (37)..(37)
<223> OTHER INFORMATION: fluorescein

<400> SEQUENCE: 15
```

Gly Pro Ser Gln Pro Thr Tyr Pro Gly Asp Asp Ala Pro Val Glu Asp
1               5                   10                  15

Leu Ile Arg Phe Tyr Arg Asp Leu Gln Arg Tyr Leu Asn Val Val Thr
            20                  25                  30

Arg His Arg Tyr Cys
        35

```
<210> SEQ ID NO 16
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (37)..(37)
<223> OTHER INFORMATION: fluorescein

<400> SEQUENCE: 16
```

Gly Pro Ser Gln Pro Thr Tyr Pro Gly Asp Asp Ala Pro Val Arg Asp
1               5                   10                  15

Leu Ile Arg Phe Tyr Arg Asp Leu Gln Arg Tyr Leu Asn Val Val Thr
            20                  25                  30

Arg His Arg Tyr Cys
        35

```
<210> SEQ ID NO 17
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (37)..(37)
<223> OTHER INFORMATION: fluorescein

<400> SEQUENCE: 17
```

Gly Pro Ser Gln Pro Thr Tyr Pro Gly Asp Asp Ala Pro Val Glu Asp
1               5                   10                  15

Leu Ile Arg Phe Tyr Arg Asp Leu Arg Arg Tyr Leu Asn Val Val Thr
            20                  25                  30

Arg His Arg Tyr Cys
        35

```
<210> SEQ ID NO 18
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (37)..(37)
<223> OTHER INFORMATION: fluorescein

<400> SEQUENCE: 18
```

Gly Pro Ser Gln Pro Thr Tyr Pro Gly Asp Asp Ala Pro Val Arg Asp
1               5                   10                  15

Leu Ile Arg Phe Tyr Arg Asp Leu Gln Arg Tyr Leu Arg Val Val Thr
            20                  25                  30

Arg His Arg Tyr Cys
            35

<210> SEQ ID NO 19
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (37)..(37)
<223> OTHER INFORMATION: fluorescein

<400> SEQUENCE: 19

Gly Pro Ser Gln Pro Thr Tyr Pro Gly Asp Asp Ala Pro Val Arg Asp
1               5                   10                  15

Leu Ile Arg Phe Tyr Arg Asp Leu Arg Arg Tyr Leu Asn Val Val Thr
            20                  25                  30

Arg His Arg Tyr Cys
            35

<210> SEQ ID NO 20
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (37)..(37)
<223> OTHER INFORMATION: fluorescein

<400> SEQUENCE: 20

Gly Pro Ser Gln Pro Thr Tyr Pro Gly Asp Asp Ala Pro Val Arg Asp
1               5                   10                  15

Leu Arg Arg Phe Tyr Arg Asp Leu Arg Arg Tyr Leu Asn Val Val Thr
            20                  25                  30

Arg His Arg Tyr Cys
            35

<210> SEQ ID NO 21
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: rhodamine

<400> SEQUENCE: 21

Lys Gly Pro Ser Gln Pro Thr Tyr Pro Gly Asp Asp Ala Pro Val Glu
1               5                   10                  15

Asp Leu Ile Arg Phe Tyr Asn Asp Leu Gln Gln Tyr Leu Asn Val Val
            20                  25                  30

Thr Arg His Arg Tyr
            35

```
<210> SEQ ID NO 22
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: rhodamine

<400> SEQUENCE: 22

Lys Gly Pro Ser Gln Pro Thr Tyr Pro Gly Asp Asp Ala Pro Val Arg
1               5                   10                  15

Asp Leu Ile Arg Phe Tyr Arg Asp Leu Gln Arg Tyr Leu Asn Val Val
            20                  25                  30

Thr Arg His Arg Tyr
        35

<210> SEQ ID NO 23
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: rhodamine

<400> SEQUENCE: 23

Lys Gly Pro Ser Gln Pro Thr Tyr Pro Gly Asp Asp Ala Pro Val Glu
1               5                   10                  15

Asp Leu Ile Arg Phe Tyr Arg Asp Leu Arg Arg Tyr Leu Asn Val Val
            20                  25                  30

Thr Arg His Arg Tyr
        35

<210> SEQ ID NO 24
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: rhodamine

<400> SEQUENCE: 24

Lys Gly Pro Ser Gln Pro Thr Tyr Pro Gly Asp Asp Ala Pro Val Arg
1               5                   10                  15

Asp Leu Ile Arg Phe Tyr Arg Asp Leu Gln Arg Tyr Leu Arg Val Val
            20                  25                  30

Thr Arg His Arg Tyr
        35

<210> SEQ ID NO 25
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (1)..(1)
```

<223> OTHER INFORMATION: rhodamine

<400> SEQUENCE: 25

Lys Gly Pro Ser Gln Pro Thr Tyr Pro Gly Asp Asp Ala Pro Val Arg
1               5                   10                  15

Asp Leu Ile Arg Phe Tyr Arg Asp Leu Arg Arg Tyr Leu Asn Val Val
            20                  25                  30

Thr Arg His Arg Tyr
        35

<210> SEQ ID NO 26
<211> LENGTH: 29
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: rhodamine

<400> SEQUENCE: 26

Lys Trp Tyr Ser Cys Asn Val Cys Gly Lys Ala Phe Val Leu Ser Arg
1               5                   10                  15

His Leu Asn Arg His Leu Arg Val His Arg Arg Ala Thr
            20                  25

<210> SEQ ID NO 27
<211> LENGTH: 15
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: rhodamine

<400> SEQUENCE: 27

Lys Gly Arg Lys Lys Arg Arg Gln Arg Arg Pro Pro Gln Tyr
1               5                   10                  15

<210> SEQ ID NO 28
<211> LENGTH: 9
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: rhodamine

<400> SEQUENCE: 28

Lys Arg Arg Arg Arg Arg Arg Arg
1               5

<210> SEQ ID NO 29
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: dexamethasone -continued

```
<400> SEQUENCE: 29

Lys Gly Pro Ser Gln Pro Thr Tyr Pro Gly Asp Asp Ala Pro Val Glu
1               5                   10                  15

Asp Leu Ile Arg Phe Tyr Asn Asp Leu Gln Gln Tyr Leu Asn Val Val
            20                  25                  30

Thr Arg His Arg Tyr
            35

<210> SEQ ID NO 30
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: dexamethasone

<400> SEQUENCE: 30

Lys Gly Pro Ser Gln Pro Thr Tyr Pro Gly Asp Asp Ala Pro Val Arg
1               5                   10                  15

Asp Leu Ile Arg Phe Tyr Arg Asp Leu Gln Arg Tyr Leu Asn Val Val
            20                  25                  30

Thr Arg His Arg Tyr
            35

<210> SEQ ID NO 31
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: dexamethasone

<400> SEQUENCE: 31

Lys Gly Pro Ser Gln Pro Thr Tyr Pro Gly Asp Asp Ala Pro Val Glu
1               5                   10                  15

Asp Leu Ile Arg Phe Tyr Arg Asp Leu Arg Arg Tyr Leu Asn Val Val
            20                  25                  30

Thr Arg His Arg Tyr
            35

<210> SEQ ID NO 32
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: dexamethasone

<400> SEQUENCE: 32

Lys Gly Pro Ser Gln Pro Thr Tyr Pro Gly Asp Asp Ala Pro Val Arg
1               5                   10                  15

Asp Leu Ile Arg Phe Tyr Arg Asp Leu Gln Arg Tyr Leu Arg Val Val
            20                  25                  30

Thr Arg His Arg Tyr
            35
```

```
<210> SEQ ID NO 33
<211> LENGTH: 37
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: dexamethasone

<400> SEQUENCE: 33

Lys Gly Pro Ser Gln Pro Thr Tyr Pro Gly Asp Asp Ala Pro Val Arg
1               5                   10                  15

Asp Leu Ile Arg Phe Tyr Arg Asp Leu Arg Arg Tyr Leu Asn Val Val
            20                  25                  30

Thr Arg His Arg Tyr
        35

<210> SEQ ID NO 34
<211> LENGTH: 29
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: dexamethasone

<400> SEQUENCE: 34

Lys Trp Tyr Ser Cys Asn Val Cys Gly Lys Ala Phe Val Leu Ser Ala
1               5                   10                  15

His Leu Asn Gln His Leu Ala Val His Thr Gln Ala Thr
            20                  25

<210> SEQ ID NO 35
<211> LENGTH: 29
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: dexamethasone

<400> SEQUENCE: 35

Lys Trp Tyr Ser Cys Asn Val Cys Gly Lys Ala Phe Val Leu Ser Arg
1               5                   10                  15

His Leu Asn Arg His Leu Arg Val His Arg Arg Ala Thr
            20                  25

<210> SEQ ID NO 36
<211> LENGTH: 15
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: dexamethasone

<400> SEQUENCE: 36

Lys Gly Arg Lys Lys Arg Arg Gln Arg Arg Arg Pro Pro Gln Tyr
```

```
<210> SEQ ID NO 37
<211> LENGTH: 9
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: dexamethasone

<400> SEQUENCE: 37

Lys Arg Arg Arg Arg Arg Arg Arg Arg
1               5

<210> SEQ ID NO 38
<211> LENGTH: 14
<212> TYPE: PRT
<213> ORGANISM: Artificial Sequence
<220> FEATURE:
<223> OTHER INFORMATION: synthesized

<400> SEQUENCE: 38

Leu Ser Gln Glu Thr Phe Asp Leu Trp Lys Leu Leu Glu Asn
1               5                   10

<210> SEQ ID NO 39
<211> LENGTH: 14
<212> TYPE: PRT
<213> ORGANISM: Artificial Sequence
<220> FEATURE:
<223> OTHER INFORMATION: synthesized

<400> SEQUENCE: 39

Arg Ser Gln Glu Arg Phe Arg Leu Trp Arg Arg Leu Glu Asn
1               5                   10

<210> SEQ ID NO 40
<211> LENGTH: 14
<212> TYPE: PRT
<213> ORGANISM: Artificial Sequence
<220> FEATURE:
<223> OTHER INFORMATION: synthesized

<400> SEQUENCE: 40

Gln Ser Gln Gln Thr Phe Asn Leu Trp Arg Leu Leu Gln Asn
1               5                   10

<210> SEQ ID NO 41
<211> LENGTH: 14
<212> TYPE: PRT
<213> ORGANISM: Artificial Sequence
<220> FEATURE:
<223> OTHER INFORMATION: synthesized

<400> SEQUENCE: 41

Arg Ser Gln Gln Arg Phe Arg Leu Trp Arg Arg Leu Gln Asn
1               5                   10

<210> SEQ ID NO 42
<211> LENGTH: 33
<212> TYPE: DNA
<213> ORGANISM: Artificial Sequence
<220> FEATURE:
<223> OTHER INFORMATION: synthesized
```

```
<400> SEQUENCE: 42
gcgctaggat ccatcgccac catggtgagc aag                              33

<210> SEQ ID NO 43
<211> LENGTH: 33
<212> TYPE: DNA
<213> ORGANISM: Artificial Sequence
<220> FEATURE:
<223> OTHER INFORMATION: synthesized

<400> SEQUENCE: 43
ccatggccgg ccgcggccgc tttacttgta cag                              33

<210> SEQ ID NO 44
<211> LENGTH: 27
<212> TYPE: DNA
<213> ORGANISM: Artificial Sequence
<220> FEATURE:
<223> OTHER INFORMATION: synthesized

<400> SEQUENCE: 44
ggaggacagt actccgtcta gaaactc                                     27

<210> SEQ ID NO 45
<211> LENGTH: 33
<212> TYPE: DNA
<213> ORGANISM: Artificial Sequence
<220> FEATURE:
<223> OTHER INFORMATION: synthesized

<400> SEQUENCE: 45
gagaatgact ctacccggca tgtacgacca atg                              33

<210> SEQ ID NO 46
<211> LENGTH: 33
<212> TYPE: DNA
<213> ORGANISM: Artificial Sequence
<220> FEATURE:
<223> OTHER INFORMATION: synthesized

<400> SEQUENCE: 46
ctcttactga gatgggccgt acatgctggt tac                              33

<210> SEQ ID NO 47
<211> LENGTH: 29
<212> TYPE: DNA
<213> ORGANISM: Artificial Sequence
<220> FEATURE:
<223> OTHER INFORMATION: synthesized

<400> SEQUENCE: 47
gagaatgact ctacccggca tgtacgacc                                   29

<210> SEQ ID NO 48
<211> LENGTH: 29
<212> TYPE: DNA
<213> ORGANISM: Artificial Sequence
<220> FEATURE:
<223> OTHER INFORMATION: synthesized

<400> SEQUENCE: 48
ggtcgtacat gccgggtaga gtcattctc                                   29

<210> SEQ ID NO 49
<211> LENGTH: 28
```

```
<212> TYPE: DNA
<213> ORGANISM: Artificial Sequence
<220> FEATURE:
<223> OTHER INFORMATION: synthesized

<400> SEQUENCE: 49
ggtggagatc atatagacaa tcaagtgc                                           28

<210> SEQ ID NO 50
<211> LENGTH: 45
<212> TYPE: DNA
<213> ORGANISM: Artificial Sequence
<220> FEATURE:
<223> OTHER INFORMATION: synthesized

<400> SEQUENCE: 50
gccttgagct cgactccaaa gaatcattaa ctcctggtag agaag                        45

<210> SEQ ID NO 51
<211> LENGTH: 46
<212> TYPE: DNA
<213> ORGANISM: Artificial Sequence
<220> FEATURE:
<223> OTHER INFORMATION: synthesized

<400> SEQUENCE: 51
ggtccggatc ctcacttttg atgaaacaga agtttttga tatttc                        46

<210> SEQ ID NO 52
<211> LENGTH: 37
<212> TYPE: PRT
<213> ORGANISM: Artificial Sequence
<220> FEATURE:
<223> OTHER INFORMATION: synthesized

<400> SEQUENCE: 52

Lys Gly Pro Ser Gln Pro Thr Tyr Pro Gly Asp Asp Ala Pro Val Arg
1               5                   10                  15

Asp Leu Ile Arg Pro Tyr Arg Asp Leu Gln Arg Pro Leu Arg Val Val
            20                  25                  30

Thr Arg His Arg Tyr
        35

<210> SEQ ID NO 53
<211> LENGTH: 37
<212> TYPE: PRT
<213> ORGANISM: Artificial Sequence
<220> FEATURE:
<223> OTHER INFORMATION: synthesized

<400> SEQUENCE: 53

Lys Gly Pro Ser Gln Pro Thr Tyr Pro Gly Asp Asp Ala Pro Val Arg
1               5                   10                  15

Asp Leu Ile Arg Pro Tyr Arg Asp Leu Arg Arg Pro Leu Asn Val Val
            20                  25                  30

Thr Arg His Arg Tyr
        35

<210> SEQ ID NO 54
<211> LENGTH: 26
<212> TYPE: PRT
<213> ORGANISM: Artificial Sequence
<220> FEATURE:
<223> OTHER INFORMATION: synthesized
```

```
<400> SEQUENCE: 54

Lys Phe Gln Cys Arg Ile Cys Met Arg Asn Phe Ser Asp Arg Ser Asn
1               5                   10                  15

Leu Ser Arg His Ile Arg Thr His Thr Pro
            20                  25

<210> SEQ ID NO 55
<211> LENGTH: 26
<212> TYPE: PRT
<213> ORGANISM: Artificial Sequence
<220> FEATURE:
<223> OTHER INFORMATION: synthesized

<400> SEQUENCE: 55

Lys Phe Ala Cys Asp Ile Cys Gly Arg Lys Phe Ala Ile Ser Ser Asn
1               5                   10                  15

Leu Asn Ser His Thr Lys Ile His Thr Pro
            20                  25

<210> SEQ ID NO 56
<211> LENGTH: 26
<212> TYPE: PRT
<213> ORGANISM: Artificial Sequence
<220> FEATURE:
<223> OTHER INFORMATION: synthesized

<400> SEQUENCE: 56

Lys Phe Gln Cys Arg Ile Cys Met Arg Asn Phe Ser Arg Ser Asp Asn
1               5                   10                  15

Leu Ala Arg His Ile Arg Thr His Thr Pro
            20                  25

<210> SEQ ID NO 57
<211> LENGTH: 26
<212> TYPE: PRT
<213> ORGANISM: Artificial Sequence
<220> FEATURE:
<223> OTHER INFORMATION: synthesized

<400> SEQUENCE: 57

Lys Phe Ala Cys Asp Ile Cys Gly Arg Lys Phe Ala Thr Ser Gly Asn
1               5                   10                  15

Leu Thr Arg His Thr Lys Ile His Leu Arg
            20                  25

<210> SEQ ID NO 58
<211> LENGTH: 36
<212> TYPE: PRT
<213> ORGANISM: Artificial Sequence
<220> FEATURE:
<223> OTHER INFORMATION: synthesized

<400> SEQUENCE: 58

Gly Pro Ser Gln Pro Thr Tyr Pro Gly Asp Asp Ala Pro Val Glu Asp
1               5                   10                  15

Leu Ile Arg Phe Tyr Asn Asp Leu Gln Gln Tyr Leu Asn Val Val Thr
            20                  25                  30

Arg His Arg Tyr
        35

<210> SEQ ID NO 59
<211> LENGTH: 36
<212> TYPE: PRT
```

<213> ORGANISM: Artificial Sequence
<220> FEATURE:
<223> OTHER INFORMATION: synthesized

<400> SEQUENCE: 59

Gly Pro Ser Gln Pro Thr Tyr Pro Gly Asp Asp Ala Pro Val Glu Asp
1               5                   10                  15

Leu Ile Arg Phe Tyr Asn Asp Leu Gln Arg Tyr Leu Asn Val Val Thr
            20                  25                  30

Arg His Arg Tyr
        35

<210> SEQ ID NO 60
<211> LENGTH: 36
<212> TYPE: PRT
<213> ORGANISM: Artificial Sequence
<220> FEATURE:
<223> OTHER INFORMATION: synthesized

<400> SEQUENCE: 60

Gly Pro Ser Gln Pro Thr Tyr Pro Gly Asp Asp Ala Pro Val Glu Asp
1               5                   10                  15

Leu Ile Arg Phe Tyr Arg Asp Leu Gln Gln Tyr Leu Asn Val Val Thr
            20                  25                  30

Arg His Arg Tyr
        35

<210> SEQ ID NO 61
<211> LENGTH: 36
<212> TYPE: PRT
<213> ORGANISM: Artificial Sequence
<220> FEATURE:
<223> OTHER INFORMATION: synthesized

<400> SEQUENCE: 61

Gly Pro Ser Gln Pro Thr Tyr Pro Gly Asp Asp Ala Pro Val Glu Asp
1               5                   10                  15

Leu Ile Arg Phe Tyr Arg Asp Leu Gln Arg Tyr Leu Asn Val Val Thr
            20                  25                  30

Arg His Arg Tyr
        35

<210> SEQ ID NO 62
<211> LENGTH: 36
<212> TYPE: PRT
<213> ORGANISM: Artificial Sequence
<220> FEATURE:
<223> OTHER INFORMATION: synthesized

<400> SEQUENCE: 62

Gly Pro Ser Gln Pro Thr Tyr Pro Gly Asp Asp Ala Pro Val Arg Asp
1               5                   10                  15

Leu Ile Arg Phe Tyr Arg Asp Leu Gln Arg Tyr Leu Asn Val Val Thr
            20                  25                  30

Arg His Arg Tyr
        35

<210> SEQ ID NO 63
<211> LENGTH: 36
<212> TYPE: PRT
<213> ORGANISM: Artificial Sequence
<220> FEATURE:
<223> OTHER INFORMATION: synthesized

<400> SEQUENCE: 63

Gly Pro Ser Gln Pro Thr Tyr Pro Gly Asp Asp Ala Pro Val Glu Asp
1               5                   10                  15

Leu Ile Arg Phe Tyr Arg Asp Leu Arg Arg Tyr Leu Asn Val Val Thr
            20                  25                  30

Arg His Arg Tyr
        35

<210> SEQ ID NO 64
<211> LENGTH: 36
<212> TYPE: PRT
<213> ORGANISM: Artificial Sequence
<220> FEATURE:
<223> OTHER INFORMATION: synthesized

<400> SEQUENCE: 64

Gly Pro Ser Gln Pro Thr Tyr Pro Gly Asp Asp Ala Pro Val Arg Asp
1               5                   10                  15

Leu Ile Arg Phe Tyr Arg Asp Leu Gln Arg Tyr Leu Arg Val Val Thr
            20                  25                  30

Arg His Arg Tyr
        35

<210> SEQ ID NO 65
<211> LENGTH: 36
<212> TYPE: PRT
<213> ORGANISM: Artificial Sequence
<220> FEATURE:
<223> OTHER INFORMATION: synthesized

<400> SEQUENCE: 65

Gly Pro Ser Gln Pro Thr Tyr Pro Gly Asp Asp Ala Pro Val Arg Asp
1               5                   10                  15

Leu Ile Arg Phe Tyr Arg Asp Leu Arg Arg Tyr Leu Asn Val Val Thr
            20                  25                  30

Arg His Arg Tyr
        35

<210> SEQ ID NO 66
<211> LENGTH: 36
<212> TYPE: PRT
<213> ORGANISM: Artificial Sequence
<220> FEATURE:
<223> OTHER INFORMATION: synthesized

<400> SEQUENCE: 66

Gly Pro Ser Gln Pro Thr Tyr Pro Gly Asp Asp Ala Pro Val Arg Asp
1               5                   10                  15

Leu Arg Arg Phe Tyr Arg Asp Leu Arg Arg Tyr Leu Asn Val Val Thr
            20                  25                  30

Arg His Arg Tyr
        35

<210> SEQ ID NO 67
<211> LENGTH: 14
<212> TYPE: PRT
<213> ORGANISM: Artificial Sequence
<220> FEATURE:
<223> OTHER INFORMATION: synthesized

<400> SEQUENCE: 67

```
Gly Arg Lys Lys Arg Gln Arg Arg Pro Pro Gln Tyr
1               5                   10
```

<210> SEQ ID NO 68
<211> LENGTH: 8
<212> TYPE: PRT
<213> ORGANISM: Artificial Sequence
<220> FEATURE:
<223> OTHER INFORMATION: synthesized

<400> SEQUENCE: 68

```
Arg Arg Arg Arg Arg Arg Arg Arg
1               5
```

<210> SEQ ID NO 69
<211> LENGTH: 28
<212> TYPE: PRT
<213> ORGANISM: Artificial Sequence
<220> FEATURE:
<223> OTHER INFORMATION: synthesized

<400> SEQUENCE: 69

```
Trp Tyr Ser Cys Asn Val Cys Gly Lys Ala Phe Val Leu Ser Ala His
1               5                   10                  15

Leu Asn Gln His Leu Ala Val His Thr Gln Ala Thr
            20                  25
```

<210> SEQ ID NO 70
<211> LENGTH: 28
<212> TYPE: PRT
<213> ORGANISM: Artificial Sequence
<220> FEATURE:
<223> OTHER INFORMATION: synthesized

<400> SEQUENCE: 70

```
Trp Tyr Ser Cys Asn Val Cys Gly Lys Ala Phe Val Leu Ser Arg His
1               5                   10                  15

Leu Asn Arg His Leu Arg Val His Arg Arg Ala Thr
            20                  25
```

<210> SEQ ID NO 71
<211> LENGTH: 25
<212> TYPE: PRT
<213> ORGANISM: Artificial Sequence
<220> FEATURE:
<223> OTHER INFORMATION: synthesized

<400> SEQUENCE: 71

```
Phe Gln Cys Arg Ile Cys Met Arg Asn Phe Ser Asp Arg Ser Asn Leu
1               5                   10                  15

Ser Arg His Ile Arg Thr His Thr Pro
            20                  25
```

<210> SEQ ID NO 72
<211> LENGTH: 25
<212> TYPE: PRT
<213> ORGANISM: Artificial Sequence
<220> FEATURE:
<223> OTHER INFORMATION: synthesized

<400> SEQUENCE: 72

```
Phe Ala Cys Asp Ile Cys Gly Arg Lys Phe Ala Ile Ser Ser Asn Leu
1               5                   10                  15

Asn Ser His Thr Lys Ile His Thr Pro
            20                  25
```

```
<210> SEQ ID NO 73
<211> LENGTH: 25
<212> TYPE: PRT
<213> ORGANISM: Artificial Sequence
<220> FEATURE:
<223> OTHER INFORMATION: synthesized

<400> SEQUENCE: 73

Phe Gln Cys Arg Ile Cys Met Arg Asn Phe Ser Arg Ser Asp Asn Leu
1               5                   10                  15

Ala Arg His Ile Arg Thr His Thr Pro
            20                  25

<210> SEQ ID NO 74
<211> LENGTH: 25
<212> TYPE: PRT
<213> ORGANISM: Artificial Sequence
<220> FEATURE:
<223> OTHER INFORMATION: synthesized

<400> SEQUENCE: 74

Phe Ala Cys Asp Ile Cys Gly Arg Lys Phe Ala Thr Ser Gly Asn Leu
1               5                   10                  15

Thr Arg His Thr Lys Ile His Leu Arg
            20                  25
```

UNITED STATES PATENT AND TRADEMARK OFFICE
CERTIFICATE OF CORRECTION

| | | |
|---|---|---|
| PATENT NO. | : 11,155,580 B2 | Page 1 of 1 |
| APPLICATION NO. | : 16/250213 | |
| DATED | : October 26, 2021 | |
| INVENTOR(S) | : Alanna Schepartz Shrader et al. | |

It is certified that error appears in the above-identified patent and that said Letters Patent is hereby corrected as shown below:

In the Specification

At Column 1, Lines 19-25, The Statement Regarding Federally Sponsored Research or Development should read as follows:
--This invention was made with government support under HV028186 and GM074756 awarded by National Institutes of Health. The government has certain rights in the invention.--

Signed and Sealed this
Nineteenth Day of August, 2025

Coke Morgan Stewart
*Acting Director of the United States Patent and Trademark Office*